(12) United States Patent
Brahmbhatt et al.

(10) Patent No.: US 11,964,021 B2
(45) Date of Patent: Apr. 23, 2024

(54) BACTERIALLY DERIVED, INTACT MINICELLS FOR DELIVERY OF THERAPEUTIC AGENTS TO BRAIN TUMORS

(71) Applicant: EnGeneIC Molecular Delivery Pty Ltd, Sydney (AU)

(72) Inventors: Himanshu Brahmbhatt, Sydney (AU); Jennifer MacDiarmid, Sydney (AU)

(73) Assignee: EnGeneIC Molecular Delivery Pty Ltd, Sydney (AU)

( * ) Notice: Subject to any disclaimer, the term of this patent is extended or adjusted under 35 U.S.C. 154(b) by 408 days.

(21) Appl. No.: 17/212,995

(22) Filed: Mar. 25, 2021

(65) Prior Publication Data

US 2021/0213133 A1    Jul. 15, 2021

Related U.S. Application Data

(60) Division of application No. 15/790,885, filed on Oct. 23, 2017, now Pat. No. 10,994,014, which is a continuation of application No. 13/711,848, filed on Dec. 12, 2012, now Pat. No. 9,844,598.

(60) Provisional application No. 61/569,907, filed on Dec. 13, 2011.

(51) Int. Cl.
*A61K 47/46* (2006.01)
*A61K 9/50* (2006.01)
*A61K 47/68* (2017.01)
*A61K 51/12* (2006.01)

(52) U.S. Cl.
CPC .......... *A61K 47/46* (2013.01); *A61K 9/5068* (2013.01); *A61K 47/6849* (2017.08); *A61K 51/1203* (2013.01)

(58) Field of Classification Search
CPC ......... A61P 35/00; A61K 47/46; A61K 47/48; A61K 51/12
See application file for complete search history.

(56) References Cited

U.S. PATENT DOCUMENTS

| | | | |
|---|---|---|---|
| 6,540,980 B1 | 4/2003 | Blumenthal et al. | |
| 6,803,052 B2 | 10/2004 | Faisant et al. | |
| 6,962,702 B2 | 11/2005 | Griffiths et al. | |
| 7,183,105 B2 | 2/2007 | Sabbadini | |
| 9,844,598 B2 | 12/2017 | Brahmbhatt et al. | |
| 9,867,785 B2 | 1/2018 | Brahmbhatt et al. | |
| 2002/0006379 A1 | 1/2002 | Hansen et al. | |
| 2002/0119153 A1 | 8/2002 | Thorpe et al. | |
| 2003/0203411 A1 | 10/2003 | Sabbadini et al. | |
| 2004/0005700 A1 | 1/2004 | Surber et al. | |
| 2005/0222057 A1 | 10/2005 | Brahmbhatt et al. | |
| 2006/0039914 A1 | 2/2006 | O'Neill et al. | |
| 2008/0038296 A1 | 2/2008 | Brahmbhatt et al. | |
| 2008/0051469 A1* | 2/2008 | Brahmbhatt ......... A61K 9/5068 514/777 |
| 2008/0188436 A1 | 8/2008 | Brahmbhatt et al. | |
| 2008/0299084 A1 | 12/2008 | Brahmbhatt et al. | |
| 2009/0010840 A1 | 1/2009 | Adams | |
| 2009/0311181 A1 | 12/2009 | Wu et al. | |
| 2010/0196989 A1 | 8/2010 | Hansen et al. | |
| 2010/0215581 A1 | 8/2010 | Hoffmann | |
| 2011/0177185 A1 | 7/2011 | Brahmbhatt et al. | |
| 2013/0261170 A1 | 10/2013 | Brahmbhatt et al. | |
| 2018/0280311 A1 | 10/2018 | Brahmbhatt et al. | |

FOREIGN PATENT DOCUMENTS

| | | |
|---|---|---|
| CN | 1599797 A | 3/2005 |
| CN | 1809629 A | 7/2006 |
| CN | 1925873 A | 3/2007 |
| CN | 101072876 A | 11/2007 |
| JP | 2002-541124 | 12/2002 |
| JP | 2007-534667 | 11/2007 |
| JP | 2008-500396 | 1/2008 |
| JP | 2009-531324 | 9/2009 |
| JP | 2010-507645 | 3/2010 |
| JP | 2010-209098 | 9/2010 |
| JP | 2010-215626 | 9/2010 |
| JP | 2011-046720 | 3/2011 |
| JP | 6522340 | 5/2019 |

(Continued)

OTHER PUBLICATIONS

Russian Official Action issued in related Russian patent application No. 2014128338, dated May 25, 2017.
Gambarota, et al., "Characterization of tumour vasculature in mouse brain by USPIO contrast-enhanced MRI," *British Journal of Cancer*, vol. 98, pp. 1784-1789 (2008).
Macdiarmid, et al., "Sequential treatment of drug-resistant tumors with targeted minicells containing siRNA or a cytotoxic drug", Nature Biotechnology, vol. 27, No. 7, pp. 643-654, (2009).
Macdiarmid et al., "Bacterially-Derived Nanocells for Tumor-Targeted Delivery of Chemotherapeutics and Cell Cycle Inhibitors," Cell Cycle, Sep. 7, 2007, vol. 6, No. 7, pp. 2099-2105.
W. Gregory Roberts et al., "Host Microvasculature Influence on Tumor Vascular Morphology and Endothelial Gene Expression," American Journal of Pathology, Oct. 1998, vol. 153, No. 4, pp. 1239-1248.
Search Report and Written Opinion issued in related Singapore Patent Application No. 11201403062Y, dated Apr. 22, 2015.

(Continued)

*Primary Examiner* — Michael G. Hartley
*Assistant Examiner* — Jagadishwar R Samala
(74) *Attorney, Agent, or Firm* — Foley & Lardner LLP

(57) ABSTRACT

Systemic administration of intact, bacterially derived minicells results in rapid accumulation of the minicells in the microenvironment of a brain tumor, in therapeutically significant concentrations, without requiring endothelial endocytosis/transcytosis across the blood brain barrier or any other mechanism by which, pursuant to conventional approaches, nanoparticles have entered into that microenvironment. Accordingly, a wide variety of brain tumors, both primary and metastatic, can be treated by administering systemically a therapeutically effective amount of a composition comprised of a plurality of such minicells, each minicell being a vehicle for an active agent against the tumor, such as a radionuclide, a functional nucleic acid or a plasmid encoding one, or a chemotherapeutic agent.

15 Claims, 18 Drawing Sheets

(56) References Cited

FOREIGN PATENT DOCUMENTS

| WO | WO 00/59547 | | 10/2000 |
|---|---|---|---|
| WO | WO 00/64946 | | 11/2000 |
| WO | WO 02/082041 | A2 | 10/2002 |
| WO | WO2003/101495 | A1 | 12/2003 |
| WO | WO-2004/113507 | A1 | 12/2004 |
| WO | WO 2005/079854 | A1 | 9/2005 |
| WO | WO 2005079854 | * | 9/2005 |
| WO | WO 2005/113000 | A2 | 12/2005 |
| WO | WO 2006/021894 | A2 | 3/2006 |
| WO | WO2006/099445 | A2 | 9/2006 |
| WO | WO 2007/109321 | A2 | 9/2007 |
| WO | WO 2008/050255 | A2 | 5/2008 |
| WO | WO-2010/065969 | | 6/2010 |
| WO | WO2011/131746 | | 10/2011 |
| WO | WO 2020/021437 | A1 | 1/2020 |

OTHER PUBLICATIONS

Russian Official Action issued in related Russian patent application No. 2014128338, dated Jan. 24, 2017.
International Search Report from PCT/IB2012/002950 dated Dec. 9, 2013.
MacDiarmid et al., Bacterially Derived 400 nm Particles for Encapsulation and Cancer Cell Targeting of Chemotherapeutics, Cancer Cell, vol. 11, pp. 431-445 (2007).
Office Action issued in Russian Patent Application No. 2014128338, dated Nov. 16, 2017.
Notice of Reasons for Rejection issued in co-pending Japanese Patent Application No. 2017-158959 dated Jun. 26, 2018.
First Office Action and Search Report on CN Application No. 201811227385.X dated Jun. 1, 2020, 13 pages.
Gambarota, et al., "Characterization of tumor vasculature in mouse brain by USPIO contrast-enhanced MRI," *Methods in Molecular Biology*, vol. 771, pp. 477-487 (2011).
Coomber, B. L. et al., Quantitative morphology of human glioblastoma multiforme microvessels: structural basis of blood-brain barrier defect J. Neuro-Oncol. 5: 299-307, 1987.
Zhan, et al., "The blood-brain/tumor barriers: challenges and chances for malignant gliomas targeted drug delivery," *Current Pharmaceutical Biotechnology*, vol. 13, pp. 2380-2387 (2012).
Trial Decision issued in Korean Patent Application No. 10-2014-7019228, dated Jul. 23, 2020.
Pardridge, et al., "The Blood-Brain Barrier: Bottleneck in Brain Drug Development," *NeuroTx: The Journ. of the American Society for Experimental Neuro Therapeutics*, vol. 2, pp. 3-14 (Jan. 2005).
Second Office Action issued in Chinese Office Patent Application No. 201811227385.X dated Jan. 14, 2021.
Chemotherapy of Central Nervous System Tumors, "Malignant Tumor Chemotherapy", Zhang Zhiyi, et al., Shanghai Scientific & Technical Publishers, pp. 363-365, the publication date (Nov. 30, 1981).
Behin, et al., "Primary brain tumours in adults," *Lancet* 361, pp. 323-331 (2003).
Bickel, "How to Measure Drug Transport across the Blood-Brain Barrier," *NeuroRx*. 2, pp. 15-26 (2005).
Black, et al., "Modulation of brain tumor capillaries for enhanced drug delivery selectively to brain tumor," *Cancer Control* 11, pp. 165-173 (2004).
Bobo, et al., "Convection-enhanced delivery of macromolecules in the brain," *Proc. Natl. Acad. Sci. U S A* 91, pp. 2076-2080 (1994).
Borst, et al. "A family of drug transporters: the multidrug resistance-associated proteins," *J. Natl. Cancer Inst.* 92, pp. 1295-1302 (2000).
Britton et al., "Characterization of a prokaryotic SMC protein involved in chromosome partitioning", Genes & Development, 1998, vol. 12, pp. 1254-1259.
Caplen et al., "Short Interfering RNA (siRNA)-Mediated RNA Interference (RNAi) in Human Cells", Annals New York Academy of Sciences, 2003, 1002, pp. 56-62.

Caplen, "RNAi as a gene therapy approach", Expert Opin. Biol. Ther., 2003, Vo. 3, No. 4, pp. 575-586.
Caravella, et al., "Design of next-generation protein therapeutics," *Curr. Opin. Chem. Biol.* 14, pp. 520-528 (2010).
Cecchelli, et al., "Modelling of the blood-brain barrier in drug discovery and development," *Nat. Rev. Drug Discov.* 6, pp. 650-661 (2007).
Chu et al., Translation Repression in Human Cells by MicroRNA-Induced Gene Silencing Requires RCK/p54, *PLoS Biology* 4: pp. 1122-1136 (2006).
Da Silva et al., HER3 and downstream pathways are involved in colonization of brain metastases from breast cancer, *Breast Cancer Res.* 12: R46 (1-13) (2010).
De Boer et al., "Roles of MinC and MinD in the Site-Specific Septation Block Mediated by the MinCDE System of *Escherichia coli*", Journal of Bacteriology, 1992, vol. 174, No. 1, pp. 63-70.
Debinski et al., "Expression of a restrictive receptor for interleukin 13 is associated with glial transformation," *J. Neurooncol.* 48: 103-111 (2000). [Abstract].
Debinski et al., "Molecular Expression Analysis of Restrictive Receptor for Interleukin 13, a Brain Tumor-associated Cancer/Testis Antigen," *Mol. Med.* 6: 440-449 (2000).
Dehouck, et al., "Upregulation of the low-density lipoprotein receptor at the blood-brain barrier: intercommunications between brain capillary endothelial cells and astrocytes," *J. Cell Biol.* 126, pp. 465-473 (1994).
Duan et al., "Inhibition of ABCB1 (MDR1) and ABCB4 (MDR3) expression by small interfering RNA and reversal of paclitaxel resistance in human ovarian cancer cells", Molecular Cancer Therapeutics, 2004, vol. 3, No. 7, pp. 833-838.
Duxbury et al., "Systemic siRNA-Mediated Gene Silencing a New Approach to Targeted Therapy of Cancer," *Ann. Surg.* 240: 667-674 (2004).
Eichler, et al., "Multidisciplinary management of brain metastases," *Oncologist* 12, 884-898 (2007).
Fox, et al., "Epidemiology of metastatic brain tumors," *Neurosurg. Clin. N. Am.* 22, 1-6 (2011).
Gregory et al., "MicroRNA Biogenesis: *Isolation and Characterization of the Microprocessor Complex Methods in Molecular Biology*," vol. 342, pp. 33-47 (2006). [Abstract].
Groothuis, D.R. The blood-brain and blood tumor barriers: a review of strategies for increasing drug delivery. *Neuro-oncol.* 2, 45-59 (2000).
Hadjipanayis, et al. EGFRvIII antibody-conjugated iron oxide nanoparticles for magnetic resonance imaging-guided convection-enhanced delivery and targeted therapy of glioblastoma. *Cancer Res.* 70, 6303-6312 (2010).
Hassenbusch, S.J., Gunes, S., Wachsman, S., Willis, K.D. Intrathecal clonidine in the treatment of intractable pain: a phase I/II study. *Pain Med.* 3, 85-91 (2002).
Hau, et al., "Effect of guanidino modification and proline substitution on the in vitro stability and blood-brain barrier permeability of endomorphin II," *J. Pharm. Sci.* 91, 2140-2149 (2002).
Hawkins, B.T., Davis, T.P. The blood-brain barrier/neurovascular unit in health and disease. *Pharmacological Reviews* 57, 173-185 (2005).
Hershey, "IL-13 receptors and signaling pathways: an evolving web," *J. Allergy Clin. Immunol.*, vol. 111, pp. 677-690 (2003).
Hiraga et al., "Chromosome Partitioning in *Escherichia coli*: Novel Mutants Producing Anucleate Cells", Journal of Bacteriology, 1989, vol. 171, No. 3, pp. 1496-1505.
Hoppner, "Clinical Impact of Molecular Diagnostics in Endocrinology," (Horm re. 2002, 58 Suppl. 3: 7-15). [Abstract].
Hu et al., "Topological regulation of cell division in *Escherichia coli* involves rapid pole to pole oscillation of the division inhibitor MinC under the control of MinD and MinE", Molecular Microbiology, 1999, vol. 34, No. 1, pp. 82-90.
Hussner et al., "Regulation of Interferon-Inducible Proteins by Doxorubicin via Interferon—Janus Tyrosine Kinase-Signal Transducer and Activator of Transcription Signaling in Tumor Cells," *Molecular Pharmacology*, vol. 81, No. 5, pp. 679-688 (2012).

(56) References Cited

OTHER PUBLICATIONS

International Preliminary Report on Patentability issued in related International Patent Application No. PCT/IB2014/002824, dated Apr. 14, 2016.

International Search Report issued in related International Patent Application No. PCT/IB2014/002824, dated Feb. 13, 2015.

Ireton et al., "spo0J Is Required for Normal Chromosome Segregation as well as the Initiation of Sporulation in *Bacillus subtilis*", Journal of Bacteriology, 1994, vol. 176, No. 17, pp. 5320-5329.

Jarboe et al., "Expression of Interleukin-13 Receptor α2 in Glioblastoma Multiforme: Implications for Targeted Therapies," *Cancer Res.* 67: 7983-7986 (2007).

Khalil et al., "Many human large intergenic noncoding RNAs associate with chromatin-modifying complexes and affect gene expression," *Proc Nat'l Acad. USA* 106: pp. 11667-11672 (2009).

Kota et al., "Therapeutic delivery of miR-26a inhibits cancer cell proliferation and induces tumor-specific apoptosis," *Cell* 137: 1005-1017 (2009).

Nieth et al., "Modulation of the classical multidrug resistance (MDR) phenotype by RNA interference (RNAi)", FEBS Letters 545 (2003) pp. 144-150.

Oh et al., "siRNA delivery systems for cancer treatment," *Advanced Drug Delivery Rev.* 61: 850-62 (2009). [Abstract].

Okada et al., "Cytoplasmic Axial Filaments in *Escherichia coli* Cells: Possible Function in the Mechanism of Chromosome Segregation and Cell Division", Journal of Bacteriology, Feb. 1994, pp. 917-922.

Quintiero et al., "Formation and Antitumor Activity of PNU-159682, a Major Metabolite of Nemorubicin in Human Liver Microsomes," American Association for Cancer Research, vol. 11, pp. 1608-1617 (2005).

Raskin et al., "MinDE-Dependent Pole-to-Pole Oscillation of Division Inhibitor MinC in *Escherichia coli*", Journal of Bacteriology, vol. 181, No. 20, Oct. 1999, pp. 6419-6424.

Reeve, J.N., Cornett, J.B. Bacteriophage SPO1-induced macromolecular synthesis in minicells of Bacillus subtilis. *J. Virol.* 15, 1308-1316 (1975).

Rice et al., The next generation of Positron Emission Tomography Radiopharmaceuticals in Oncology, *Semin. Nucl. Med.*, vol. 41, pp. 265-282 (2011).

Search Report and Written Opinion issued in related Singapore Patent Application No. 11201602429Q, dated Mar. 16, 2017.

Sioud, "Therapeutic siRNAs", Trends in Pharmacological Sciences, vol. 25, No. 1, Jan. 2004, pp. 22-28.

Stewart et al., "Genetic and Morphological Characterization of an *Escherichia coli* Chromosome segregation Mutant", Journal of Bacteriology, Jul. 1992, vol. 174, No. 13, pp. 4513-4516.

Van der Meel, "Ligand-targeted particulate nanomedicines undergoing clinical evaluation: Current status," Advanced Drug Delivery Reviews, vol. 65, pp. 1284-1298 (2013).

Vincenzi et al., "Angiogenesis modifications related with cetuximab plus irinotecan as anticancer treatment in advanced colorectal cancer patients," *Ann Oncol.*, vol. 17, No. 5, pp. 835-841 (2006).

Wykosky et al., "Interleukin-13 Receptor α2, EphA2, and Fos-Related Antigen 1 as Molecular Denominators of High-Grade Astrocytomas and Specific Targets for Combinatorial Therapy," *Clin Cancer Res.* 14: 199-208 (2008).

Yagüe et al., "Complete reversal of multidrug resistance by stable expression of small interfering RNAs targeting MDR1", Gene Therapy 2004, vol. 6, No. 17, pp. 1170-1174.

Zaidi et al., "The Two Faces of Interferon-γ in Cancer," Clin. Cancer Res., 17(19), pp. 6118-6124 (2011).

Decision on Rejection issued in co-pending Chinese Patent Application No. 201811227385.X, dated Aug. 27, 2021.

\* cited by examiner

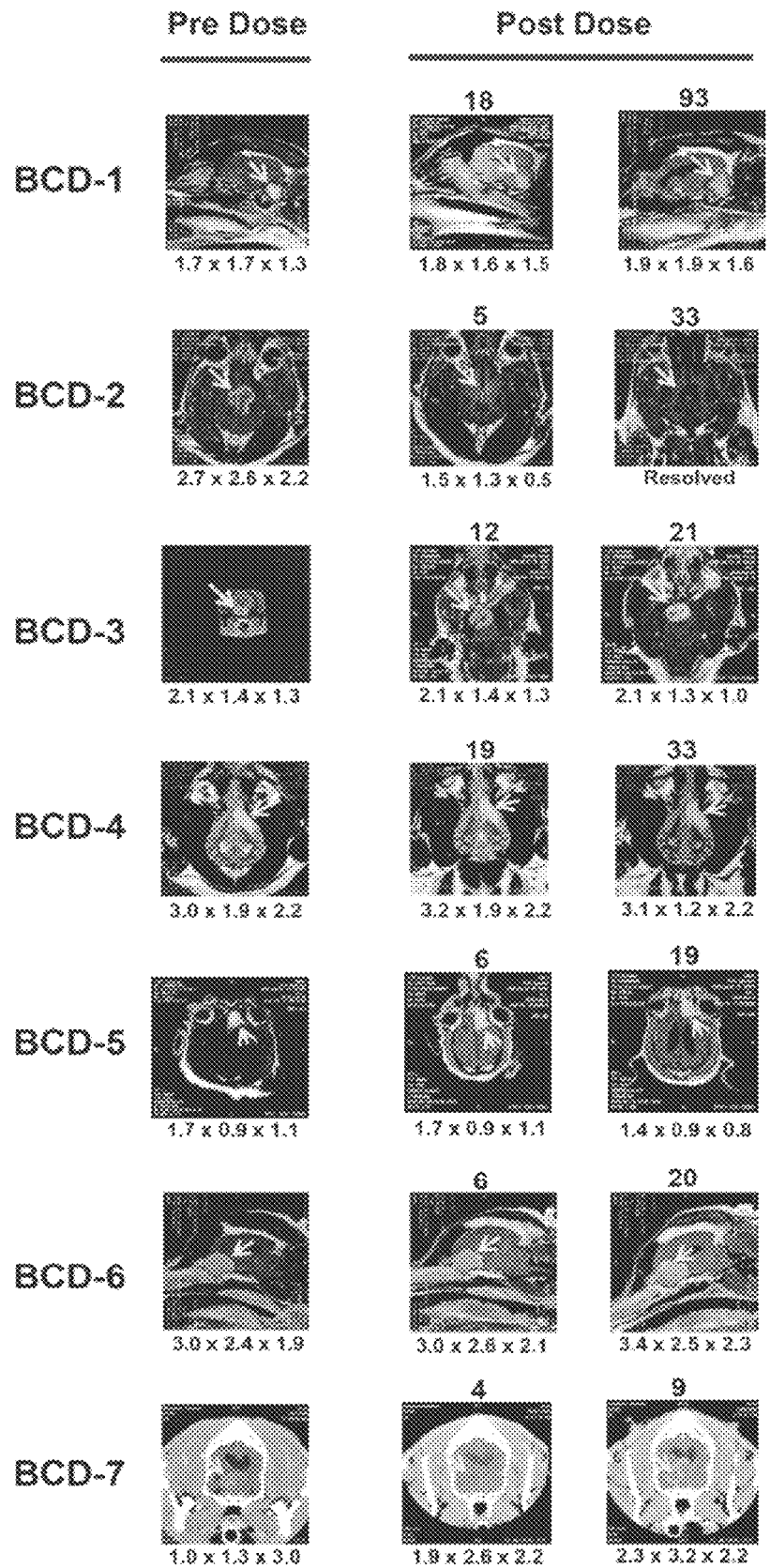

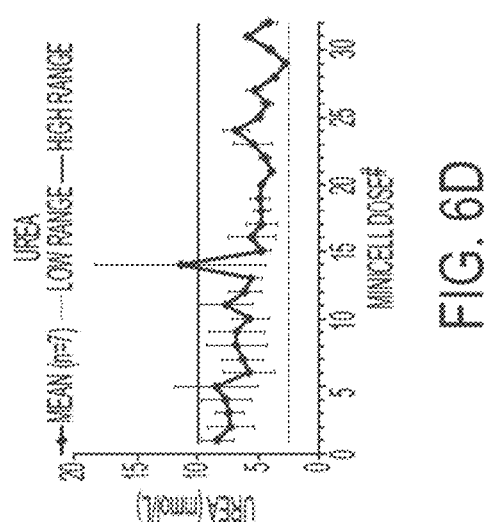

BACTERIALLY DERIVED, INTACT MINICELLS FOR DELIVERY OF THERAPEUTIC AGENTS TO BRAIN TUMORS

CROSS-REFERENCE TO RELATED APPLICATIONS

This application is a division of U.S. patent application Ser. No. 15/790,885, filed Oct. 23, 2017, which is a continuation of U.S. patent application Ser. No. 13/711,848, filed Dec. 12, 2012, now U.S. Pat. No. 9,844,598, which claims the benefit of priority from U.S. Provisional Patent Application No. 61/569,907, filed Dec. 13, 2011. The contents of these applications are incorporated herein by reference in their entirety.

BACKGROUND

Primary brain tumors consist of a diverse group of neoplasms, derived from various different cell lineages. Pursuant to a World Health Organization categorization (Louis et al., 2007), tumors of the central nervous system are classified as astrocytic, oligodendroglial, or mixed (oligoastrocytic). These tumors are further classified by subtypes and are graded, based on histology, from I to IV, with grade IV being the most aggressive. Glioblastoma multiforme (GBM), the most aggressive form of primary malignant brain tumor, accounts for approximately 45% to 50% of all primary brain tumors (Wrensch et al., 2002; Behin et al., 2003) and represents the second largest cause of cancer death in adults under 35 years of age (Allard et al., 2009).

Despite numerous therapeutic efforts, including cytoreductive surgery, radiation therapy and chemotherapy, the prognosis for glioma patients remains very poor (Stewart, 2002; Stupp et al., 2005). A majority eventually develop recurrent and progressive disease, after which the median survival is approximately 6 months (Wong et al., 1999; Lamborn et al., 2008). Median survival for GBM patients is about 12-14 months (Stupp et al., 2005).

In addition, brain metastasis from primary tumors such as breast, lung, and skin (melanoma) is a significant and growing public health problem. An estimated 250,000 patients in the United States were diagnosed with brain metastases in 2009 (Fox et al., 2011), which is more than 10-fold greater than the incidence of primary brain tumors (Jemal et al., 2009). The prognosis for patients with brain metastases is very poor, and most patients live only 4-6 months after diagnosis. Current treatment regimens provide marginal survival benefits (Eichler and Loeffler, 2007).

Complete surgical resection of gliomas is almost impossible, due to their diffusely infiltrative nature and proximity to vital brain structures. Systemic therapy also is limited, by virtue of the so-called blood brain barrier (BBB). See, generally, Cecchelli et al. (2007).

This barrier resides within the brain's capillary endothelium, and it has been an object of study for over 100 years. Indeed, the fact that most drug candidates for brain tumors never make it to the clinic (Pardridge, 2007) is attributable largely to their inability to cross the BBB and reach levels having a therapeutic effect (Groothuis, 2000).

Despite extensive efforts over several decades, the curative rates in the treatment of brain cancers remain abysmal. Brain cancer treatment thus represents one of the biggest challenges in oncology. Furthermore, the prevailing consensus is that the BBB is the major limiting factor in drug delivery into brain tumors.

Accordingly, considerable effort is directed globally to discovering and developing new drugs that are small enough to cross the BBB and improve the survival outcome for GBM patients. In addition, techniques are under development to transport drugs past the BBB and into the brain tumor microenvironment.

Among the approaches that have been studied, in an attempt to circumvent the BBB limitation, are the following.

Hyperosmotic BBB disruption (Kroll and Neuwelt, 1998).

Chemical barrier modification (Black et al., 1997).

Attempts to link therapeutic agents to compounds that have transporters across the BBB (Bickel et al., 2001; Zhang and Pardridge, 2007).

Direct administration of drugs into and around brain tumors (Hassenbusch et al., 2002; Hau et al., 2002; Reardon et al., 2002; Weber et al., 2002). This approach entails placement of drug-loaded wafers around a tumor resection bed, infusion of agents into or around a tumor resection cavity, or direct infusion of drugs into the tumor mass.

Convection-Enhanced Delivery or "CED" (Bobo et al., 1994; Morrison et al., 1994; Hadjipanayis et al., 2008; Hadjipanayis et al., 2010). In CED a small hydrostatic pressure differential is imposed by a syringe pump to distribute infusate directly to regions of the central nervous system (CNS). CED is a minimally invasive surgical procedure that provides fluid convection in the brain by a pressure gradient, which bypasses the BBB. Therapeutic agents can be delivered into the brain with a minimum of the toxicity, therefore, as well as to normal tissue and to organs commonly accessed by systemic delivery.

SUMMARY

In view of the drawbacks affecting conventional approaches in this area, a method is provided for administering systemically a therapeutically effective amount of a composition comprised of a plurality of intact, bacterially derived minicells, where each minicell of the plurality encompasses an anti-neoplastic agent. By the same token, the present description contemplates the use of such composition for manufacture of a medicament for the treatment of a brain tumor. The plurality can include at least about $10^8$ minicells, including but not limited to at least about $10^{10}$ minicells. Also, a composition as described here can contain less than about 10 EU free endotoxin and/or at most 1 parent bacterial cell per $10^8$ minicells, e.g., per $10^{10}$ minicells.

The anti-neoplastic agent encompassed by the minicells can be a radionuclide, for example, such as yttrium-90, technetium-99m, iodine-123, iodine-131, rubidium-82, thallium-201, gallium-67, fluorine-18, xenon-133, or indium-111, which can be attached to a protein or a carbohydrate on the surface of the minicells, or it can be attached on the surface of the tumor targeting ligand attached on the surface of the minicells. In this context, the composition can contain, for instance, between about 30 Gy to about 100 Gy radioactivity. The anti-neoplastic agent also can be a chemotherapy drug, where, for example, the composition contains at most about 1 mg thereof. Moreover, the anti-neoplastic agent can be a functional nucleic acid or a polynucleotide encoding a functional nucleic acid. Thus, the functional nucleic acid can inhibit a gene that promotes tumor cell proliferation, angiogenesis or resistance to chemotherapy and/or that inhibits apoptosis or cell cycle arrest. Illustrative of the class of functional nucleic acids are ribonucleic acid molecules selected from the group consisting of siRNA, miRNA, shRNA, lincRNA, antisense RNA, and ribozyme.

Pursuant to certain embodiments in accordance with any of the foregoing, each minicell of the above-mentioned plurality can comprise a ligand having a specificity to a non-phagocytic mammalian cell surface receptor, e.g., a tumor cell antigen. Accordingly, the ligand can comprise, for instance, an antibody that specifically recognizes such tumor cell antigen.

The methodology of this description can be used to treat a range of brain tumors, illustrated by but not limited to the group consisting of glioblastoma, astrocytic tumor, oligodendroglial tumor, ependymoma, craniopharyngioma, pituitary tumor, primary lymphoma of the brain, pineal gland tumor, primary germ cell tumor of the brain, and combinations thereof. The treated tumor can be a primary brain tumor or a metastatic brain tumor.

Other objects, features, and advantages are apparent from the following detailed description. The detailed description and specific examples are given for illustration only, since various changes and modifications within the spirit and scope of the particular embodiments will become apparent from this description.

BRIEF DESCRIPTION OF THE DRAWINGS

FIG. 5. Tumor stabilization/regression in seven dogs with late-stage brain tumors, post-treatment with $^{EGFR}$minicells$_{Dox}$. MM scans prior to treatment (Pre Dose) for each dog are shown in the left-hand vertical column. The middle- and the right-hand vertical columns show MRI scans, post-treatment with $^{EGFR}$minicells$_{Dox}$, and the post-dose number is shown for each MM. The depicted Mill sections include sagittal (BCD-1 and -6), axial (BCD-2 to -5) and coronal (BCD-7). Tumor volumes (dimensions in cm) are shown below each MM, and an arrow denotes the location of the respective tumors.

FIGS. 6A-6D. Serum biochemistry parameters were determined, post-treatment, for seven dogs with brain cancers (BCD-1 to BCD7). The horizontal lines in each graph represent the normal reference range in canines. Error bars, ±SEM.

(b) Results are shown for another animal. The transaxial views only are displayed for MRI (i) and SPECT (iii). Intense uptake is evident in the abnormality demonstrated on Mill. Image (ii) is a co-registered display of T1 post-contrast MRI, SPECT, and fused images. The arrows indicate an area of intense localization of radio-labelled minicells, which corresponded to a portion of the abnormality on the MRI scan.

(c) Shown are whole-body, 2D planar images at 30 minutes and 3 hours post-injection. Along with thyroid and some neck uptake, early uptake is seen in liver, with some excretion into bowel visible in the late scans.

Figure 12:
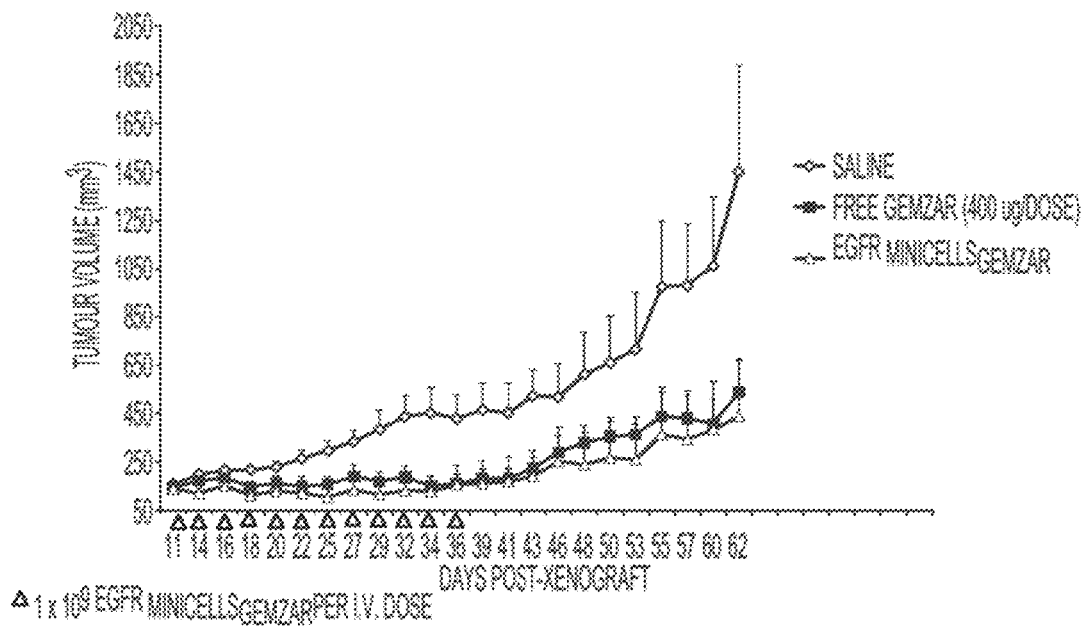

FIG. 12. Human pancreatic cancer (MIA PaCa) xenografts in Balb/c nu/nu mice (n=8 per group) were administered i.v. with either free Gemcitabine (Gemzar®) or EGFR-targeted, Gemzar-packaged minicells ($^{EGFR}$Minicells$_{Gemzar}$). All minicell treatments received $10^9$ minicells per dose. Treatment days are shown below the x-axis (triangles). Error bars: +/−SEM. The chart shows tumor volume at indicated days following the administration.

Figure 13:
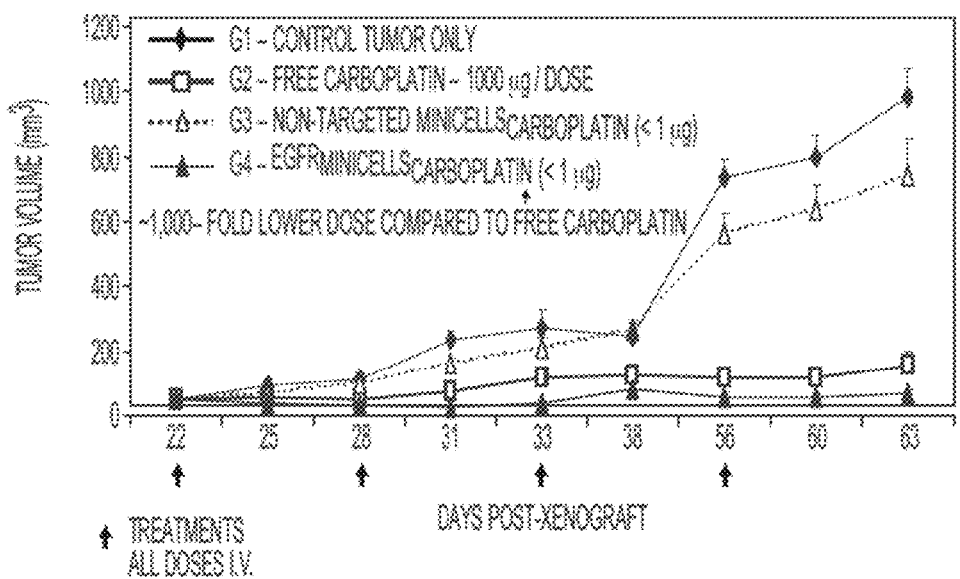

FIGURE. 13. Human breast cancer (MDA-MB-468) xenografts in Balb/c nu/nu mice (n=8 per group) were administered i.v. with free carboplatin or with minicells, packaged with carboplatin, that are either non-targeted or EGFR-targeted ($^{EGFR}$Minicells$_{Carboplatin}$). All minicell treatments received $10^9$ minicells per dose. Treatment days are shown below the x-axis (arrows). Error bars: +/−SEM. The chart shows tumor volume at indicated days following the administration.

DETAILED DESCRIPTION

The present disclosure provides compositions and methods for the treatment of brain tumors. In this respect, the inventors discovered that intact, bacterially derived minicells packaged with one or more anti-neoplastic agents, upon systemic administration, rapidly accumulate in the microenvironment of a brain tumor, in therapeutically significant concentrations. This finding was surprising because the minicells, approximately 400 nm in diameter, are much larger than what conventional understanding sets as the upper limit of 12 nm for a particle that is able to cross the blood brain barrier (BBB). See Sarin et al. (2008) and Laquintana et al. (2009).

Accordingly, the inventors determined that a wide variety of brain tumors, both primary and metastatic, can be treated by administering systemically a therapeutically effective amount of a composition comprised of a plurality of such minicells, each minicell being a vehicle for an active agent against the tumor.

(A) Definitions

Unless defined otherwise, all technical and scientific terms used in this description have the same meaning as commonly understood by those skilled in the relevant art.

For convenience, the meaning of certain terms and phrases employed in the specification, examples, and appended claims are provided below. Other terms and phrases are defined throughout the specification.

The singular forms "a," "an," and "the" include plural reference unless the context clearly dictates otherwise.

"Cancer," "neoplasm," "tumor," "malignancy" and "carcinoma," used interchangeably herein, refer to cells or tissues that exhibit an aberrant growth phenotype characterized by a significant loss of control of cell proliferation. The methods and compositions of this disclosure particularly apply to malignant, pre-metastatic, metastatic, and non-metastatic cells.

"Drug" refers to any physiologically or pharmacologically active substance that produces a local or systemic effect in animals, particularly mammals and humans.

"Individual," "subject," "host," and "patient," terms used interchangeably in this description, refer to any mammalian subject for whom diagnosis, treatment, or therapy is desired. The individual, subject, host, or patient can be a human or a non-human animal. Thus, suitable subjects can include but are not limited to non-human primates, cattle, horses, dogs, cats, guinea pigs, rabbits, rats, and mice.

The terms "treatment," "treating," "treat," and the like refer to obtaining a desired pharmacological and/or physiologic effect in a brain tumor patient. The effect can be prophylactic in terms of completely or partially preventing brain tumor or symptom thereof and/or can be therapeutic in terms of a partial or complete stabilization or cure for brain tumor and/or adverse effect attributable to the brain tumor. Treatment covers any treatment of a brain tumor in a mammal, particularly a human. A desired effect, in particular, is tumor response, which can be measured as reduction of tumor mass or inhibition of tumor mass increase. In addition to tumor response, an increase of overall survival, progress-free survival, or time to tumor recurrence or a reduction of adverse effect also can be used clinically as a desired treatment effect.

(B) Treatments

The present disclosure is reflected in and substantiated by experimental evidence that, in keeping with the inventors' discovery, bacterially derived and intact minicells, which are about 400 nm in diameter, upon intravenous (i.v.) administration accumulate rapidly in the brain tumor microenvironment in therapeutically significant concentrations. The inventors also discovered that this brain tumor penetration does not rely on BBB endothelial endocytosis/transcytosis or on any of the other mechanism by which it has been proposed that nanoparticles enter into the brain tumor microenvironment. From the vantage of conventional knowledge, therefore, these discoveries were quite unexpected.

1. Conventional Knowledge About a Size Limit for Crossing the BBB

Nanoparticles have been considered as potential carriers for taking drugs past the BBB (Juillerat-Jeanneret, 2008). Illustrative in this regard is a nanoparticulate drug delivery strategy aimed at overcoming by binding of nanoparticles to receptors in the lumen of endothelial cells that comprise the BBB, followed by endocytosis and transcytosis across endothelial cells and into the brain tumor microenvironment. Another approach involves exploiting an "enhanced permeation and retention effect," discussed below, to effect passage of particles through tiny gaps between the endothelial cells of the BBB.

2. Transcytosis of Nanoparticles

Poly(butyl cyanoacrylate (PBCA) nanoparticles coated with polysorbate 80 (Tween® 80) were shown to enable brain delivery of a number of drugs that did not cross the BBB in free form (Kreuter et al., 1995, 1997, 2001, 2002, 2003, and 2008; Steiniger et al., 2004).

Since polysorbate 80 selectively promotes adsorption of certain plasma proteins (in particular, apolipoproteins E and B, (Petri et al., 2007; Re et al., 2011) on the surface of these nanoparticles, it enables the binding of these nanoparticles with the respective low-density lipoprotein receptors (LDLr; Xin et al., 2011) which are known to be over-expressed in endothelial blood capillary vessels associated with the BBB (Dehouck et al., 1994).

Post-binding to the LDLr, the nanoparticles are internalized by the blood vessel endothelial cells (Zensi et al., 2009), transcytosed across these cells and then transported into the brain tumor microenvironment.

A worldwide effort to develop nanoparticles for treating brain tumors is focused on finding innovative ways to traverse the BBB by transcytosing the BBB-associated endothelial cells and entering into the brain tumor microenvironment. This is a major challenge by virtue of the fact that these particles must remain intact during the transcytosic intracellular movement and not be degraded by lysosomes. The latter are highly acidic intracellular compartments, which normally degrade endocytosed materials.

An additional serious drawback of this approach is the fact that the LDLr is not unique to the BBB. It is only over-expressed in the endothelial cells associated with the BBB. Therefore, these nanoparticles have the potential to enter into a large number of normal tissues and the normal central nervous system since these receptors are ubiquitously located in endothelial cells throughout the circulatory system. So far, receptors have not been found that are unique only to the BBB associated blood vessels and hence the potential for serious toxicity to normal tissues remains a concern.

3. Passive Entry into Brain Tumors

Recent evidence has indicated that the physiologic upper limit of pore size in the BBB of malignant glioma microvasculature is only about 12 nm (Sarin et al., 2008). Further, it has been shown that molecules would need to be as small as <400 Daltons (Bickel, 2005; Pardridge, 2007) to be able to cross the pores found in the BBB.

The sizing constraints are widely accepted among researchers and clinicians in the field. For instance, a review of the recent literature concluded that nanoparticles need to be smaller than 12 nm and have long blood half-lives to cross the BBB of malignant glioma microvasculature (Laquintana et al., 2009).

A variety of nanoparticles have been studied in this regard, including liposomes, polymeric nanoparticles, solid lipid nanoparticles, polymeric micelles, and dendrimers. Following intravenous administration, these particles can extravasate into brain tumor, because of the disrupted BBB of brain tumor vessels, but also to a lesser extent into normal brain tissue as well (Moghimi et al., 2005).

This passive targeting of nanoparticles in brain tumors with disrupted BBB generally is linked to the above-mentioned enhanced permeability and retention (EPR) effect, which is deemed to play a critical role in drug delivery to solid tumors. For instance, Laquintana et al. (2009) reflects the current view that liposomes, which typically range between 50 to 150 nm, remain within the microvasculature, whereby encapsulated small chemotherapy drugs diffuse across the liposome membrane and across the pores with the BBB of malignant gliomas. Thus, larger particles (50 to 150 nm) are not thought to be able to extravasate through the BBB via disruptions in the barrier.

The conventional understanding therefore is that, in order to cross the BBB passively via the EPR effect and to reach pharmacologically significant amounts in the brain tumor microenvironment, nanoparticles should be <12 nm in size and macromolecules such as drugs should have a molecular weight of <400 Daltons. This understanding is underscored in a review article by Pardridge (2010), which emphasizes that the "single most important factor in brain drug development is the availability of an effective brain drug targeting technology."

This is because the majority of candidate drugs for the central nervous system (CNS) do not cross the blood-brain barrier (BBB). Biopharmaceuticals, which are large molecule drugs, do not cross the BBB. Therefore, in the absence of brain targeting technology, recombinant proteins, monoclonal antibodies, peptides, short interfering RNA (siRNA), and gene therapeutics cannot be developed for the brain, because these drugs do not cross the BBB. With respect to small molecules, it is generally assumed that these agents do cross the BBB. However, >98% of all small molecules do not cross the BBB (Pardridge et al., 2005). Only lipid soluble small molecules with a molecular weight (MW)<400 Daltons (Da) cross the BBB via lipid-mediation. However, the majority of small molecule drugs either have a MW >400 Da, or have high water solubility, which prevents free diffusion through the BBB. Therefore, even if the CNS drug developer is focused on small molecules, it is likely that a BBB drug targeting technology will still be required for successful completion of the CNS small molecule drug development program for most drugs.

4. Additional Barriers to Brain Tumor Entry

Besides the BBB, brain uptake is further restricted by a relative paucity of fenestrae and pinocytotic vesicles within the brain capillary endothelial cells, as well as by the presence of the surrounding extracellular matrix, pericytes, and astrocyte foot processes (Hawkins and Davis, 2005). Additionally, the BBB conventionally is deemed impregnable to drugs and macromolecules by virtue of numerous drug transport proteins, which move drugs out of the brain.

For example, it has been shown that ATP-dependent transporters can severely restrict the brain penetration of therapeutic agents, even those with favorable physicochemical properties that were predicted to cross the BBB with relative ease. Most of these transporters belong to two superfamilies, the ATP-binding cassette (ABC) and solute carrier families. P-glycoprotein (P-gp, ABCB1), breast-cancer-resistance protein (BCRP, ABCG2), and multidrug resistance associated proteins (MRPs, ABCCs) are important members of the ABC family. See Schinkel (1999), Borst et al. (2000), Sun et al. (2003), Schinkel and Jonker (2003), Kusuhara and Sugiyama (2005), Loscher and Potschka (2005), and Nicolazzo and Katneni (2009).

Accordingly, the present inventors found it truly surprising that intact, bacterially derived minicells accumulate in brain tumors, despite the fact that the minicells are considerably larger (~400 nm) than the consensus upper size limit (<12 nm) for nanoparticles to enter into brain tumors. Also unexpected was the finding that minicells enter the brain passively, via disrupted BBB. In this regard the inventors made the surprising observation that blood vessels associated with brain tumors are not only of the BBB-type. Even at an early stage, a growing tumor, it was found, has many blood vessels, particularly at its core. Such blood vessels display a loss of integrity; that is, the vessels have large fenestrations and are "leaky," unlike BBB-type vessels. In contravention of conventional understanding, therefore, particles that are as large as minicells, i.e., much larger than the above-discussed consensus pore size limitations of the BBB, nevertheless are smaller than the fenestrations in the walls of the leaky blood vessel; hence, they can extravasate passively through these fenestrations and into the brain tumor microenvironment.

Moreover, the inventors found that the relatively large size of intact, bacterially derived minicells actually is a positive, even key factor in how rapidly therapeutically significant minicells concentrations are achieved in the brain tumor microenvironment, pursuant to the finding. The smaller the particle, that is, the more likely it is that the particle will be restrained by blood flow in blood vessels. By contrast, minicells are particles of a relatively larger mass, and they therefore are less affected by the force exerted by blood flow. Consequently, minicells are more likely to follow a path through blood capillaries that results in repeated collision against the endothelial walls of blood capillaries. This purely physical phenomenon increases the likelihood that minicells, as larger particles, are pushed through the fenestrations in leaky vasculature that, as the inventors discovered, is the hallmark of the disrupted BBB in tumors.

There are more than 100 billion capillaries in the human brain, presenting a total length of approximately 400 miles, and yet the intra-endothelial volume of these capillaries is only about 1 μL/g brain (Pardridge, 2011). This very high density of blood vessels in the brain is believed also to contribute to the rapid, high-concentration accumulation of minicells in brain tumors, according to the finding.

Recognizing that the diameter of the capillary lumen associated with the BBB thus can be as small as 1 μm, the inventors had the insight that particles as large as intact, bacterially derived minicells (~400 nm) would be about half the diameter of BBB-associated blood capillary vessels and therefore would extravasate rapidly from disrupted BBB, where gaps are greater than 400 nm in size. On the other hand, because fenestrations in the normal vasculature of the mammalian body do not exceed about 100 μm in size, intact, bacterially derived minicells that are introduced systemically, pursuant to the finding, are retained in the general vascular system until they are scavenged up by professional phagocytic cells in the reticuloendothelial system or until they passively extravasate from the leaky vasculature into the brain tumor microenvironment.

Accordingly, when two types of nanoparticles i.v. administered in equal numbers, e.g., nanoparticles of less than 12 nm in diameter and intact, bacterially derived minicells, then one would expect that the circulating concentration of the smaller particles would decrease rapidly, since they would In the context of this disclosure, selecting an anti-neoplastic agent for treating a given brain tumor patient depends on several factors, in keeping with conventional medical practice. These factors include but are not limited to the patient's age, Karnofsky Score, and whatever previous therapy the patient may have received. See, generally, PRINCIPLES AND PRACTICE OF NEURO-ONCOLOGY, M. Mehta (Demos Medical Publishing 2011), and PRINCIPLES OF NEURO-ONCOLOGY, D. Schiff and P. O'Neill, eds. (McGraw-Hill 2005).

More generally, the standard of care applicable to a given brain cancer recommends, in the first instance, the clinical considerations that should inform the choice of active agent to use. This perspective would guide the selection, for example, of an active agent from a list, reproduced below in Table 1, which the University of California at Los Angeles has published of anti-neoplastic agents that are suitable for treating brain tumors.

TABLE 1

Known anti-neoplastic agents for treating brain tumors

| | | |
|---|---|---|
| 5FC | Accutane Hoffmann-La Roche | AEE788 Novartis |
| AMG-102 | Anti Neoplaston | AQ4N (Banoxantrone) |
| AVANDIA (Rosiglitazone Maleate) | Avastin (Bevacizumab) Genetech | BCNU |
| BiCNU Carmustine | Carboplatin | CCI-779 |
| CCNU | CCNU Lomustine | Celecoxib (Systemic) |
| Chloroquine | Cilengitide (EMD 121974) | Cisplatin |
| CPT -11 (CAMPTOSAR, Irinotecan) | Cytoxan | Dasatinib (BMS-354825, Sprycel) |
| Dendritic Cell Therapy | Etoposide (Eposin, Etopophos, Vepesid) | GDC-0449 |
| Gleevec (imatinib mesylate) | GLIADEL Wafer | Hydroxychloroquine |
| Hydroxyurea | IL-13 | IMC-3G3 |
| Immune Therapy | Iressa (ZD-1839) | Lapatinib (GW572016) |
| Methotrexate for Cancer (Systemic) | Novocure | OSI-774 |
| PCV | Procarbazine | RAD001 Novartis (mTOR inhibitor) |
| Rapamycin (Rapamune, Sirolimus) | RMP-7 | RTA 744 |
| Simvastatin | Sirolimus | Sorafenib |
| SU-101 | SU5416 Sugen | Sulfasalazine (Azulfidine) |
| Sutent (Pfizer) | Tamoxifen | TARCEVA (erlotinib HCl) |
| Taxol | TEMODAR Schering-Plough | TGF-B Anti-Sense |
| Thalomid (thalidomide) | Topotecan (Systemic) | VEGF Trap |
| VEGF-Trap | Vincristine | Vorinostat (SAHA) |
| XL 765 | XL184 | XL765 |
| Zarnestra (tipifarnib) | ZOCOR (simvastatin) | | extravasate out of the blood circulation in normal tissues, where the vasculature has pores larger than 12 nm. It is known, for instance, that liver and gastrointestinal tissue has normal vasculature fenestrations of about 100 nm (Wisse et al., 2008), and the peripheral skin has fenestrations in the range of ~40 nm. By contrast, the minicells would be too large to fall out of the normal vasculature; hence, they would be expected to stay in high concentration in the normal blood circulation, whereby greater numbers would extravasate into the brain tumor microenvironment, as described above.

In accordance with one embodiment, therefore, the present disclosure provides a treatment for a brain tumor that entails administering a therapeutically effective amount of a composition comprised of a plurality of intact, bacterially derived minicells carrying an anti-neoplastic agent. The administration of the minicell-containing composition preferably is systemic, e.g., intravenous or intra-arterial.

(C) Anti-Neoplastic Agents

As noted, the minicell compositions of the present disclosure are useful in delivering anti-neoplastic agents to the brain tumors. In this context, the phrase "anti-neoplastic agent" denotes a drug, whether chemical or biological, that prevents or inhibits the growth, development, maturation, or spread of neoplastic cells.

In accordance with the disclosure, a drug also can be selected from one of the classes detailed below, for packaging into intact, bacterially derived minicells, which then are administered to treat a brain cancer.

Polyfunctional alkylating agents, exemplified by Cyclophosphamide (Cytoxan), Mechlorethamine, Melphalan (Alkeran), Chlorambucil (Leukeran), Thiopeta (Thioplex), Busulfan (Myleran).

Alkylating drugs, exemplified by Procarbazine (Matulane), Dacarbazine (DTIC), Altretamine (Hexalen), Clorambucil, Cisplatin (Platinol), Carboplatin, Ifosafamide, Oxaliplatin.

Antimetabolites, exemplified by Methotrexate (MTX), 6-Thiopurines (Mercaptopurine [6-MP], Thioguanine [6-TG]), Mercaptopurine (Purinethol), Thioguanine, Fludarabine phosphate, Cladribine: (Leustatin), Pentostatin, Flurouracil (5-FU), Cytarabine (ara-C), Azacitidine.

Plant alkaloids, terpenoids and topoisomerase inhibitors, exemplified by Vinblastine (Velban), Vincristine (Oncovin), Vindesine, Vinorelbine, Podophyllotoxins (etoposide {VP-16} and teniposide {VM-26}), Campthothecins (topotecan and irinotecan), Taxanes such as Paclitaxel (Taxol) and Docetaxel (Taxotere).

Antibiotics, exemplified by Doxorubicin (Adriamycin, Rubex, Doxil), Daunorubicin, Idarubicin, Dactinomycin (Cosmegen), Plicamycin (Mithramycin), Mitomycin: (Mutamycin), Bleomycin (Blenoxane).

Hormonal agents, exemplified by Estrogen and Androgen Inhibitors (Tamoxifen and Flutamide), Gonadotropin-Releasing Hormone Agonists (Leuprolide and Goserelin (Zoladex)), Aromatase Inhibitors (Aminoglutethimide and Anastrozole (Arimidex)).

Miscellaneous Anticancer Drugs, exemplified by Amsacrine, Asparaginase (El-spar), Hydroxyurea, Mitoxantrone (Novantrone), Mitotane (Lysodren), Retinoic acid Derivatives, Bone Marrow Growth Factors (sargramostim and filgrastim), Amifostine.

Agents disrupting folate metabolism, e.g., Pemetrexed.

DNA hypomethylating agents, e.g., Azacitidine, Decitabine.

Poly(adenosine diphosphate [ADP]-ribose) polymerase (PARP) pathway inhibitors, such as Iniparib, Olaparib, Veliparib.

PI3K/Akt/mTOR pathway inhibitors, e.g., Everolimus.

Histone deacetylase (HDAC) inhibitors, e.g., Vorinostat, Entinostat (SNDX-275), Mocetinostat (MGCD0103), Panobinostat (LBH589), Romidepsin, Valproic acid.

Cyclin-dependent kinase (CDK) inhibitors, e.g., Flavopiridol, Olomoucine, Roscovitine, Kenpaullone, AG-024322 (Pfizer), Fascaplysin, Ryuvidine, Purvalanol A, NU2058, B1VIL-259, SU 9516, PD-0332991, P276-00.

Heat shock protein (HSP90) inhibitors, e.g., Geldanamycin, Tanespimycin, Alvespimycin, Radicicol, Deguelin, BIIB021.

Murine double minute 2 (MDM2) inhibitors, e.g., Cis-imidazoline, Benzodiazepinedione, Spiro-oxindoles, Isoquinolinone, Thiophene, 5-Deazaflavin, Tryptamine.

Anaplastic lymphoma kinase (ALK) inhibitors, e.g., Aminopyridine, Diaminopyrimidine, Pyridoisoquinoline, Pyrrolopyrazole, Indolocarbazole, Pyrrolopyrimidine, Dianilinopyrimidine.

Poly [ADPribose] polymerase (PARP) inhibitors, illustrated by Benzamide, Phthalazinone, Tricyclic indole, Benzimidazole, Indazole, Pyrrolocarbazole, Phthalazinone, Isoindolinone.

Active agents useable in the present disclosure are not limited to those drug classes or particular agents enumerated above. Different discovery platforms continue to yield new agents that are directed at unique molecular signatures of cancer cells; indeed, thousands of such chemical and biological drugs have been discovered, only some of which are listed here. Yet, the surprising capability of intact, bacterially derived minicells to accommodate packaging of a diverse variety of active agents, hydrophilic or hydrophobic, means that essentially any such drug, when packaged in minicells, has the potential to treat a brain cancer, pursuant to the findings in the present disclosure.

In principle, the potential suitability of a given anti-neoplastic agent for treating a brain tumor is partly a function of whether the agent can be delivered effectively into the brain. With the benefit of the present findings, whereby drug-loaded minicells traverse the BBB and deliver a drug payload into a brain tumor specifically, many drugs that otherwise would not have proven efficacious in treating a brain tumor now will be viable candidates for such treatment. Accordingly, in this description the "anti-neoplastic agent" rubric is not limited to drugs of known efficacy for brain cancer therapy, but also rather it encompasses agents that are determined to have one or more of the aforementioned activities against neoplastic cells.

Likewise illustrative of the class of anti-neoplastic agents are radionuclides, chemotherapy drugs, and functional nucleic acids, including but not limited to regulatory RNAs.

1. Radionuclides

A "radionuclide" is an atom with an unstable nucleus, i.e., one characterized by excess energy available to be imparted either to a newly created radiation particle within the nucleus or to an atomic electron. Therefore, a radionuclide undergoes radioactive decay, and emits gamma ray(s) and/or subatomic particles. Numerous radionuclides are known in the art, and a number of them are known to be suitable for medical use, such as yttrium-90, technetium-99m, iodine-123, iodine-131, rubidium-82, thallium-201, gallium-67, fluorine-18, xenon-133, and indium-111.

Radionuclides have found extensive use in nuclear medicine, particularly as beta-ray emitters for damaging tumor cells. Radionuclides are suitably employed, therefore, as anti-neoplastic agents in the present disclosure.

Radionuclides can be associated with intact, bacterially derived minicells by any known technique. Thus, a protein or other minicell-surface moiety (see below) can be labeled with a radionuclide, using a commercially available labeling means, such as use of Pierce Iodination reagent, a product of Pierce Biotechnology Inc. (Rockford, IL), detailed in Rice et al. (2011). Alternatively, radionuclides can be incorporated into proteins that are inside minicells.

In the latter situation, a minicell-producing bacterial strain is transformed with plasmid DNA encoding foreign protein. When minicells are formed during asymmetric cell division, several copies of the plasmid DNA segregates into the minicell cytoplasm. The resultant, recombinant minicells are incubated, in the presence of radiolabeled amino acids, under conditions such that foreign protein expressed inside the minicell, from the plasmid DNA, incorporates the radionuclide-carrying amino acids. Pursuant to the protocol of Clark-Curtiss and Curtiss (1983), for instance, recombinant minicells are incubated in minimal growth medium that contains 35 S-methionine, whereby newly expressed, plasmid-encoded proteins incorporate the 35 S-methionine. A similar approach can be used in order that recombinant minicells become packaged with other radiolabels, as desired.

Oligosaccharides on the minicell surface also can be radiolabeled using, for example, well-established protocols described by Fukuda (1994). Illustrative of such oligosaccharides that are endemic to minicells is the 0-polysaccharide component of the lipopolysaccharide (LPS) found on the surface of minicells derived from Gram-negative bacteria (see below).

A preferred methodology in this regard is to radiolabel a bispecific antibody that is used to target minicells to specific tumors. See section G, infra, and patent publication US 2007/0237744, the contents of which are incorporated herein by reference. That is, the bispecific antibody "coated" on a minicell exposes a significant amount of additional surface protein for radiolabeling. Accordingly, it is possible to achieve a higher specific activity of the radiolabel associated with the antibody-coated minicell. By contrast, the radiolabeling of non-coated minicells, i.e., when the radionuclide labels only endemic moieties, can result in weaker labeling (lower specific activity). In one embodiment, this weaker labeling is thought to occur because the outer membrane-associated proteins of minicells derived from Gram-negative bacteria are masked by LPS, which, as further discussed below, comprises long chains of 0-polysaccharide covering the minicell surface.

For treating a brain tumor, a composition of the disclosure would be delivered in a dose or in multiple doses that in toto affords a level of in-tumor irradiation that is sufficient at least to reduce tumor mass, if not eliminate the tumor altogether. The progress of treatment can be monitored along this line, on a case-by-case basis. In general terms, however, the amount of radioactivity packaged in the composition typically will be on the order of about to 50 Gy, although the invention also contemplates a higher amount of radioactivity, say, about 50 to 100 Gy, which gives an overall range between about 30 Gy and about 100 Gy.

In some instances the amount of radioactivity packaged in the composition can be even lower than mentioned above, given the highly efficient and specific delivery of the minicell-born radionuclides to a brain tumor. Accordingly, in one aspect the composition contains from about 20 to 40 Gy, or about 10 to 30 Gy, or about 1 to about 20 Gy, or less than 10 Gy.

2. Chemotherapy Drugs

An anti-neoplastic agent employed in the present disclosure also can be a chemotherapy drug. In this description, "chemotherapeutic drug," "chemotherapeutic agent," and "chemotherapy" are employed interchangeably to connote a drug that has the ability to kill or disrupt a neoplastic cell. A chemotherapeutic agent can be a small molecule drug or a biologic drug, as further detailed below.

The "small molecule drug" subcategory encompasses organic compounds characterized by having (i) an effect on a biological process and (ii) a relatively low molecular weight, compared to a macromolecule. Small molecule drugs typically are about 800 Daltons or less, where "about" indicates that the qualified molecular-weight value is subject to variances in measurement precision and to experimental error on the order of several Daltons or tens of Daltons. Thus, a small molecule drug can have a molecular weight of about 900 Daltons or less, about 800 or less, about 700 or less, about 600 or less, about 500 or less, or about 400 Daltons or less. More specifically, a small molecule chemotherapy drug can have a molecular weight of about 400 Daltons or more, about 450 Daltons or more, about 500 Daltons or more, about 550 Daltons or more, about 600 Daltons or more, about 650 Daltons or more, about 700 Daltons or more, or about 750 Daltons or more. In another embodiment, the small molecule chemotherapy drug packaged into the minicells has a molecular weight between about 400 and about 900 Daltons, between about 450 and about 900 Daltons, between about 450 and about 850 Daltons, between about 450 and about 800 Daltons, between about 500 and about 800 Daltons, or between about 550 and about 750 Daltons.

For purposes of this description a "biologic drug" is defined, by contrast, to denote any biologically active macromolecule that can be created by a biological process, exclusive of "functional nucleic acids," discussed below, and polypeptides that by size qualify as small molecule drugs, as defined above. The "biologic drug" subcategory thus is exclusive of and does not overlap with the small molecule drug and functional nucleic acid subcategories. Illustrative of biologic drugs are therapeutic proteins and antibodies, whether natural or recombinant or synthetically made, e.g., using the tools of medicinal chemistry and drug design.

It was widely understood heretofore that molecules larger than 400 Daltons would be unable to cross the pores found in the BBB (Bickel, 2005; Pardridge, 2007); hence, that they would be unsuitable for treating brain tumors. When packaged into minicells, however, such chemotherapy drugs reaching targeted brain tumor cells, bypassing the BBB.

Whether a small molecular drug or a biologic drug, moreover, certain molecules that are designed for chemotherapeutic purposes nevertheless fail during pre-clinical or clinical trials due to unacceptable toxicity or other safety concerns. The present inventors have shown that packaging a chemotherapy drug in a minicell, followed by systemic delivery to a tumor patient, such as a brain tumor patient, results in delivery of the drug to tumor cells. Further, even after the tumor cells are broken up and the drug-containing cytoplasm is released to the nearby normal tissue, the result is not toxicity to normal tissue. This is because the drug is already bound to the tumor cellular structures, such as DNA, and can no longer attack normal cells. Accordingly, the present invention is particularly useful for delivery of highly toxic chemotherapy drugs to a tumor patient.

The phrases "highly toxic chemotherapy drug" or "supertoxic chemotherapy drug" in this description refer to chemotherapy drugs that have a relative low lethal dose as compared to their effective dose for a targeted cancer. Thus, in one aspect a highly toxic chemotherapy drug has a median lethal dose ($LD_{50}$) that is lower than its median effective dose ($ED_{50}$) for a targeted cancer such as (1) a cancer type for which the drug is designed, (2) the first cancer type in which a pre-clinical or clinical trial is run for that drug, or (3) the cancer type in which the drug shows the highest efficacy among all tested cancers. For instance, a highly toxic chemotherapy drug can have an $LD_{50}$ that is lower than about 500%, 400%, 300%, 250%, 200%, 150%, 120%, or 100% of the $ED_{50}$ of the drug for a targeted cancer. In another aspect, a highly toxic chemotherapy drug has a maximum sub-lethal dose (i.e., the highest dose that does not cause serious or irreversible toxicity) that is lower than its minimum effective dose for a targeted cancer, e.g., about 500%, 400%, 300%, 250%, 200%, 150%, 120%, 100%, 90%, 80%, 70%, 60% or 50% of the minimum effective dose.

According to one embodiment of the present description, therefore, a brain tumor in a subject is treated by a method comprising administering systemically a therapeutically effective amount of a composition comprised of a plurality of intact, bacterially derived minicells, each of which encompasses a highly toxic chemotherapy drug. Maytansinoids and duocarmycins, discussed below, are representative of the class of supertoxic chemotherapy drugs thus employed.

Suitable cancer chemotherapy drugs in the context include nitrogen mustards, nitrosorueas, ethyleneimine, alkane sulfonates, tetrazine, platinum compounds, pyrimidine analogs, purine analogs, antimetabolites, folate analogs, anthracyclines, taxanes, vinca alkaloids, topoisomerase inhibitors, and hormonal agents, inter alia.

Chemotherapy drugs that are illustrative of the small molecule drug subcategory are Actinomycin-D, Alkeran, Ara-C, Anastrozole, BiCNU, Bicalutamide, Bleomycin, Busulfan, Capecitabine, Carboplatin, Carboplatinum, Carmustine, CCNU, Chlorambucil, Cisplatin, Cladribine, CPT-11, Cyclophosphamide, Cytarabine, Cytosine arabinoside, Cytoxan, Dacarbazine, Dactinomycin, Daunorubicin, Dexrazoxane, Docetaxel, Doxorubicin, DTIC, Epirubicin, Ethyleneimine, Etoposide, Floxuridine, Fludarabine, Fluorouracil, Flutamide, Fotemustine, Gemcitabine, Hexamethylamine, Hydroxyurea, Idarubicin, Ifosfamide, Irinotecan, Lomustine, Mechlorethamine, Melphalan, Mercaptopurine, Methotrexate, Mitomycin, Mitotane, Mitoxantrone, Oxaliplatin, Paclitaxel, Pamidronate, Pentostatin, Plicamycin, Procarbazine, Steroids, Streptozocin, STI-571, Streptozocin, Tamoxifen, Temozolomide, Teniposide, Tetrazine, Thioguanine, Thiotepa, Tomudex, Topotecan, Treosulphan, Trimetrexate, Vinblastine, Vincristine, Vindesine, Vinorelbine, VP-16, and Xeloda.

Maytansinoids (molecular weight: ~738 Daltons) are a group of chemical derivatives of maytansine, having potent cytotoxicity. Although considered unsafe for human patient use, due to toxicity concerns, maytansinoids are suitable for delivery to brain tumor patients via minicells, pursuant to the present invention.

Duocarmycins (molecular weight: ~588 Daltons) are a series of related natural products, first isolated from Streptomyces bacteria. They also have potent cytotoxicity but are considered as unsafe for human use. Like maytansinoids, duocarmycins are suitable chemotherapy drugs for use in the invention.

The subcategory of biologic chemotherapy drugs includes, without limitation, Asparaginase, AIN-457, Bapineuzumab, Belimumab, Brentuximab, Briakinumab, Canakinumab, Cetuximab, Dalotuzumab, Denosumab, Epratuzumab, Estafenatox, Farletuzumab, Figitumumab, Galiximab, Gemtuzumab, Girentuximab (WX-G250), Herceptin, Ibritumomab, Inotuzumab, Ipilimumab, Mepolizumab, Muromonab-CD3, Naptumomab, Necitumumab, Nimotuzumab, Ocrelizumab, Ofatumumab, Otelixizumab, Ozogamicin, Pagibaximab, Panitumumab, Pertuzumab, Ramucirumab, Reslizumab, Rituximab, REGN88, Solanezumab, Tanezumab, Teplizumab, Tiuxetan, Tositumomab, Trastuzumab, Tremelimumab, Vedolizumab, Zalutumumab, and Zanolimumab.

The composition can contain at most about 1 mg of the chemotherapeutic drug. Alternatively, the amount of the chemotherapeutic drug can be at most about 750 µg, 500 µg, 250 µg, 100 µg, 50 µg, 10 µg, 5 µg, 1 µg, 0.5 µg, or 0.1 µg. In another aspect, the composition contains a chemotherapeutic drug having an amount of less than about 1/1,000, or alternatively less than about 1/2,000, 1/5,000, 1/10,000, 1/20,000, 1/50,000, 1/100,000, 1/200,000 or 1/500,000 of the therapeutically effective amount of the drug when used without being packaged to into minicells. Pursuant to yet another aspect of the disclosure, the composition can contain at least about 1 nmol of the chemotherapeutic drug. Accordingly, the disclosure also encompasses embodiments where the amount of the chemotherapeutic drug is at least about 2 nmol, about 3 nmol, about 4 nmol, about 5 nmol, about 10 nmol, about 20 nmol, about 50 nmol, about 100 nmol, and about 800 nmol, respectively. 3. Functional Nucleic Acids "Functional nucleic acid" refers to a nucleic acid molecule that, upon introduction into a host cell, specifically interferes with expression of a protein. With respect to treating a brain tumor, in accordance with the disclosure, it is preferable that a functional nucleic acid payload delivered to tumor cells via intact, bacterially derived minicells inhibits a gene that promotes tumor cell proliferation, angiogenesis or resistance to chemotherapy and/or that inhibits apoptosis or cell-cycle arrest (i.e., a "tumor-promoting gene").

It is generally the case that functional nucleic acid molecules used in this disclosure have the capacity to reduce expression of a protein by interacting with a transcript for a protein. This category of minicell payload for the disclosure includes regulatory RNAs, such as siRNA, shRNA, short RNAs (typically less than 400 bases in length), micro-RNAs (miRNAs), ribozymes and decoy RNA, antisense nucleic acids, and LincRNA, inter alia. In this regard, "ribozyme" refers to an RNA molecule having an enzymatic activity that can repeatedly cleave other RNA molecules in a nucleotide base sequence-specific manner. "Antisense oligonucleotide" denotes a nucleic acid molecule that is complementary to a portion of a particular gene transcript, such that the molecule can hybridize to the transcript and block its translation. An antisense oligonucleotide can comprise RNA or DNA. The "LincRNA" or "long intergenic non-coding RNA" rubric encompasses non-protein coding transcripts longer than 200 nucleotides. LincRNAs can regulate the transcription, splicing, and/or translation of genes, as discussed by Khalil et al., *Proc Nat'l Acad. USA* 106: 11667-72 (2009), for instance.

Each of the types of regulatory RNA can be the source of functional nucleic acid molecule that inhibits a tumor-promoting gene as described above and, hence, that is suitable for use according to the present disclosure. Thus, in one preferred embodiment of the disclosure the intact minicells carry siRNA molecules mediating a post-transcriptional, gene-silencing RNA interference (RNAi) mechanism, which can be exploited to target tumor-promoting genes. For example, see MacDiarmid et al., *Nature Biotech.* 27: 645-51 (2009) (antibody-presenting minicells deliver, with chemotherapy drug, siRNAs that counter developing resistance to drug), and Oh and Park, *Advanced Drug Delivery Rev.* 61: 850-62 (2009) (delivery of therapeutic siRNAs to treat breast, ovarian, cervical, liver, lung and prostate cancer, respectively).

As noted, "siRNA" generally refers to double-stranded RNA molecules from about 10 to about 30 nucleotides long that are named for their ability specifically to interfere with protein expression. Preferably, siRNA molecules are 12-28 nucleotides long, more preferably 15-25 nucleotides long, still more preferably 19-23 nucleotides long and most preferably 21-23 nucleotides long. Therefore, siRNA molecules can be 12, 13, 14, 15, 16, 17, 18, 19, 20, 21, 22, 23, 24, 25, 26, 27 28 or 29 nucleotides in length.

The length of one strand designates the length of an siRNA molecule. For instance, an siRNA that is described as 21 ribonucleotides long (a 21-mer) could comprise two opposing strands of RNA that anneal for 19 contiguous base pairings. The two remaining ribonucleotides on each strand would form an "overhang." When an siRNA contains two strands of different lengths, the longer of the strands designates the length of the siRNA. For instance, a dsRNA containing one strand that is 21 nucleotides long and a second strand that is 20 nucleotides long, constitutes a 21-mer.

Tools to assist the design of siRNA specifically and regulatory RNA generally are readily available. For instance, a computer-based siRNA design tool is available on the internet at www.dharmacon.com.

In another preferred embodiment, the intact minicells of the present disclosure carry miRNAs, which, like siRNA, are capable of mediating a post-transcriptional, gene-silencing RNA interference (RNAi) mechanism. Also like siRNA, the gene-silencing effect mediated by miRNA can be exploited to target tumor-promoting genes. For example, see Kota et al., *Cell* 137: 1005-17 (2009) (delivery of a miRNA via transfection resulted in inhibition of cancer cell proliferation, tumor-specific apoptosis and dramatic protection from disease progression without toxicity in murine liver cancer model), and Takeshita, et al., *Molec. Ther.* 18: 181-87 (2010) (delivery of synthetic miRNA via transient transfection inhibited growth of metastatic prostate tumor cells on bone tissues).

Although both mediate RNA interference, miRNA and siRNA have noted differences. In this regard, "miRNA" generally refers to a class of 17- to 27-nucleotide singlestranded RNA molecules (instead of double-stranded as in the case of siRNA). Therefore, miRNA molecules can be 17, 18, 19, 20, 21, 22, 23, 24, 25, 26, 27 nucleotides in length. Preferably, miRNA molecules are 21-25 nucleotide long.

Another difference between miRNAs and siRNAs is that the former generally do not fully complement the mRNA target. On the other hand, siRNA must be completely complementary to the mRNA target. Consequently, siRNA generally results in silencing of a single, specific target, while miRNA is promiscuous.

Additionally, although both are assembled into RISC (RNA-induced silencing complex), siRNA and miRNA differ in their respective initial processing before RISC assembly. These differences are described in detail in Chu et al., *PLoS Biology* 4: 1122-36 (2006), and Gregory et al., *Methods in Molecular Biology* 342: 33-47 (2006).

A number of databases serve as miRNA depositories. For example, see miRBase (www.mirbase.org) and tarbase (http://diana.cslab.ece.ntua.gr/DianaToolsNew/index.php?r=tarbase/index). In conventional usage, miRNAs typically are named with the prefix "-mir," combined with a sequential number. For instance, a new miRNA discovered after mouse mir-352 will be named mouse mir-353.

Again, tools to assist the design of regulatory RNA including miRNA are readily available. In this regard, a computer-based miRNA design tool is available on the internet at wmd2.weigelworld.org/cgi-bin/mirnatools.pl.

As noted above, a functional nucleic acid employed in the disclosure can inhibit a gene that promotes tumor cell proliferation, angiogenesis or resistance to chemotherapy. The inhibited gene also can itself inhibit apoptosis or cell cycle arrest. Examples of genes that can be targeted by a functional nucleic acid are provided below.

Functional nucleic acids of the disclosure preferably target the gene or transcript of a protein that promotes drug resistance, inhibits apoptosis or promotes a neoplastic phenotype. Successful application of functional nucleic acid strategies in these contexts have been achieved in the art, but without the benefits of minicell vectors. See, e.g., Sioud (2004), Caplen (2003), Nieth et al. (2003), Caplen and Mousses (2003), Duxbury et al. (2004), Yague et al. (2004), and Duan et al. (2004).

Proteins that contribute to drug resistance constitute preferred targets of functional nucleic acids. The proteins may contribute to acquired drug resistance or intrinsic drug resistance. When diseased cells, such as tumor cells, initially respond to drugs, but become refractory on subsequent treatment cycles, the resistant phenotype is acquired. Useful targets involved in acquired drug resistance include ATP binding cassette transporters such as P-glycoprotein (P-gp, P-170, PGY1, MDR1, ABCB1, MDR-associated protein, Multidrug resistance protein 1), MDR-2 and MDR-3. MRP2 (multi-drug resistance associated protein), BCR-ABL (breakpoint cluster region—Abelson protooncogene), a STI-571 resistance-associated protein, lung resistance-related protein, cyclooxygenase-2, nuclear factor kappa, XRCC1 (X-ray cross-complementing group 1), ERCC1 (Excision cross-complementing gene), GSTP1 (Glutathione S-transferase), mutant β-tubulin, and growth factors such as IL-6 are additional targets involved in acquired drug resistance.

Particularly useful targets that contribute to drug resistance include ATP binding cassette transporters such as P-glycoprotein, MDR-2, MDR-3, BCRP, APT11a, and LRP.

Useful targets also include proteins that promote apoptosis resistance. These include Bcl-2 (B cell leukemia/lymphoma), Bcl-XL, Al/Bfl 1, focal adhesion kinase, dihydrodiol dehydrogenase, and p53 mutant protein.

Useful targets further include oncogenic and mutant tumor suppressor proteins. Illustrative of these are β-Catenin, PKC-α (protein kinase C), C-RAF, K-Ras (V12), DP97 Dead box RNA helicase, DNMT1 (DNA methyltransferase 1), FLIP (Flice-like inhibitory protein), C-Sfc, 53BPI, Polycomb group protein EZH2 (Enhancer of zeste homologue), ErbB 1, HPV-16 E5 and E7 (human papillomavirus early 5 and early 7), Fortilin & MCI1P (Myeloid cell leukemia 1 protein), DIP13α (DDC interacting protein 13a), MBD2 (Methyl CpG binding domain), p21, KLF4 (Kruppel-like factor 4), tpt/TCTP (Translational controlled tumor protein), SPK1 and SPK2 (Sphingosine kinase), P300, PLK1 (Polo-like kinase-1), Trp53, Ras, ErbB1, VEGF (Vascular endothelial growth factor), BAG-1 (BCL2-associated athanogene 1), MRP2, BCR-ABL, STI-571 resistance-associated protein, lung resistance-related protein, cyclooxygenase-2, nuclear factor kappa, XRCC1, ERCC1, GSTP1, mutant β-tubulin, and growth factors.

Also useful as targets are global regulatory elements exemplified by the cytoplasmic polyadenylation element binding proteins (CEPBs). For instance, CEPB4 is overexpressed in glioblastoma and pancreatic cancers, where the protein activates hundreds of genes associated with tumor growth, and it is not detected in healthy cells (Oritz-Zapater et al., 2011). In accordance with the present description, therefore, treatment of a glioblastoma could be effected via administration of a composition containing intact, bacterially derived minicells that encompass an agent that counters overexpression of CEPB4, such as an siRNA or other functional nucleic acid molecule that disrupts CEPB4 expression by the brain tumor cells.

(D) Brain Tumors

The fact that loss of vascular integrity, as detailed above, is characteristic of all types and stages of brain tumors means that methodology in accordance with the present disclosure can be adapted for use in treating any brain tumor. In this regard, "brain tumor" connotes a solid neoplasm that is intracranial or in the central spinal canal.

There are more than 120 types of brain tumors. Most medical institutions use the World Health Organization (WHO) classification system to identify brain tumors. The WHO classifies brain tumors by cell origin and how the cells behave, from the least aggressive (benign) to the most aggressive (malignant). Some tumor types are assigned a grade, ranging from Grade I (least malignant) to Grade IV (most malignant), which signifies the rate of growth. There are variations in grading systems, depending on the tumor type. The classification and grade of an individual tumor help predict its likely behavior. The most frequently diagnosed types include acoustic neuroma, astrocytoma (including Grade I-pilocytic astrocytoma, Grade II—low-grade astrocytoma, Grade III—anaplastic astrocytoma, and Grade IV—glioblastoma (GBM)), chordoma, CNS lymphoma, craniopharyngioma, other gliomas (brain stem glioma, ependymoma, mixed glioma, optic nerve glioma and sub ependymoma), medulloblastoma, meningioma, metastatic brain tumors, oligodendroglioma, pituitary tumors, primitive neuroectodermal (PNET), other brain-related conditions, and schwannoma.

Among children, these brain tumor types are more common: brain stem glioma, craniopharyngioma, ependymoma, juvenile pilocytic astrocytoma (WA), medulloblastoma, optic nerve glioma, pineal tumor, primitive neuroectodermal tumors (PNET), and rhabdoid tumor.

The present technology can be applied to treating any brain tumor, including but not limited to the aforementioned types and grades, so long as angiogenesis has been triggered. In practice, this benchmark pertains at least when a tumor is detectable by Mill, i.e., when it has grown to a size such that new vascularisation is required. Thus, the inventive methodology is suitable for treating a primary brain tumor or a metastatic secondary) brain tumors, in any of the following stages:

Grade I: The tissue is benign. The cells look nearly like normal brain cells, and cell growth is slow.

Grade II: The tissue is malignant. The cells look less like normal cells than do the cells in a grade I tumor.

Grade III: The malignant tissue has cells that look very different from normal cells. The abnormal cells are actively growing. These abnormal-appearing cells are termed anaplastic.

Grade IV: The malignant tissue has cells that look most abnormal and tend to grow very fast.

Different tumor types are known to overexpress certain receptors on their cell surface. For instance, breast cancers that metastasize to the brain tend to have a larger proportion of metastatic breast cancer cells that overexpress HER2 receptor (Palmieri et al., 2007). The same authors showed that EGF receptor expression also is much higher in brain metastases. In another example, the α3β1 integrin receptor has been shown to be overexpressed in lung cancer cells that have metastasized to the brain (Yoshimasu et al., 2004).

So informed, a treatment according to the present description of brain metastases resulting from a particular primary cancer could be adapted accordingly to use a targeting ligand, for the agent-packaged minicells, that has a specificity appropriate to the primary cancer. Thus, for brain metastases resulting from a primary breast cancer a treatment could employ a ligand that exhibits HER2 specificity, with the ligand attached to the minicell. Similarly, to treat brain metastases caused by primary lung cancer, the ligand would be one that exhibits α3β1 specificity, such as an anti-α3β1 antibody, and so on.

Pursuant to conventional technology, systemic administration of monoclonal antibodies like anti-HER2, as in the Roche/Genentech product, trastuzumab, is understood not to treat brain metastases resulting from primary breast cancer. This understanding stems from the fact that antibody active agents do not cross the blood brain barrier effectively enough to achieve therapeutically significant concentrations in the brain mestastatic tumor. For example, see Stemmler et al. (2007) (trastuzumab levels in cerebrospinal fluid increased only under conditions of an impaired blood-brain barrier, such as meningeal carcinomatosis or radiotherapy). All the more surprising and significant, therefore, is the effectiveness of a composition as described here to treat metastatic brain cancers, targeted by a ligand in the aforementioned manner.

(E) Minicells

"Minicell" refers to a derivative of a bacterial cell that is lacking in chromosomes ("chromosome-free") and is engendered by a disturbance in the coordination, during binary fission, of cell division with DNA segregation. Minicells are distinct from other small vesicles, such as so-called "membrane blebs" (— 0.2 μm or less in size), which are generated and released spontaneously in certain situations but which are not due to specific genetic rearrangements or episomal gene expression. By the same token, intact minicells are distinct from bacterial ghosts, which are not generated due to specific genetic rearrangements or episomal gene expression. Bacterially derived minicells employed in this disclosure are fully intact and, thus, are distinguished from other chromosome-free forms of bacterial cellular derivatives characterized by an outer or defining membrane that is disrupted or degraded, even removed. See U.S. Pat. No. 7,183,105 at column 111, lines 54 et seq. The intact membrane that characterizes the minicells of the present disclosure allows retention of the therapeutic payload within the minicell until the payload is released, post-uptake, within a tumor cell.

The minicell employed in this disclosure can be prepared from bacterial cells, such as E. coli and S. typhymurium. Prokaryotic chromosomal replication is linked to normal binary fission, which involves mid-cell septum formation. In E. coli, for example, mutation of min genes, such as minCD, can remove the inhibition of septum formation at the cell poles during cell division, resulting in production of a normal daughter cell and an chromosome-less minicell. See de Boer et al., 1992; Raskin & de Boer, 1999; Hu & Lutkenhaus, 1999; Harry, 2001.

In addition to min operon mutations, chromosome-less minicells also are generated following a range of other genetic rearrangements or mutations that affect septum formation, for example, in the divIVB1 in B. subtilis. See Reeve and Cornett (1975). Minicells also can be formed following a perturbation in the levels of gene expression of proteins involved in cell division/chromosome segregation. For instance, over-expression of minE leads to polar division and production of minicells. Similarly, chromosome-less minicells can result from defects in chromosome segregation, e.g., the smc mutation in Bacillus subtilis (Britton et al., 1998), the spoOJ deletion in B. subtilis (Ireton et al., 1994), the mukB mutation in E. coli (Hiraga et al., 1989), and the parC mutation in E. coli (Stewart and D'Ari, 1992). Further, CafA can enhance the rate of cell division and/or inhibit chromosome partitioning after replication (Okada et al., 1994), resulting in formation of chained cells and chromosome-less minicells.

Accordingly, minicells can be prepared for the present disclosure from any bacterial cell, be it of Gram-positive or Gram-negative origin. Furthermore, the minicells used in the disclosure should possess intact cell walls (i.e., are "intact minicells"), as noted above, and should be distinguished over and separated from other small vesicles, such as membrane blebs, which are not attributable to specific genetic rearrangements or episomal gene expression.

In a given embodiment, the parental (source) bacteria for the minicells can be Gram positive, or they can be Gram negative, as mentioned. In one aspect, therefore, the parental bacteria are one or more selected from Terra-/Glidobacteria (BV1), Proteobacteria (BV2), BV4 including Spirochaetes, Sphingobacteria, and Planctobacteria. Pursuant to another aspect, the bacteria are one or more selected from Firmicutes (BV3) such as Bacilli, Clostridia or Tenericutes/Mollicutes, or Actinobacteria (BV5) such as Actinomycetales or Bifidobacteriales.

In yet a further aspect, the bacteria are one or more selected from Eobacteria (Chloroflexi, Deinococcus-Thermus), Cyanobacteria, Thermodesulfobacteria, thermophiles (Aquificae, Thermotogae), Alpha, Beta, Gamma (Enterobacteriaceae), Delta or Epsilon Proteobacteria, Spirochaetes, Fibrobacteres, Chlorobi/Bacteroidetes, Chlamydiae/Verrucomicrobia, Planctomycetes, Acidobacteria, Chrysiogenetes, Deferribacteres, Fusobacteria, Gemmatimonadetes, Nitrospirae, Synergistetes, Dictyoglomi, Lentisphaerae Bacillales, Bacillaceae, Listeriaceae, Staphylococcaceae, Lactobacillales, Enterococcaceae, Lactobacillaceae, Leuconostocaceae, Streptococcaceae, Clostridiales, Halanaerobiales, Thermoanaerobacterales, Mycoplasmatales, Entomoplasmatales, Anaeroplasmatales, Acholeplasmatales, Haloplasmatales, Actinomycineae, Actinomycetaceae, Corynebacterineae, Mycobacteriaceae, Nocardiaceae, Corynebacteriaceae, Frankineae, Frankiaceae, Micrococcineae, Brevibacteriaceae, and Bifidobacteriaceae.

For pharmaceutical use, a composition of the disclosure should comprise minicells that are isolated as thoroughly as possible from immunogenic components and other toxic contaminants. Methodology for purifying bacterially derived minicells to remove free endotoxin and parent bacterial cells are described in WO 2004/113507, which is incorporated by reference here in its entirety. Briefly, the purification process achieves removal of (a) smaller vesicles, such as membrane blebs, which are generally smaller than 0.2 µm in size, (b) free endotoxins released from cell membranes, and (c) parental bacteria, whether live or dead, and their debris, which are sources of free endotoxins, too. Such removal can be implemented with, inter alia, a 0.2 µm filter to remove smaller vesicles and cell debris, a 0.45 µm filter to remove parental cells following induction of the parental cells to form filaments, antibiotics to kill live bacterial cells, and antibodies against free endotoxins.

Underlying the purification procedure is a discovery by the present inventors that, despite the difference of their bacterial sources, all intact minicells are approximately 400 nm in size, i.e., larger than membrane blebs and other smaller vesicles and yet smaller than parental bacteria. Size determination for minicells can be accomplished by using solid-state, such as electron microscopy, or by liquid-based techniques, e.g., dynamic light scattering. The size value yielded by each such technique can have an error range, and the values can differ somewhat between techniques. Thus, the size of minicells in a dried state can be measured via electron microscopy as approximately 400 nm±50 nm. On the other hand, dynamic light scattering can measure the same minicells to be approximately 500 nm±50 nm in size. Also, drug-packaged, ligand-targeted minicells can be measured, again using dynamic light scattering, to be approximately 600 nm±50 nm.

This scatter of size values is readily accommodated in practice, e.g., for purposes of isolating minicells from immunogenic components and other toxic contaminants, as described above. That is, an intact, bacterially derived minicell is characterized by cytoplasm surrounded by a rigid membrane, which gives the minicell a rigid, spherical structure. This structure is evident in transmission-electron micrographs, in which minicell diameter is measured, across the minicell, between the outer limits of the rigid membrane. This measurement provides the above-mentioned size value of 400 nm±50 nm.

Another structural element of a minicell derived from Gram-negative bacteria is the O-polysaccharide component of lipopolysaccharide (LPS), which is embedded in the outer membrane via the lipid A anchor. The component is a chain of repeat carbohydrate-residue units, with as many as 70 to 100 repeat units of four to five sugars per chain. Because these chains are not rigid, in a liquid environment, as in vivo, they can adopt a waving, flexible structure that gives the general appearance of seaweed in a coral sea environment; i.e., the chains move with the liquid while remaining anchored to the minicell membrane.

Influenced by the 0-polysaccharide component, dynamic light scattering can provide a value for minicell size of about 500 nm to about 600 nm, as noted above. Nevertheless, minicells from Gram-negative and Gram-positive bacteria alike readily pass through a 0.45 µm filter, which substantiates an effective minicell size of 400 nm±50 nm. The above-mentioned scatter in sizes is encompassed by the present invention and, in particular, is denoted by the qualifier "approximately" in the phrase "approximately 400 nm in size" and the like.

In relation to toxic contaminants, a composition of the disclosure can contain less than about 350 EU free endotoxin. Illustrative in this regard are levels of free endotoxin of about 250 EU, about 200 EU, about 150 EU, about 100 EU, about 90 EU, about 80 EU, about 70 EU, about 60 EU, about 50 EU, about 40 EU, about 30 EU, about 20 EU, about 15 EU, about 10 EU, about 9 EU, about 8 EU, about 7 EU, about 6 EU, about 5 EU, about 4 EU, about 3 EU, about 2 EU, about 1 EU, about 0.9 EU, about 0.8 EU, about 0.7 EU, about 0.6 EU, about 0.5 EU, about 0.4 EU, about 0.3 EU, about 0.2 EU, about 0.1 EU, about 0.05 EU, and about 0.01 EU, respectively.

A composition of the disclosure also can contain at least about $10^8$ minicells, e.g., at least about $5 \times 10^8$. Alternatively, the composition can contain on the order of $10^9$ or $10^{10}$ minicells, e.g., $5 \times 10^9$, $1 \times 10^{10}$ or $5 \times 10^{10}$ minicells. Amongst any such number of minicells, moreover, a composition of the disclosure can contain fewer than about 10 contaminating parent bacterial cells, e.g., fewer than about 9, 8, 7, 6, 5, 4, 3, 2, or 1 parent bacterial cells.

(F) Packaging an Anti-Neoplastic Agent into Minicells

Anti-neoplastic agents, such as proteins and functional nucleic acids, that can be encoded by a nucleic acid, can be introduced into minicells by transforming into the parental bacterial cell a vector, such as a plasmid, that encodes the anti-neoplastic agent. When a minicell is formed from the parental bacterial cell, the minicell retains certain copies of the plasmid and/or the expression product, the anti-neoplastic agent. More details of packaging an expression product into a minicell is provided in WO 03/033519, the content of which is incorporated into the present disclosure in its entirety by reference.

Data presented in WO 03/033519 demonstrated, for example, that recombinant minicells carrying mammalian gene expression plasmids can be delivered to phagocytic cells and to non-phagocytic cells. The application also described the genetic transformation of minicell-producing parent bacterial strains with heterologous nucleic acids carried on episomally-replicating plasmid DNAs. Upon separation of parent bacteria and minicells, some of the episomal DNA segregated into the minicells. The resulting recombinant minicells were readily engulfed by mammalian phagocytic cells and became degraded within intracellular phagolysosomes. Moreover, some of the recombinant DNA escaped the phagolysosomal membrane and was transported to the mammalian cell nucleus, where the recombinant genes were expressed.

Nucleic acids also can be packaged into minicells directly. Thus, a nucleic acid can be packaged directly into intact minicells by co-incubating a plurality of intact minicells with the nucleic acid in a buffer. The buffer composition can be varied, as a function of conditions well known in this field, in order to optimize the loading of the nucleic acid in the intact minicells. The buffer also may be varied in dependence on the nucleotide sequence and the length of the nucleic acid to be loaded in the minicells. Once packaged, the nucleic acid remains inside the minicell and is protected from degradation. Prolonged incubation studies with siRNA-packaged minicells incubated in sterile saline showed, for example, no leakage of siRNAs.

In other embodiments, multiple nucleic acids directed to different mRNA targets can be packaged in the same minicell. Such an approach can be used to combat drug resistance and apoptosis resistance. For example, cancer patients routinely exhibit resistance to chemotherapeutic drugs. Such resistance can be mediated by over-expression of genes such as multi-drug resistance (MDR) pumps and anti-apoptotic genes, among others. To combat this resistance, minicells can be packaged with therapeutically significant concentrations of functional nucleic acid to MDR-associated genes and administered to a patient before chemotherapy. Furthermore, packaging into the same minicell multiple functional nucleic acid directed to different mRNA targets can enhance therapeutic success since most molecular targets are subject to mutations and have multiple alleles. More details of directly packaging a nucleic acid into a minicell is provided in WO 2009/027830, the contents of which are incorporated into the present disclosure in its entirety by reference.

Small molecule drugs, whether hydrophilic or hydrophobic, can be packaged in minicells by creating a concentration gradient of the drug between an extracellular medium containing minicells and the minicell cytoplasm. When the extracellular medium contains a higher drug concentration than the minicell cytoplasm, the drug naturally moves down this concentration gradient, into the minicell cytoplasm. When the concentration gradient is reversed, however, the drug does not move out of the minicells.

To load minicells with drugs that normally are not water soluble, the drugs initially can be dissolved in an appropriate solvent. For example, Paclitaxel can be dissolved in a 1:1 blend of ethanol and cremophore EL (polyethoxylated castor oil), followed by a dilution in PBS to achieve a solution of Paclitaxel that is partly diluted in aqueous media and carries minimal amounts of the organic solvent to ensure that the drug remains in solution. Minicells can be incubated in this final medium for drug loading. Thus, the inventors discovered that even hydrophobic drugs can diffuse into the cytoplasm or the membrane of minicells to achieve a high and therapeutically significant cytoplasmic drug load. This is unexpected because the minicell membrane is composed of a hydrophobic phospholipid bilayer, which would be expected to prevent diffusion of hydrophobic molecules into the cytoplasm.

Example 10 below demonstrates the loading into minicells of a diversity of representative small molecule drugs, illustrating different sizes and chemical properties: Doxorubicin, Paclitaxel, Fluoro-paclitaxel, Cisplatin, Vinblastine, Monsatrol, Thymidylate synthase (TS) inhibitor OSI-7904, Irinotecan, 5-Fluorouracil, Gemcitabine, and Carboplatin. Across the board, moreover, the resultant, small molecule drug-packaged minicells show significant anti-tumor efficacy, in vitro and in vivo. These data presented herein, therefore, clearly demonstrate the effectiveness and versatility of the minicell loading methods.

(G) Directing Minicells to Specific Mammalian Cells

Pursuant to a further aspect of this disclosure, the minicells of a composition, as described above, are directed to a target mammalian tumor cell via a ligand. In some embodiments the ligand is "bispecific." That is, the ligand displays a specificity for both minicell and mammalian (tumor) cell components, such that it causes a given minicell to bind to the target cell, whereby the latter engulfs the former. Use of bispecific ligands to target a minicell to a tumor cell is further described in WO 05/056749 and WO 05/079854, the respective contents of which are incorporated here in the entirety by reference. Once such a ligand is attached to a minicell, the unoccupied specificity ("monspecificity") of the ligand pertains until it interacts with the target (tumor) mammalian cell.

The ligand can be expressed from within the minicells or their parents and then is displayed on the minicells surface. Alternatively, the ligand can be attached to ("coated on") the cell membrane of the minicells, e.g., by virtue of ligand-receptor interaction. In either instance the ligand does not require a specificity to the minicell and only displays a specificity to a component that is characteristic of mammalian cells. That is, such component need not be unique to tumor cells, per se, or even to the particular kind of tumor cells under treatment, so long as the tumor cells present the component on their cell surface. Upon intravenous administration, minicells accumulate rapidly in the tumor microenvironment, as the present inventors discovered (see also the examples below). This accumulation, occurring as a function of the above-described leaky tumor vasculature, effects targeted delivery of minicell-packaged therapeutic payload to cells of the tumor. Still, it can be helpful and at times is preferred, in keeping with the disclosure, for the ligand to target a component of a tumor to be treated.

In either case minicells contained in an administered composition of the disclosure, upon accumulation in the brain tumor microenvironment as described above, contact and bind to the targeted tumor cells, eliciting their uptake into the cells, which then are affected by the therapeutic payload. That payload can be a cytotoxic drug, e.g., doxorubicin or any other anti-neoplastic drug, as described above. The payload also can be siRNA or miRNA, e.g., an anti-apoptosis RNAi sequence such as anti-Bcl2.

The inventors found that this targeted delivery approach is broadly applicable to a range of mammalian tumor cells, including cells that normally are refractory to specific adhesion and endocytosis of minicells. For instance, ligands comprised of an antibody directed at an anti-HER2 receptor or anti-EGF receptor efficiently bind minicells to the respective receptors on a range of targeted, non-phagocytic cells. These cells include lung, ovarian, brain, breast, prostate and skin cancer cells.

The binding thus achieved precedes rapid endocytosis of the minicells by each type of the non-phagocytic cells. More generally, a suitable target cell for the present disclosure is characterized by expression of a cell surface receptor that, upon binding of a ligand, facilitates endocytosis. Host cells normally are resistant to adhesion. Therefore, when adhered by a ligand, the host cell activates its endocytosis mechanism to remove the ligand.

The term "endocytosis" encompasses (1) phagocytosis and (2) pinocytosis, itself a category inclusive of (2a) macropinocytosis, which does not require receptor binding, as well as of (2b) clathrin-mediated endocytosis, (2c) caveolae-mediated endocytosis and (2d) clathrin-/caveolae-independent endocytosis, all of which tend to access the late-endosome/lysosome pathway. The interaction between the ligand on a minicell and a mammalian cell surface receptor, the present inventors discovered, activates a particular endocytosis pathway, involving receptor mediated endocytosis (rME) to the late-endosomal/lysosomal compartment. By virtue of such an endocytosis pathway, the present inventors further discovered that the minicells were able to release their payload into the cytoplasm of the target mammalian cell. In the event the payload is an encoding nucleic acid, the nucleic acid not only is not completely degraded in the late-endosomal/lysosomal compartment, but also is expressed in the target mammalian cell.

Ligands useful in the above-described targeted delivery approach, pursuant to this disclosure, include any agent that binds to a surface component on a target cell and to a surface component on a minicell. Preferably, the surface component on a target cell is a receptor. The ligands can comprise a polypeptide and/or carbohydrate component. Antibodies are preferred ligands.

For example, an antibody that carries specificity for a surface component, such as a tumor antigen, on the target mammalian brain tumor cells can be used efficiently to target the minicells to the target cells in the brain tumor to be treated. Examples of cell surface receptors include epidermal growth factor receptor (EGFR), vascular endothelial growth factor receptor (VEGFR), platelet-derived growth factor receptor (PDGFR) and insulin-like growth factor receptor (IGFR), which are all highly expressed in a range of solid tumors, including brain tumors and folate receptor that is over expressed in some pituitary adenomas. The bispecific ligand can also be targeted to mutant or variant receptors e.g. the IL-13Ra2 receptor that is expressed in 50% to 80% of human GBMs (Debinski et al., 2000; Jarboe et al., 2007; Okada et al., 2008; Wykosky et al., 2008) but differs from its physiological counterpart IL4R/IL13R which is expressed in normal tissues (Hershey 2003). IL13Ra2 is virtually absent from normal brain cells (Debinski and Gibo 2000). Additionally, tumors that metastasize to the brain may over express certain receptors and these receptors can also be suitable targets. For example, one study showed (Da Silva et al., 2010) that brain metastases of breast cancer expressed all members of the HER family of tyrosine kinase receptors. HER2 was amplified and overexpressed in 20% of brain metastases, EGFR was overexpressed in 21% of brain metastases, HER3 was overexpressed in 60% of brain metastases and HER4 was overexpressed in 22% of brain metastases. Interestingly, HER3 expression was increased in breast cancer cells residing in the brain.

Preferred ligands comprise antibodies and/or antibody derivatives. In its present use, the term "antibody" encompasses an immunoglobulin molecule obtained by in vitro or in vivo generation of an immunogenic response. Accordingly, the "antibody" category includes monoclonal antibodies and humanized antibodies, as well as antibody derivatives, such as single-chain antibody fragments (scFv), bispecific antibodies, etc. A large number of different bispecific protein and antibody-based ligands are known, as evidenced by the review article of Caravella and Lugovskoy (2010), incorporated here by reference in its entirety. Antibodies and antibody derivatives useful in the present disclosure also can be obtained by recombinant DNA techniques.

(H) Formulations and Administration Routes and Schedules

Formulations of a composition of the disclosure can be presented in unit dosage form, e.g., in ampules or vials, or in multi-dose containers, with or without an added preservative. The formulation can be a solution, a suspension, or an emulsion in oily or aqueous vehicles, and can contain formulatory agents, such as suspending, stabilizing and/or dispersing agents. A suitable solution is isotonic with the blood of the recipient and is illustrated by saline, Ringer's solution, and dextrose solution. Alternatively, formulations can be in lyophilized powder form, for reconstitution with a suitable vehicle, e.g., sterile, pyrogen-free water or physiological saline. The formulations also can be in the form of a depot preparation. Such long-acting formulations can be administered by implantation (for instance, subcutaneously or intramuscularly) or by intramuscular injection.

In some aspect, a minicell-containing composition that includes a therapeutically effective amount of an anti-neoplastic agent is provided. A "therapeutically effective" amount of an anti-neoplastic agent is a dosage of the agent in question, e.g., a siRNA or a chemotherapeutic drug that invokes a pharmacological response when administered to a subject, in accordance with the present disclosure.

In the context of the present disclosure, therefore, a therapeutically effective amount can be gauged by reference to the prevention or amelioration of the brain tumor or a symptom of brain tumor, either in an animal model or in a human subject, when minicells carrying a therapeutic payload are administered, as further described below. An amount that proves "therapeutically effective amount" in a given instance, for a particular subject, may not be effective for 100% of subjects similarly treated for the brain tumor, even though such dosage is deemed a "therapeutically effective amount" by skilled practitioners. The appropriate dosage in this regard also will vary as a function, for example, of the type, stage, and severity of the brain tumor. In any event, the present illustrations of in vitro testing (Examples 3 and 4) and in vivo testing (Examples 5, 7 and 8) according to the present disclosure, as well as of methodology for quantifying the distribution of drug in vivo (Example 9), when considered in light of the entire description, empower a person knowledgeable in pre-clinical and clinical testing of drug candidates to determine, through routine experimentation, the therapeutically effective amount of active agent for a particular indication. Likewise, when "therapeutically effective" is used to refer to the number of minicells in a pharmaceutical composition, the number can be ascertained based on what anti-neoplastic agent is packaged into the minicells and the efficacy of that agent in treating a brain tumor. The therapeutic effect, in this regard, can be measured with a clinical or pathological parameter such as tumor mass. A reduction or reduced increase of tumor mass, accordingly, can be used to measure therapeutic effects.

Formulations within the disclosure can be administered via various routes and to various sites in a mammalian body, to achieve the therapeutic effect(s) desired, either locally or systemically. In a particular aspect, the route of administration is intravenous injection.

In general, formulations of the disclosure can be used at appropriate dosages defined by routine testing, to obtain optimal physiological effect, while minimizing any potential toxicity. The dosage regimen can be selected in accordance with a variety of factors including age, weight, sex, medical condition of the patient; the severity or stage of brain tumor, the route of administration, and the renal and hepatic function of the patient.

Optimal precision in achieving concentrations of minicell and therapeutic agent within the range that yields maximum efficacy with minimal side effects can and typically will require a regimen based on the kinetics of agent availability to target sites and target cells. Distribution, equilibrium, and elimination of minicells or agent can be considered when determining the optimal concentration for a treatment regimen. The dosage of minicells and therapeutic agent, respectively, can be adjusted to achieve desired effects.

Moreover, the dosage administration of the formulations can be optimized using a pharmacokinetic/pharmacodynamic modeling system. Thus, one or more dosage regimens can be chosen and a pharmacokinetic/pharmacodynamic model can be used to determine the pharmacokinetic/pharmacodynamic profile of one or more dosage regimens. Based on a particular such profile, one of the dosage regimens for administration then can be selected that achieves the desired pharmacokinetic/pharmacodynamic response. For example, see WO 00/67776.

A formulation of the disclosure can be administered at least once a week to a brain tumor patient, over the course of several weeks. Thus, the formulation can be administered at least once a week, over a period of several weeks to several months.

More specifically, inventive formulations can be administered at least once a day for about 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days. Alternatively, the formulations can be administered about once every day or about once every 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days or more.

In another embodiment of the disclosure, formulations can be administered about once every week or about once every 2, 3, 4, 5, 6, 7, 8, 9, 10, 11, 12, 13, 14, 15, 16, 17, 18, 19 or 20 weeks or more. Alternatively, the formulations can be administered at least once a week for about 2, 3, 4, 5, 6, 7, 8, 9, 10, 11, 12, 13, 14, 15, 16, 17, 18, 19 or 20 weeks or more.

Alternatively, the formulations can be administered about once every month or about once every 2, 3, 4, 5, 6, 7, 8, 9, 10, 11 or 12 months or more.

The formulations can be administered in a single daily dose. Alternatively, the total daily dosage can be administered in divided doses of two, three, or four times daily.

The following examples are illustrative only, rather than limiting, and provide a more complete understanding of the disclosure.

Example 1. Preparation of Doxorubicin-Packaged, Canine EGFR-Targeted Minicells

Minicells were derived from a minCDE-chromosomal deletion mutant of *Salmonella enterica* serovar *Typhimurium, S. typhimurium*, purified, packaged with doxorubicin (dox) and targeted via attachment of a bispecific monoclonal antibody (MAb) comprising anti-minicell surface 0-polysaccharide and anti-canine EGFR specificities, (designated, $^{EGFR}$minicells$_{Dox}$), as previously described by MacDiarmid et al. (2007).

The $^{EGFR}$minicells$_{Dox}$ were initially characterized for their suitability for i.v. administration into seven dogs with late-stage brain cancers (dogs designated BCD-1 to BCD-7). Two additional dogs, BCD-8 and BCD-9 presented at the Veterinary Specialist Centre but did not go into the study due to the very late stage of their brain tumors and were euthanized. Brain biopsy samples provided the respective brain tumor cells for in-vitro studies.

Example 2. Characterisation of Anti-Human EGFR Monoclonal Antibody for Binding to Canine Brain Tumor Cells Upregulation and overexpression of EGFR is well known in ~60% of GBM cases in both humans (Smith et al., 2001) and dogs (Higgins et al., 2010). Given the unavailability of a specific canine EGFR MAb, the commercially available anti-human EGFR MAb was tested in canine and human brain tumor cell lines to determine cross-reactivity of the MAb to EGFR on canine brain tumor cells.

Where feasible, brain tumor biopsy samples were obtained from case study dogs. Tissue samples from BCD-1, -8 and -9 were treated for 10 min with 1 mg/ml collagenase in Dulbecco's modified Eagle's medium (DMEM) media containing 10% fetal calf serum (FCS) and Penstrep. Undigested tissue was removed by filtration through a double layer of sterile gauze swab. Collagenase digestion was stopped by diluting the cells with 5 ml media and centrifuging at 1,200 g for 5 min. Cells were washed with an additional 5 ml media followed by repeat centrifugation and resuspension. Cells were then plated in tissue culture flasks.

The dog GBM cell line, J3T (Rainov et al., 2000), was obtained from Dr. Michael Berens of the Translation Genomics Research Institute (Phoenix, AZ, USA). All canine brain tumor cell cultures were maintained in DMEM supplemented with 10% (vol/vol) FCS, 100 U/ml penicillin, 100 U/ml streptomycin, 2 mM l-glutamine, and 2 mM nonessential amino acids.

Human GBM-astrocytoma epithelial cell line (U87-MG) was obtained from the American Type Culture Collection (ATCC) and was grown in OPTI-MEM media (Invitrogen, USA) with 5% fetal bovine serum (FBS).

Cells were collected by detaching from the flask with 2 mM EDTA/PBS and divided into 1×10 6 cells/tube. Cells were washed twice in blocking solution (PBS with 2% BSA and 0.1% sodium azide), and incubated in blocking solution for 10 min on ice, followed by incubation with 1 μg/μ0.1 anti-human EGFR monoclonal antibody (IgG2a; Calbiochem) for 45 min on ice. After two washes with blocking solution, cells were incubated with R-phycoerythrin conjugated goat anti-mouse IgG (Molecular Probes/Invitrogen) for 45 min on ice and with gentle agitation. After two washes in blocking solution, cells were resuspended in PBS and used for flow cytometry analysis. As controls, PBS instead of the primary antibody was used to determine autofluorescence.

Stained cell suspensions were measured with the flow cytometer FC 500 using CXP Cytometer software (Beckman Coulter). The number of EGF receptors was determined by analytical flow cytometry in comparison with fluorescent R-phycoerythrin microbead standards (Quantum R-PE MESF beads; Bang Laboratories Inc, Fishers, IN, USA). The calibration curve was generated by plotting the given number of equivalent R-phycoerythrin molecules per bead versus the log of its mean fluorescence intensity. Cellular fluorescence intensity was extrapolated onto a standard fluorescence calibration curve. The values of mean fluorescence were converted into number of antibodies bound per cell after subtraction from the negative control.

Figure 1:
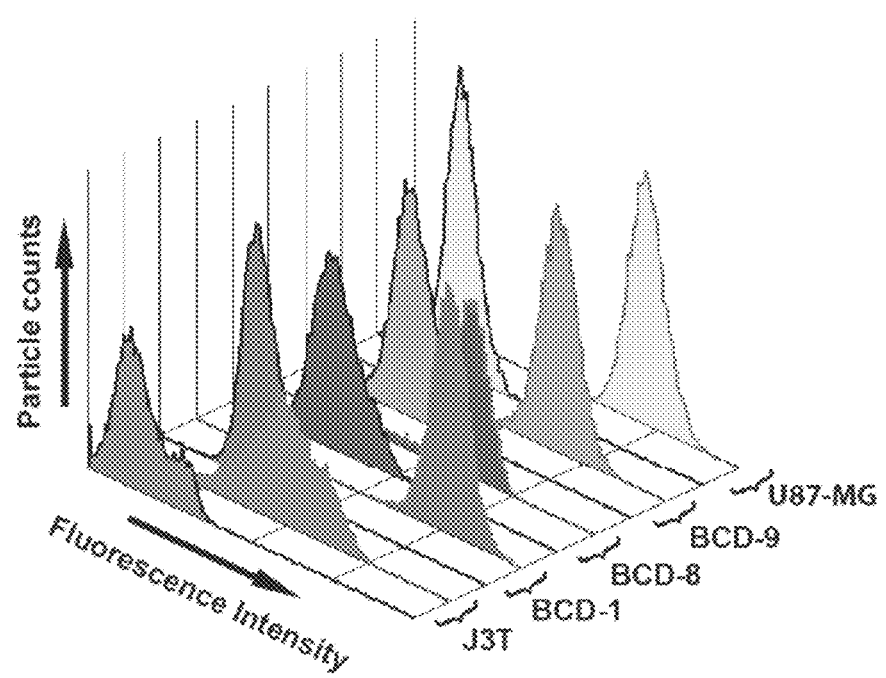
FIG. 1. EGF receptor quantitation on human (U87-MG) and canine brain tumor cells, which were treated with anti-EGFR MAb, followed by R-phycoerythrin conjugated goat anti-mouse IgG. The cells were analyzed using FACS and were compared with fluorescent R-phycoerythrin microbead standards. Control cells were treated in the same manner, except for the primary antibody. EGFR quantitation results revealed an EGFR concentration per cell (in a decreasing order) for BCD-1, U87-MG, BCD-9, BCD-8 and J3T cells was 2,866,854, 1,465,755, 930,440, 774,352 and 287,622, respectively. Results for each cell line are shown as control (curves with dark border) and anti-EGFR MAb-treated (curves without dark border).

The results showed (FIG. 1) that the MAb strongly binds to EGFR on both canine (J3T, BCD-1, -8 and -9) and human (U87-MG) brain cancer cells.

Receptor quantitation studies using FACS analyses showed (FIG. 1) EGFR concentration per cell (in a decreasing order) for BCD-1, U87-MG, BCD-9, BCD-8 and J3T cells was 2,866,854, 1,465,755, 930,440, 774,352 and 287, 622 respectively. This suggested that each of the cell types over-express EGFR.

The binding cross-reactivity of the anti-human EGFR MAb to canine EGFR was therefore confirmed following the in vitro binding assay to canine and human brain cancer cells.

Therefore, to achieve active targeting of brain tumor cells, anti-human EGFR MAb was selected to coat the Dox-packaged minicells.

Example 3. Determination of Sensitivity of Canine Brain Cancer Cells to Chemotherapeutic Drug Doxorubicin Prior to using dox-packaged, EGFR-targeted minicells to treat the dogs with late-stage brain cancers, it was important to determine if the canine brain tumor cells were sensitive or resistant to the chemotherapeutic drug doxorubicin.

Canine brain tumor cells BCD-1, -8, -9 and J3T and human brain tumor cell line U87-MG were seeded into 96 well plates at $5 \times 10^3$ cells per well. Cells were incubated overnight at 37° C., 5% $CO_2$.

Doxorubicin was added to cells in 1004, of relevant media containing serum at concentrations ranging from 1.7 nM to 8,600 nM and incubated for 72 hours.

To measure the cytotoxic effect of Doxorubicin an MTS cell proliferation assay was performed. To each well 20 uL of MTS solution (CellTitre 96® Aqueous One MTS reagent—Promega) was added and incubated in the dark for 30 minutes. Absorbance was read at a wavelength of 490 nm. Data was analysed in Prism GraphPad (La Jolla, CA, USA) using non-linear regression and a 4-parameter curve fit.

Figure 2:
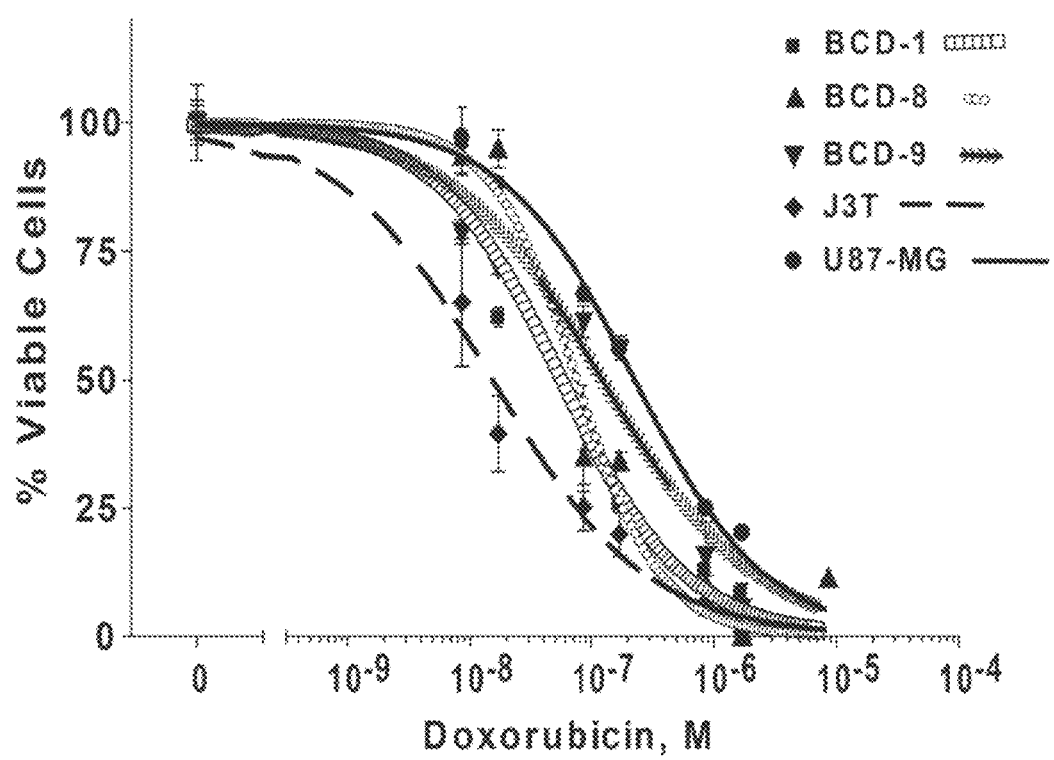
FIG. 2. Results are shown of a cell proliferation (MTS) assay to determine doxorubicin sensitivity of canine and human (U87-MG) brain cancer cells. Error bars, ±SEM.

The cell proliferation assay showed that all the above cell lines were equally sensitive to doxorubicin (FIG. 2).

Figure 3:
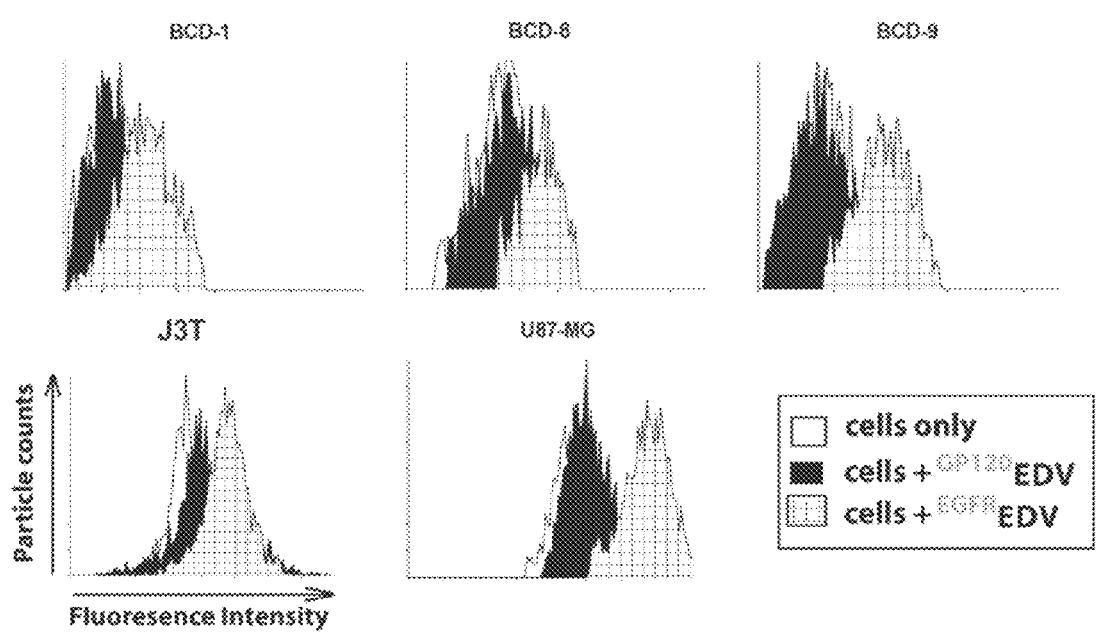
FIG. 3. Representative histograms from FACS analyses show the efficiency of binding of $^{EGFR}$minicells$_{Dox}$ to canine and human brain cancer cells. >95% of the cells in each case showed significant binding of $^{EGFR}$minicells$_{Dox}$. Cells treated with non-specifically targeted $^{gp120}$minicells$_{Dox}$ did not display any binding to the cells. Anti-gp120 antibody is directed to HIV viral capsid protein gp120, which is not found on any of the tumor cells.

Example 4. Efficiency of Binding of $^{EGFR}$Minicells-$_{Dox}$ to Canine Brain Tumor Cells The canine and human tumor cells were transfected for 2 hrs with specifically- and non-specifically-targeted minicells, $^{EGFR}$minicells$_{Dox}$ and $^{gP120}$minicells$_{Dox}$ respectively, and post-washing off non-adherent minicells, the cells were treated with anti-mouse IgG2a MAb tagged with Alexa-Fluor 488 fluorescent dye (AF-488). The gp120 MAb is directed to the human immunodeficiency virus 1 envelope glycoprotein gp120 and is not found on the surface of any of the brain tumor cell lines tested in this study. The cells were then analysed using FACS. The results showed (FIG. 3) that in each case, >95% of the cells strongly fluoresced when treated with $^{EGFR}$minicells$_{Dox}$ and the cells showed no fluorescence when treated with the control $^{gP120}$minicells$_{Dox}$.

The observed binding efficiency was further confirmed using fluorescence microscopy to directly visualize the binding of $^{EGFR}$minicells$_{Dox}$ to brain tumor cells and also the delivery of doxorubicin intracellularly in the cancer cells.

Figure 4:
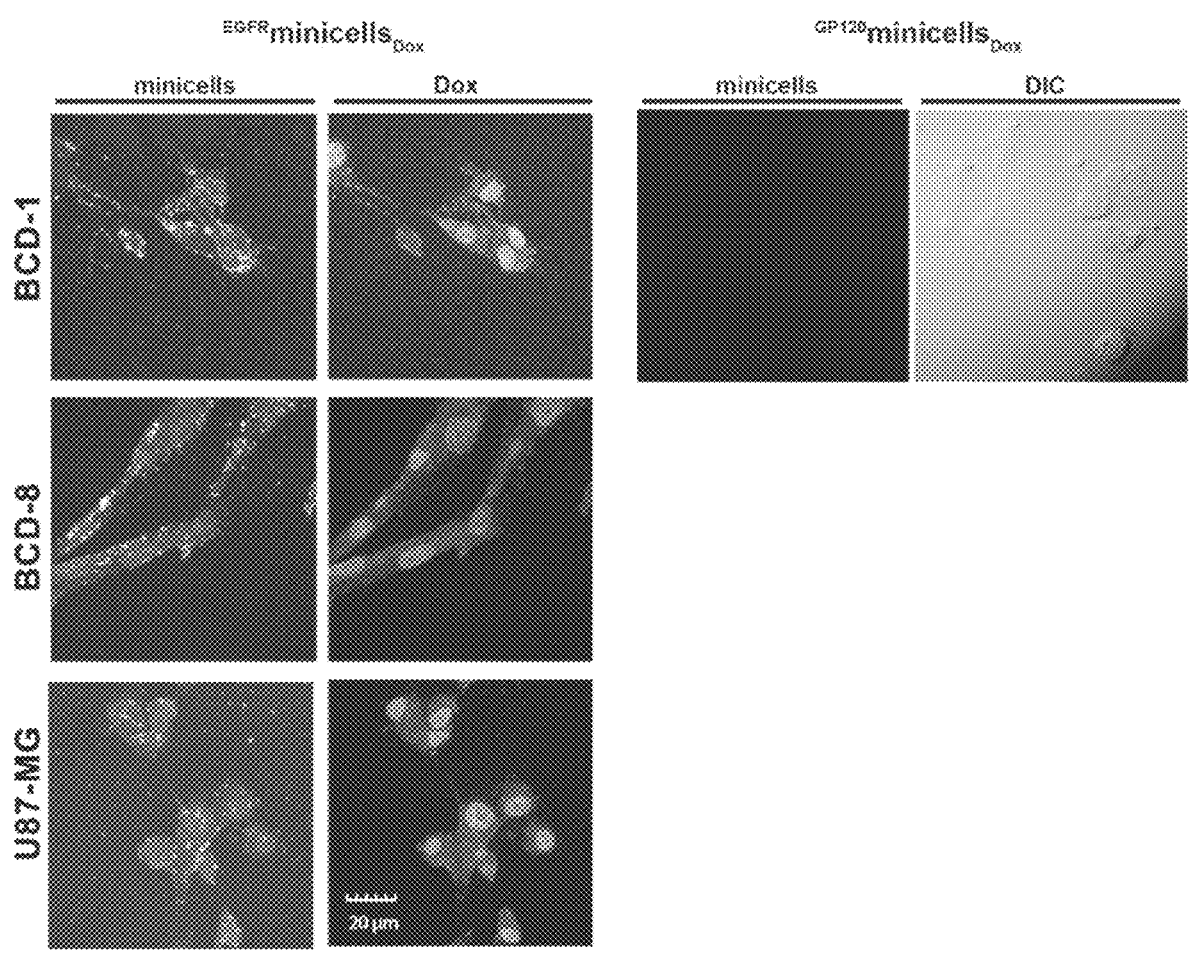
FIG. 4. Human and canine brain tumor cells were treated with $^{EGFR}$minicells$_{Dox}$ and control $^{gP120}$minicells$_{Dox}$ for 3 hours. Minicells bound to the tumor cells were visualized following treatment with goat anti-mouse IgG2a-AF488 (green fluorescence, shown lighter stippling), which binds to the anti-LPS component (IgG2a) of a bispecific antibody used to target the respective minicells. The right-hand image or each vertical panel is visualized for dox autofluorescence (red fluorescence, as darker stippling) and shows that the dox is within the nucleus of most transfected cells. The images were captured using Leica fluorescence microscope. Scale bar, 20 μm.

The $^{EGFR}$minicells$_{Dox}$ were used to transfect the canine brain tumor and human control cell lines. Three hours post-transfection and washing off excess unbound minicells, the minicells still adherent to the cell lines were revealed by labelling the EGFR targeting MAb with anti-IgG2a-AF488. The results showed (FIG. 4) that the specifically targeted minicells ($^{EGFR}$minicells$_{Dox}$) bound in large numbers to the human and canine brain cancer cells while the control minicells did not. Additionally, most of the cells treated with $^{EGFR}$minicells$_{Dox}$ showed dox autofluorescence in the cell nucleus suggesting that a significant number of minicells had been endocytosed, lysed in intracellular lysosomes and the dox had been released intracelluarly. This mechanism of intracellular delivery of drugs via bispecific antibody-targeted, drug-packaged minicells to different tumor cell lines has been delineated before by the authors of the present application and published (MacDiarmid et al., 2007).

The above results provided the rationale for packaging the minicells with dox and targeting them to EGFR.

Example 5. Treatment of Seven Late-Stage Brain Cancer Dogs with $^{EGFR}$Minicells$_{Dox}$ and Anti-Tumor Efficacy Dogs in this study were pet dogs presenting as patients to the Veterinary Specialist Centre (VSC) or the Small Animal Specialist Hospital (SASH), in Sydney, Australia. Study participation was offered to patients where standard therapy had been declined by the dog's owner, or in cases of advanced disease in which no meaningful standard therapy existed. Dogs were treated in compliance with National Health and Medical Research Council, Australia guidelines for the care and use of laboratory animals, and with EnGeneIC Animal Ethics Committee approval. Signed informed consent was obtained from all owners. All patients underwent necropsy examination at the time or death due to any cause.

All brain tumors were diagnosed by histology or cytology where feasible. Antemortem diagnoses were based on a combination of characteristic appearance on magnetic resonance imaging (MRI) and clinical signs. Histological diagnosis was deemed too invasive in these brain tumor cases and diagnosis was confirmed by necropsy.

Staging methods used varied depending on the histologic type and anatomic site of the tumor, and the clinical status. These included, but were not limited to, physical examination, complete blood count, serum biochemistry profile, urinalysis, coagulation profile, thoracic radiographs, abdominal ultrasound and magnetic resonance imaging (MRI). MRI scans were performed with a 1.5T Phillips Achieva.

Dogs were eligible for the study provided they had adequate performance status, and hematologic and serum biochemical parameters to undergo therapy. All dogs had measurable disease at study entry but there were no restrictions on stage of disease or disease burden. Patients were permitted to continue with medications to aid in the prevention of seizures and CNS edema. Medications which had been previously prescribed for concomitant conditions were also allowed to be continued. Alternative therapies were not permitted during the trial period.

Treatment with $1 \times 10^{10}$ $^{EGFR}$minicells$_{Dox}$ per dose was performed on a weekly basis. Treatment was administered via an aseptically placed peripheral vein catheter (left cephalic) in 2 ml over a 2 minute infusion.

Patients were admitted to hospital and 3 ml blood was collected via jugular venipuncture. This was placed into potassium EDTA for haematology and serum clot activator tubes for biochemistry. An additional 5 ml was collected pre-administration of $^{EGFR}$minicells$_{Dox}$ and at 4 hrs post-minicell administration. Dogs were monitored throughout the clinical treatment period and in the absence of any toxic side effects by 4 hrs post-$^{EGFR}$minicells$_{Dox}$ treatment, the dogs were sent home.

The blood was placed in a sterile tube, centrifuged at 1,580×g for 15 min at room temperature (20 to 22° C.) and the serum was collected aseptically. Sera were stored at −80° C. until required for cytokine or antibody response profiling. Patients were pre-medicated with chlorpheniramine maleate at 0.5 mg/kg and dexamethasone sodium phosphate at 0.2 mg/kg 15 minutes prior to treatment.

Case studies were carried out in seven late-stage brain cancer dogs who underwent initial clinical staging with clinical observations and MM of the brain.

The canine patients designated BCD-1 to BCD-7 showed typical clinical signs of late-stage brain tumors including seizures, ataxia, partial limb paralysis, part loss of peripheral vision and aggressive behavior (see Table 2, infra).

Intravenous (i.v.) bolus injections of $1\times10^{10}$ $^{EGFR}$minicells$_{Dox}$ (2 ml) were administered in the dogs once per week and clinical evaluation, serum hematology, biochemistry, immune response (antibody titers to minicell dominant antigen, LPS) and cytokine response studies were carried out each week. MM scans of the brain were carried out approximately every 8 weeks to determine anti-tumor response. The dose of minicells to administered in the dogs was previously determined from studies in 20 dogs with late-stage hemangiosarcoma and toxicology trials in rhesus monkeys (data not shown).

Results showed that the abnormal clinical symptoms of the brain tumor determined at the time of clinical staging (Table 2) returned to normal after approximately five to fifteen doses of $^{EGFR}$minicells$_{Dox}$.

Response was assessed by MM scans. Response was classified according to Response Criteria In Solid Tumors (RECIST v 1.1) for solid tumors. Additionally, brain tumor volume was assessed using the formula: length×width×height×($\pi$/6). A complete response (CR) was defined as disappearance of all known gross disease, a partial response (PR) was defined as a ≥50% decrease in tumor size from baseline but not a CR, stable disease was designated for tumors not meeting the criteria or CR, PR or progressive disease and progressive disease (PD) was defined as ≥25% increase in tumor size or the appearance of new lesions.

The MM scans showed that in all dogs, the tumor growth had been arrested and in one case, BCD-2, there was no evidence of the large tumor mass (FIG. 5) after just five doses of $^{EGFR}$minicells$_{Dox}$.

Example 6. Absence of Toxicity in Dogs with Brain Cancer Despite Repeat Dosing with $^{EGFR}$Minicells$_{Dox}$ Toxicity was assessed by client questionaire for signs of dysfunction of the gastrointestinal tract (anorexia, diarrhoea, vomiting, and enteritis) and constitutional signs (lethargy/fatigue). Haematological and biochemical toxicity was determined on a weekly basis prior to each treatment. Toxicity was graded according the Veterinary Co-operative Oncology Group-common terminology criteria for adverse events (VCOG-CTCAE) following chemotherapy or biological anti-neoplastic therapy in dogs and cats v1.0.

Body weight remained unchanged throughout the course of treatment. Body temperature increased from 38.5° C. to 39° C. within the first hour post-dosing and returned to normal by 4 hours.

Serum from dogs was collected (5 ml) at pre-dose with $^{EGFR}$minicells$_{Dox}$ and 4 h post-dose. Evaluation of serum biochemical and haematological profiles (FIGS. 6 and 7) was carried out by IDEXX Laboratories (Sydney, Australia). Reference ranges for canines were provided by IDEXX laboratories.

Figure 6A:
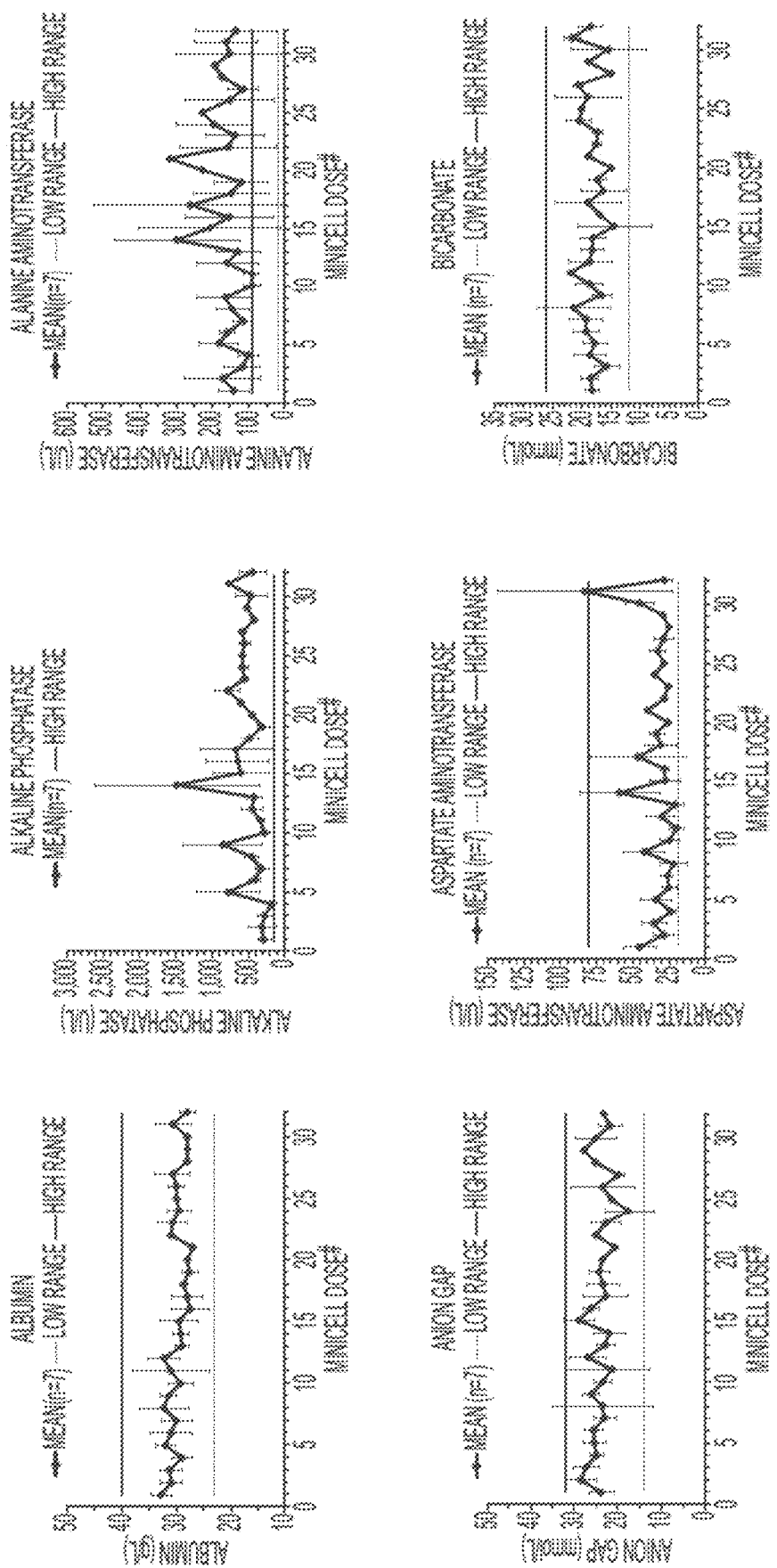
Figure 6B:
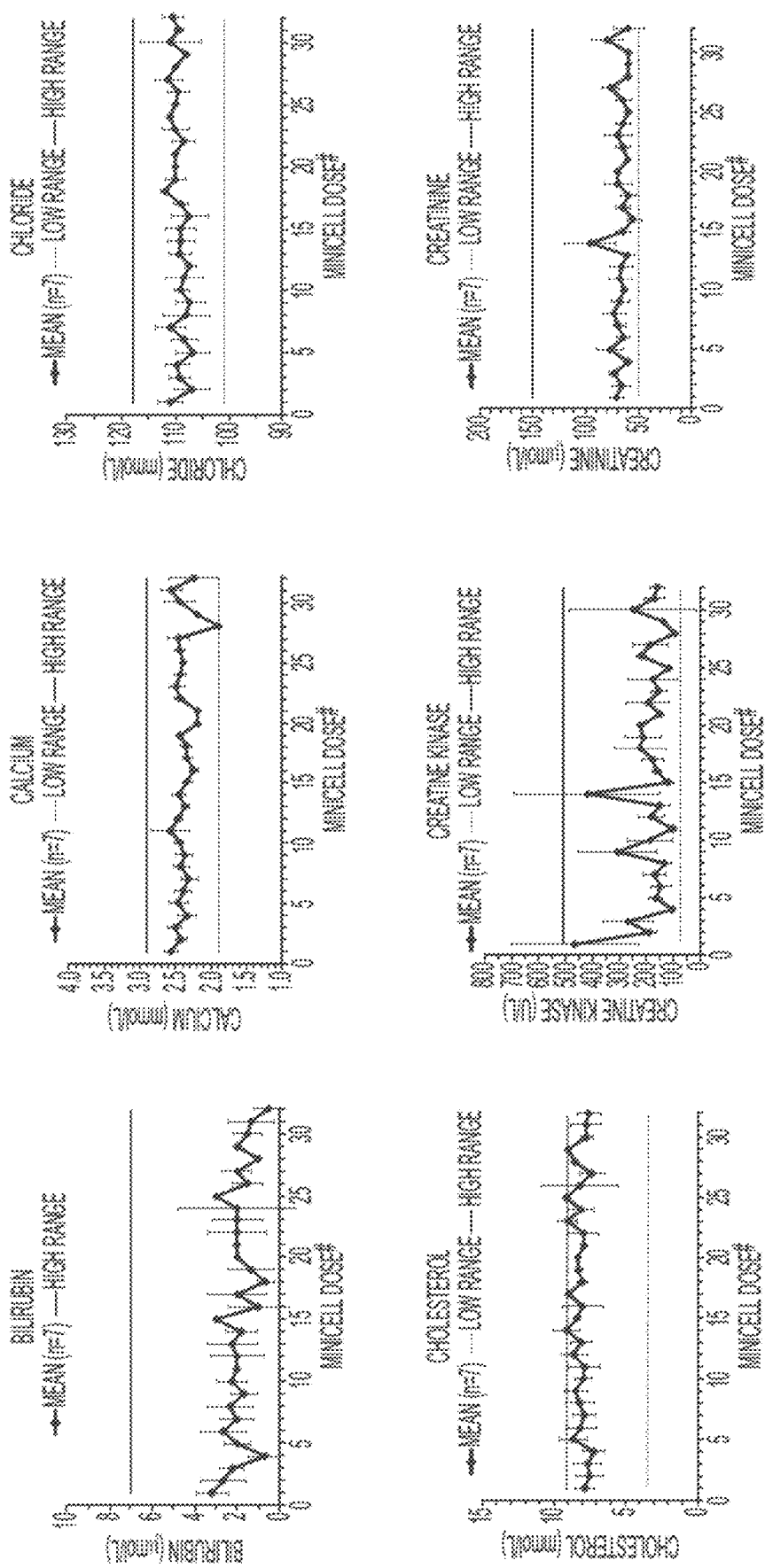
Figure 6C:
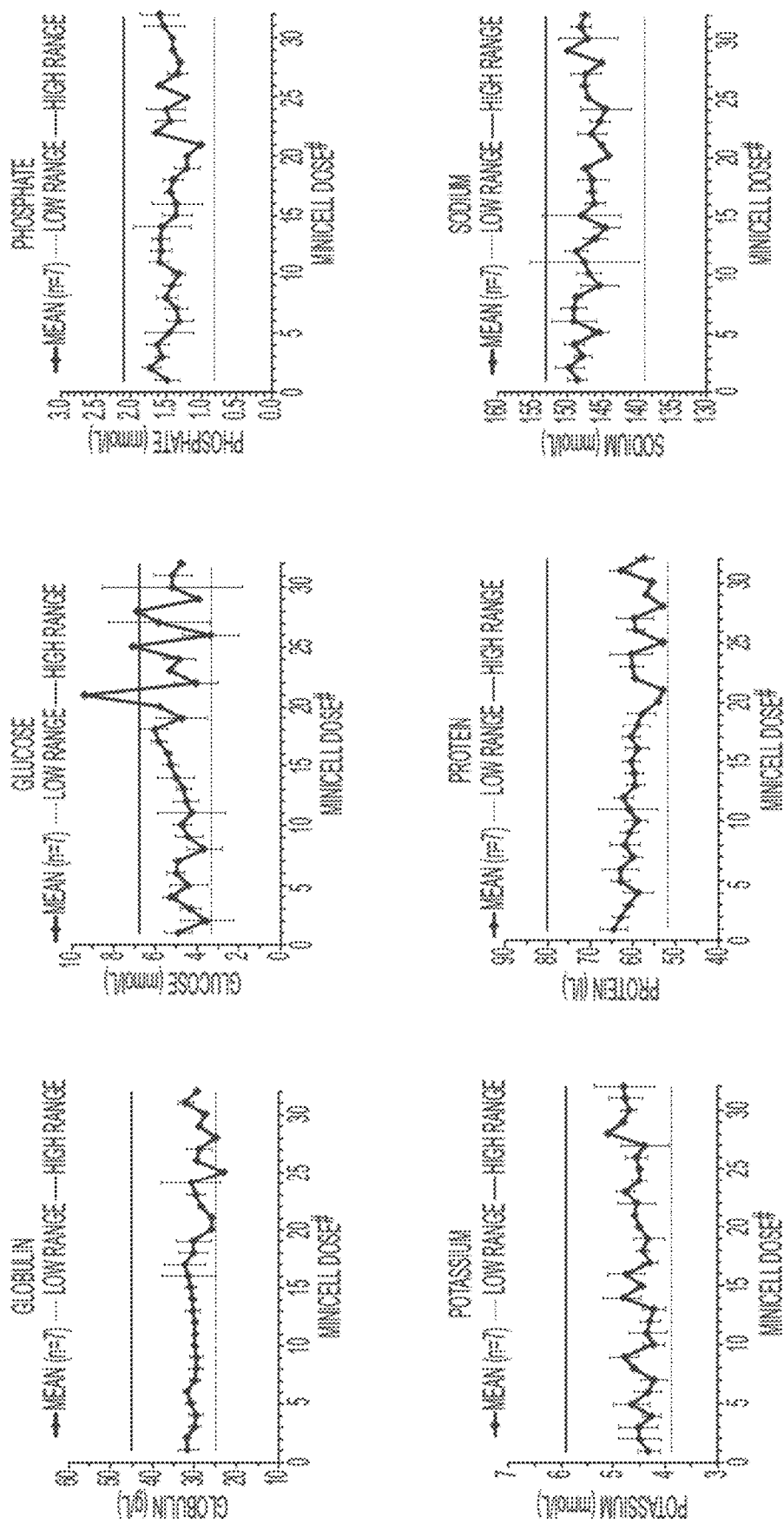

Serum biochemistry parameters remained within the normal reference range (FIG. 6). At the time of initial clinical staging, all dogs showed marked elevation in liver enzymes alanine aminotransferase (ALT) and alkaline phosphatase (ALP), likely because all dogs received conventional treatment with glucocorticoid (prednisolone) at doses ranging from 0.5 to 2 mg/kg once a day and phenobarbitone (1 mg twice a day) for difficult-to-control seizures. Liver ultrasound was routinely performed for all dogs and did not show any signs of liver tumors. Throughout the study, the livers remained normal, indicating no adverse events in the liver despite the repeat doses of $^{EGFR}$minicells$_{Dox}$.

Figure 7A:
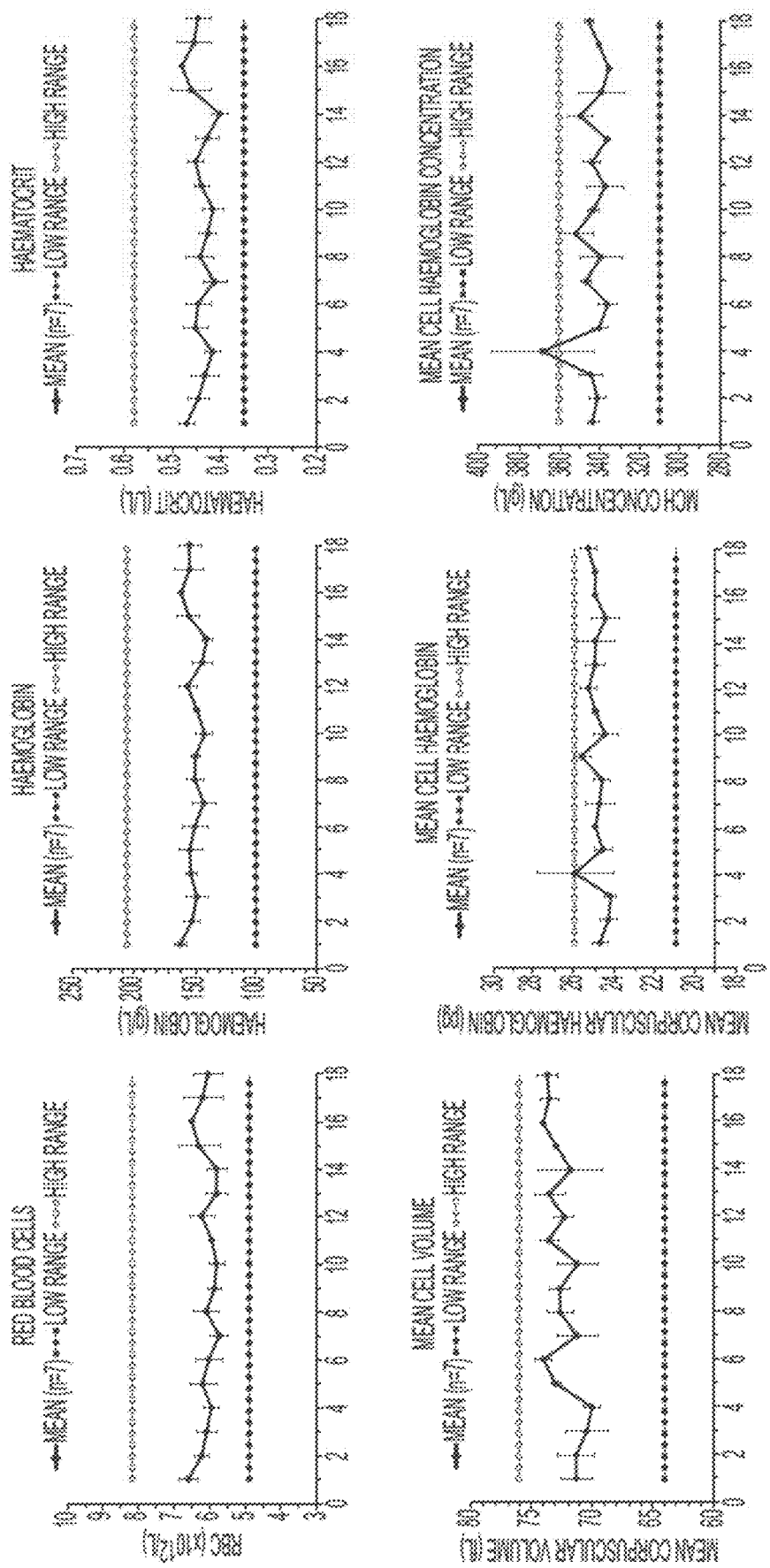
FIGS. 7A-7B. Serum hematology parameters determined post-treatment of seven dogs with brain cancers (BCD-1 to BCD7). The horizontal lines in each graph represent the normal reference range in canines. Error bars, ±SEM.
Figure 7B:
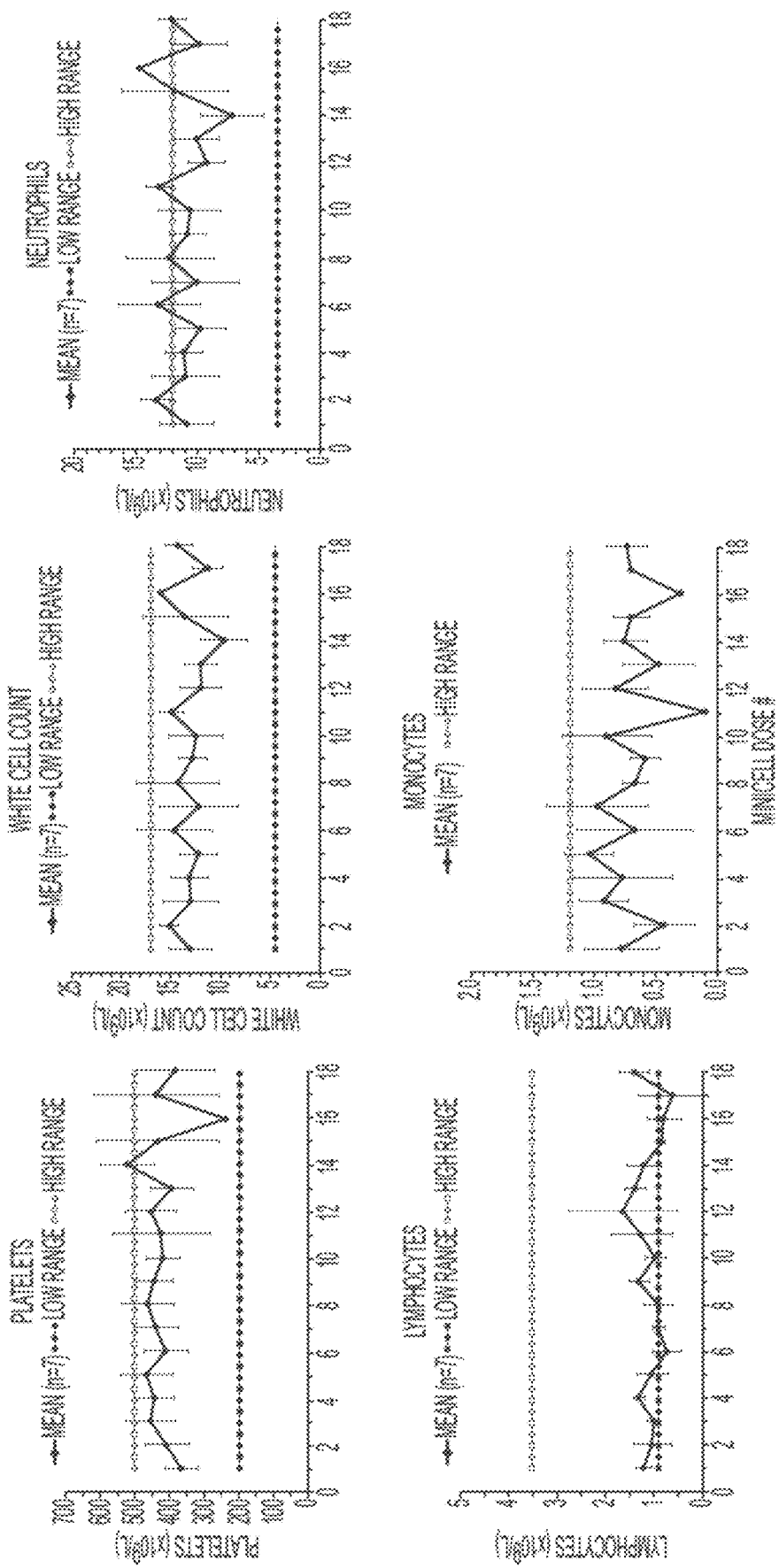

The haematological indices for all dogs also remained within the normal range throughout the study (FIG. 7).

Example 7. Cytokine and Antibody Responses in Brain Cancer Dogs Following Repeat Dosing with $^{EGFR}$Minicells$_{Dox}$ Canine serum was analysed for canine inflammatory cytokines TNFα, IL-6 and anti-inflammatory cytokine IL-10 using ELISA duoset kits supplied by R&D Systems (USA) following validation of each ELISA according to the manufacturer's instructions. High binding Microwell plates (Greiner) were developed using TMB substrate (Sigma) and read in a Biotek uQuant plate reader at 450 nm.

Figure 8A:
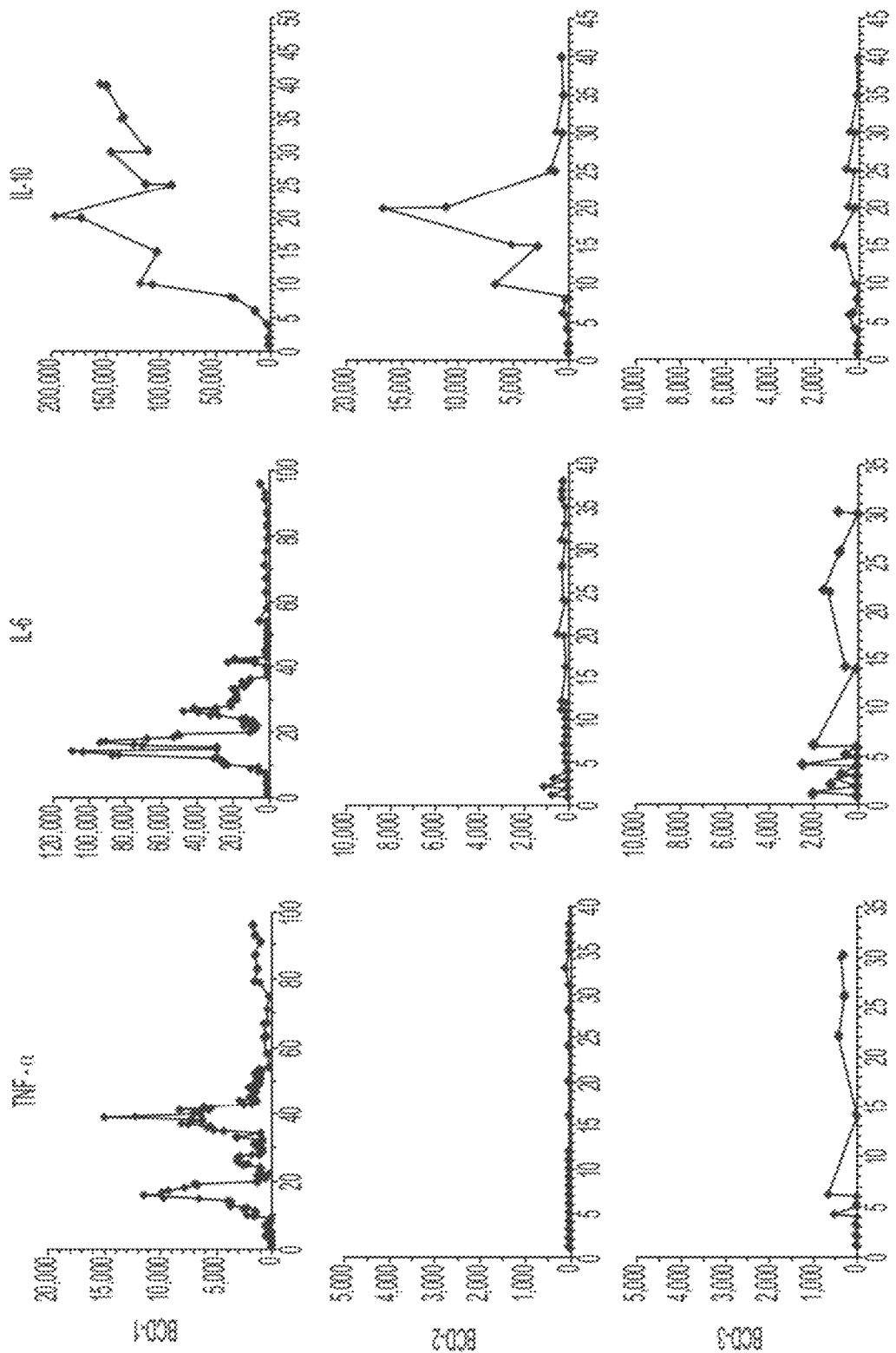
FIGS. 8A-8C. Serum TNFα, IL-6, and IL-10 responses are illustrated in the seven brain cancer dogs, post treatment with $^{EGFR}$minicells$_{Dox}$.
Figure 8B:
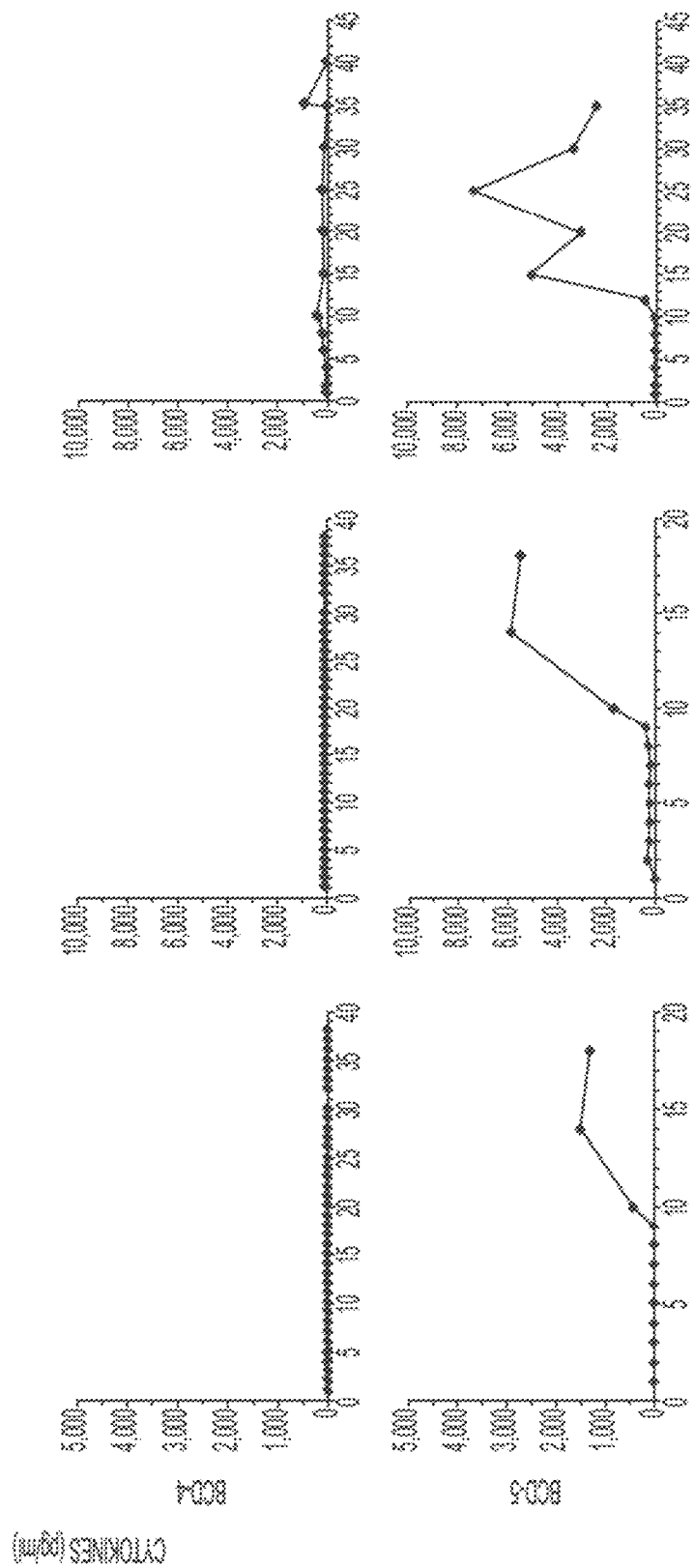
Figure 8C:
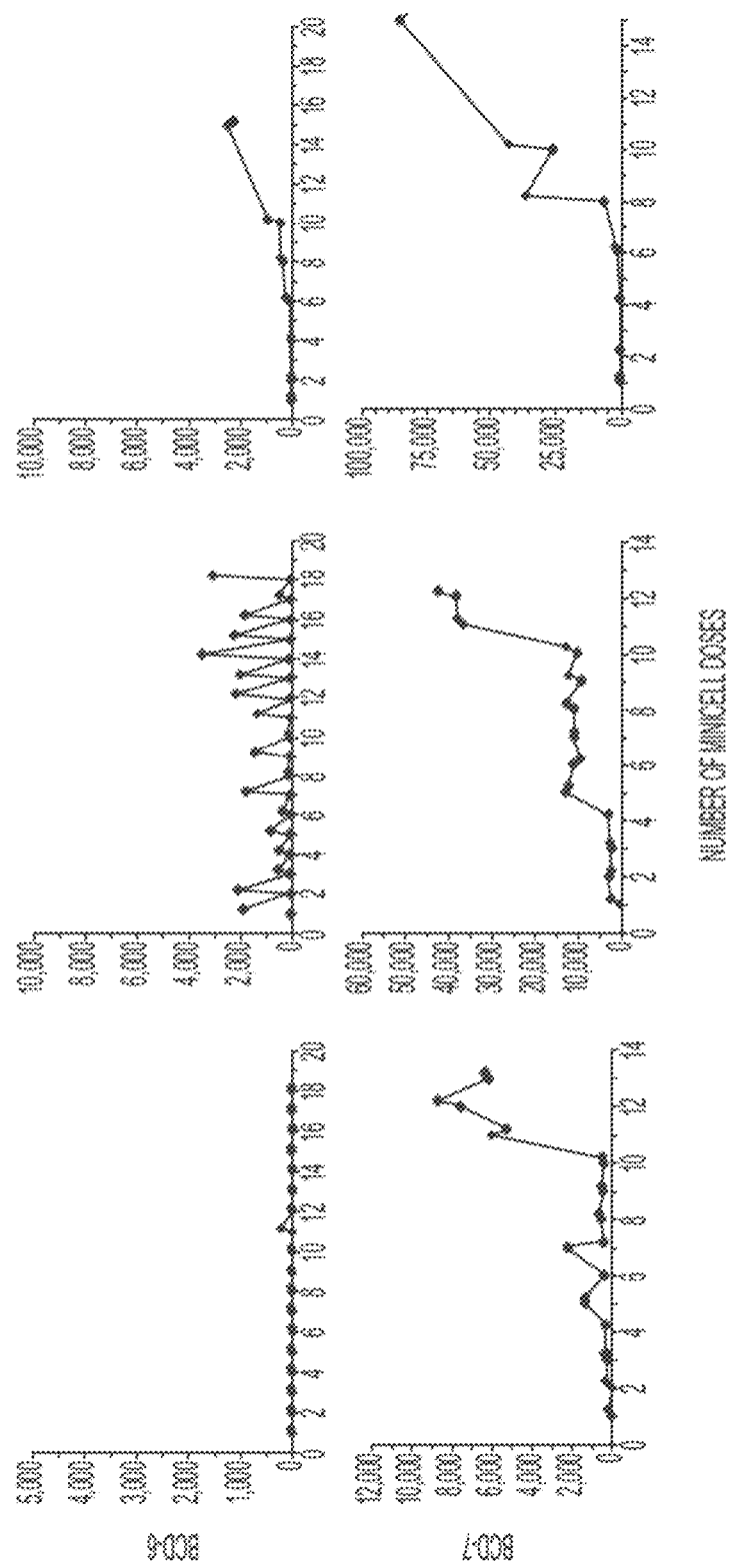

Inflammatory cytokine, TNFα, responses varied with each dog and showed no consistent pattern. Three dogs (BCD-2, -4 and -6) showed no elevation in TNFα despite repeat dosing (FIG. 8). BCD-5 and BCD-7 also showed no elevation in TNFα till dose 9 and respectively while the subsequent 3 and 7 doses respectively showed a significant rise but with no clinical adverse signs. BCD-1 had elevated TNFa at the time of clinical staging and the subsequent 97 doses of $^{EGFR}$minicells$_{Dox}$ showed no further elevation in TNFα.

Inflammatory cytokine IL-6 showed a trend where at 4 hr post-dose (FIG. 8), there was a small spike in IL-6 which returned to normal by 24 hrs. Subsequent doses did not result in an augmentation of the IL-6 spike and the trend remained the same post-each dose. An exception was BCD-4 whose IL-6 remained normal throughout the study (39 doses over 288 days).

Interestingly, the anti-inflammatory cytokine IL-10 was elevated when there were spikes in TNFα and IL-6 (FIG. 8). It is well established that monocytes and macrophages secrete IL-10 after activation with various mediators such as bacterial LPS (Sabat et al., 2010).

LPS purified from *S. typhimurium* (Sigma) was plated in the wells (250 ng/well) in coating buffer (10 mM Na Carbonate pH 9.6) and incubated overnight at 4° C. Plates were blocked with blocking buffer containing 1% BSA in PBS for 1 h at 37° C. Serial dilutions of serum samples were added to each plate and incubated at 4° C. overnight. After washing, bound antibodies were detected with goat anti-canine IgG horseradish peroxidase (HRP) conjugate (RDI).

The antibody titer was defined as the reciprocal serum dilution that gives a half-maximal Optical Density (450 nm) reading. KC Junior Software was used to fit a 2 parameter curve to each serum sample. All samples were analyzed in duplicate and data represent the standard errors of the mean.

Figure 9:
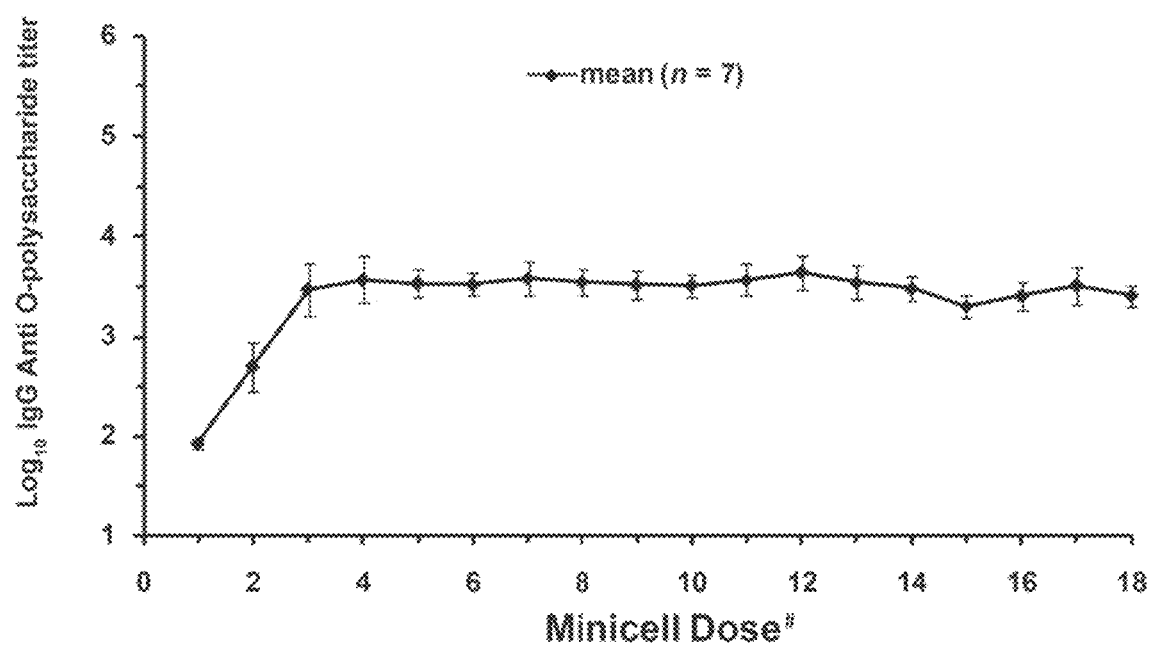
FIG. 9. Depicted are anti-LPS antibody responses in 7 brain cancer dogs (survival), post-treatment with $^{EGFR}$minicells$_{Dox}$.

The O-polysaccharide serum antibody titers (FIG. 9) showed a typical response showing a 20-fold increase in IgG titer by dose three (over three weeks) and reached a plateau with no further elevation throughout the course of the study for each dog. This is not surprising since 0-polysaccharide component of the LPS is known to be a T-cell independent type 1 antigen and that these antigens activate B cells primarily by stimulating mitogenic receptors, for example Toll-like receptors (TLRs).

Figure 10:
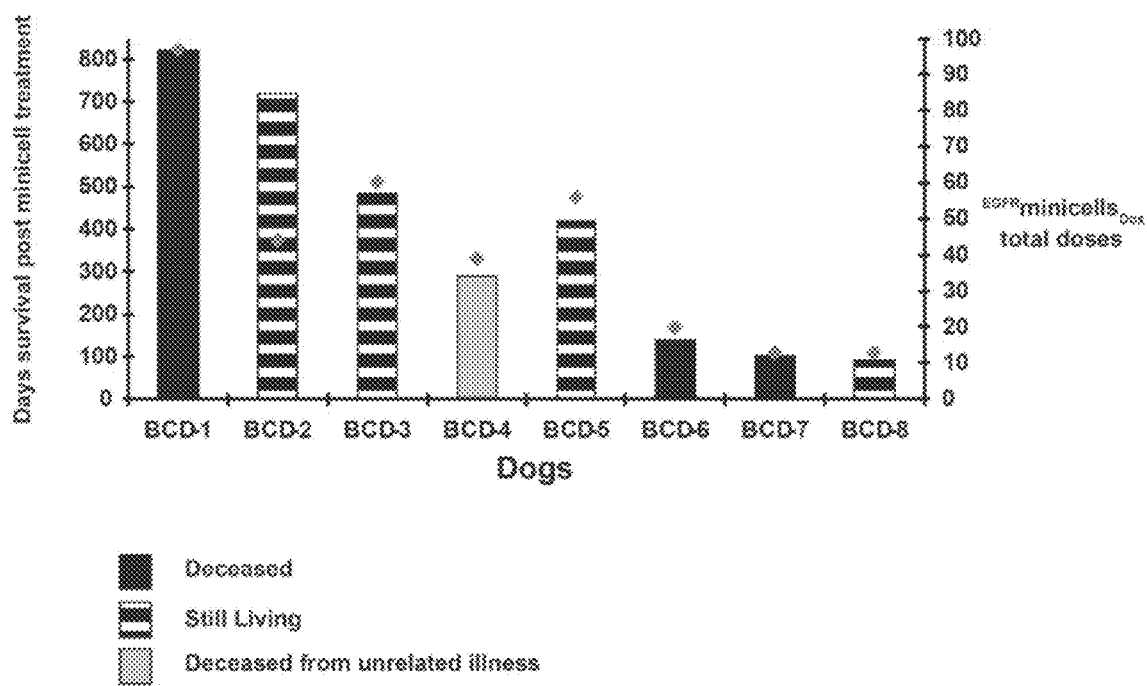
FIG. 10. Survival (in days) is illustrated for the 7 dogs with brain cancer (left hand y-axis and represented with bars), along with number of doses of $^{EGFR}$minicells$_{Dox}$ administered (right hand y-axis and shown as diamonds associated with each bar). Striped bars indicate dogs that are on-going and in remission. Darker solid bars indicate dogs that showed stable disease until the tumor recurred, possibly due to development of dox-resistance, and these dogs were euthanized. The lighter solid bar is for a dog that was in remission but died due to an unrelated infection.

Example 8. Number of Repeat Doses of $^{EGFR}$Minicells$_{Dox}$ Administered and Survival of Dogs with Late-Stage Brain Cancers Interestingly, dogs BCD-1 to BCD-7 survived 822, 709, 471, 288, 408, 140 and 101 days respectively and received 97, 43, 44, 39, 32, 20 and 13 doses of $^{EGFR}$minicells$_{Dox}$ respectively (FIG. 10). BCD-2, -3 and -5 are on-going and BCD-2 has not received a dose for over 300 days with no recurrence of the tumor. BCD-4 survived 288 days and remained with stable disease but succumbed to a kidney infection. Post mortem analysis revealed that the death was not related to the brain tumor. Surprisingly, despite the very large number of doses of $^{EGFR}$minicells$_{Dox}$ administered systemically, there were no clinical signs of adverse events.

Example 9. In-Vivo Imaging of $^{EGFR}$Minicells in the Brain of Two Dogs with Late-Stage Brain Cancer Nanoparticle biodistribution in vivo, particularly in a large animal species, has been hampered due to the very small size of the particles, ability to carry sufficient fluorescent molecules per particle to enable visualization and concentration achieved in vivo in any particular organ. Additionally, the current understanding that nanoparticles larger than 12 nm would not enter brain tumors due to the presence of the BBB. However, the striking anti-tumor efficacy observed in all 7 dogs prompted us to determine if the $^{EGFR}$minicells$_{Dox}$ do somehow gain entry into brain tumors despite their forbiddingly large size of ~400 nm.

The $^{EGFR}$minicells were radio-labeled with 123 Iodine and $1 \times 10^{10}$ mincells were administered i.v. in BCD-3 and BCD-5. The dogs were sedated and imaged using Single-photon emission computed tomography (SPECT). Both dogs also had prior MM scans to clearly show the tumor size and location.

The animals were injected with approximately 40 MBq of the radiolabelled [$^{123}$I]-$^{EGFR}$minicells and imaged at varying time points over the following 4 h. All imaging was performed on a Picker 3000XP triple-detector SPECT (Single Photon Emission Computed Tomography) gamma camera fitted with low energy, all purpose parallel hole collimators. All acquisitions used a photopeak window setting of 159 keV±10%. The animals were given some light anaesthesia prior to imaging. One dog (BCD-3) was imaged non-tomographically at 30 minutes and 3 hours post-injection in a supine position to study the biodistribution. Multiple planar images covering head and torso were collected in 256×256 matrices for 2 minutes per bed position at both time points and joined post-acquisition to give whole body 2D scans. All tomographic (SPECT) images were acquired in 128×128 matrices, using 120 projections of 3° radial increments (360° total) for 20 seconds per projection. All data were transferred to an off-line nuclear medicine workstation (HERMES, Nuclear Diagnostic, Stockholm, Sweden) and reconstructed using an iterative reconstruction algorithm (OSEM, 8 subsets, 4 iterations). The images were reconstructed with a software zoom of 2.0 to give voxels measuring 1.78×1.78×2.56 mm (X×Y×Z). The images were post-reconstruction filtered with a Butterworth filter of order 10 and cut-off of 1.25 cycles·pixel-1. Previously acquired MRI scans on the dogs were imported into the workstation and the anatomical (MRI) and functional (SPECT) scans were registered in software.

Whole body scans (FIGS. 11$ci$ and $ii$) showed intense uptake of the labelled [$^{123}$I]-$^{EGFR}$minicells in the liver from the earliest time-point (30 minutes post-injection). This fact, plus lack of early visualization of thyroid, indicated good labeling of the minicells. Excretion into bowel was visible in the later images, as was some bilateral glandular uptake in the neck and a small amount of thyroidal uptake of (presumed) free [$^{123}$I]-iodide present.

Figure 11:
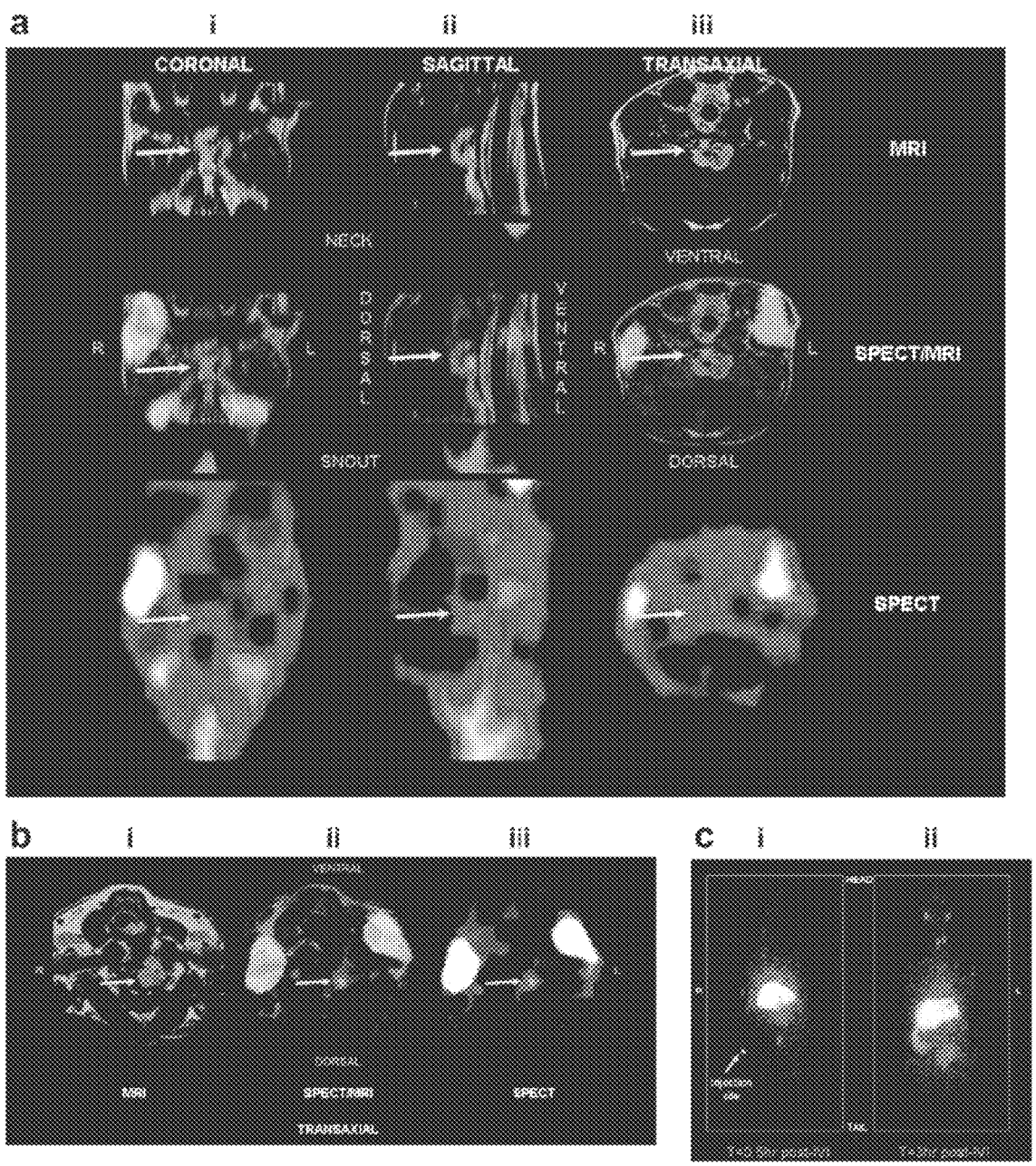
FIG. 11. (a) The co-registered T1 post-contrast MRI and SPECT scans are shown separately, (i) and (iii), and in a fused image display (ii) in the three orthogonal planes (coronal, sagittal, and transaxial). The area of uptake and the region to which it was localized are indicated by the arrows. The uptake was lower than in the extra-cerebral foci, seen bilaterally on either side of the head, but it was the only uptake observed inside the brain.

The SPECT images of the brain (FIGS. 11$ai$-$iii$ and 11$biii$; SPECT) showed a focus of radioactivity in the area corresponding to the brain tumor seen on the MM scan (FIG. 11$ai$-$iii$ and 11$bi$; MM). The co-registered T1 post-contrast MM and SPECT overlaid images (FIGS. 11$ai$-$iii$ and 11$bii$; SPECT/MRI) showed that the focused radioactivity was localized in the core of the tumor in each dog.

These examples demonstrate anti-tumor efficacy in 100% of the cases with late-stage brain tumors, an unprecedented result achieved with the present disclosure. It also is a very surprising result, given the following considerations.

1. Drugs sized on the order of doxorubicin (579.98 Daltons), such as paclitaxel (853.9 Daltons) and vinblastine (810.9 Daltons), would never have been considered heretofore for systemic (i.v.) delivery and treatment of brain tumors. Given the consensus cutoff of abut 400 Daltons, as discussed above, they were not expected to cross the BBB at all.

2. Decades of research have yielded Temozolomide as the sole FDA-approved drug for the treatment of brain cancers; this, because it is the only drug that has a molecular weight, 194.15 Daltons, that is below the perceived 400-dalton cutoff for crossing the BBB.

3. Even if it had been considered for treatment of brain tumors, doxorubicin in conventional chemotherapy normally is administered at a dose of 100 mg to 125 mg in an average patient (60 kg). This equates to 100,000 μg to 125,000 μg per i.v. dose, deemed a minimum to achieve therapeutic efficacy in treating some cancers. Pursuant to the disclosure, by contrast, the doxorubicin dose carried in $1 \times 10^{10}$ $^{EGFR}$millicells$_{Dox}$ is about 4 μg, which is 25,000-fold to 31,250-fold less than the dose administered for conventional dox chemotherapy. This divergence from conventional practice, in accordance with the disclosure, would have combined with the current understanding of cancer treatment to dissuade the clinician from considering the prospect of such a low drug dose in any context, let alone in the context of brain cancers.

4. The use of the minicell delivery vehicle pursuant to the disclosure contradicts the consensus size limits, discussed above, which in turn are informed by a conventional view of the breached BBB in brain tumors. Yet, the data obtained with the disclosure show that intact, bacterially derived minicells rapidly enter into brain tumors in significant concentrations, enabling, for example, the imaging of the radiolabeled minicells in the brain tumor microenvironment. The results also demonstrate highly significant tumor stabilization/regression in every one of the subjects treated, an unprecedented achievement that underscores an effective therapeutic paradigm, in keeping with the disclosure, for a field of clinical oncology previously typified by only abysmal results.

TABLE 2

Example 10. Packaging of a variety of small molecule drugs into minicells

| Brain cancer dog (BCD) | Weight (kg) | Body surface area (m$^2$) | Species | Age | Male/ Female | Clinical signs at the time of staging | Diagnosis |
|---|---|---|---|---|---|---|---|
| BCD-1 | 23.18 | 0.81 | Labrador-Retriever Cross | 5 yrs | Male | Hypermetria, falling towards left, cranial nerve deficits on the left side. ataxic, especially in the hind end. Tended to walk in a lateral, "half-pass" fashion, but did not fall over. Severe muscle wastage. | Choroid plexus carcinoma |
| BCD-2 | 33.27 | 1.03 | Golden Retriever | 7 yrs 6 months | Female | Presented post-seizure. Neurological examination indicated proprioceptive deficits in the right hind leg. | N/A |
| BCD-3 | 8.65 | 0.42 | Terrier crossbreed | 12 yrs | Male | Lack of papillary light reflex in the right eye. | N/A |
| BCD-4 | 32.90 | 1.03 | Boxer | 10 yrs | Female | Presented for seizuring. Bilaterally absent papillary light reflexes. | Astrocytoma |
| BCD-5 | 6.50 | 0.35 | Jack Russel Terrier | 15 yrs | Male | Presented for seizuring. Upper motor neuron signs to both the front right and rear right limbs. | N/A |
| BCD-6 | 22.66 | 0.80 | Staffordshire Bull Terrier | 11 yrs | Male | Presented for seizuring. Proprioceptive deficits in both hind legs. All other findings normal. | Poorly differentiated malignant meningioma |
| BCD-7 | 23.50 | | Boxer | 7 yrs | Male | Circling to the left, aggressive behavior, inapetance, weight loss. | Well differentiated astrocytoma |

N/A: Dog alive and tumor tissue not available

Example 10. Packaging of a Variety of Small Molecule Drugs into Minicells

This example illustrates both the feasibility of loading a diverse number of small molecule drugs into minicells and the significant anti-tumor efficacy of the resultant, small molecule drug-packaged minicell-containing compositions. The involved small molecule drugs were:

A. Doxorubicin,
B. Paclitaxel,
C. Fluoro-paclitaxel,
D. Cisplatin,
E. Vinblastine,
F. Monsatrol,
G. Thymidylate synthase (TS) inhibitor OSI-7904
H. Irinotecan,
I. 5-Fluorouracil,
J. Gemcitabine, and
K. Carboplatin.

Packaging of Doxorubicin, vinblastine and paclitaxel. The effectiveness of packaging of doxorubicin, fluorescent vinblastine and flouro-paclitaxel into intact minicells has been demonstrated in the present inventors' publication, MacDiarmid et al., Cancer Cell 11: 431-45 (2007). FIG. 1E of MacDiarmid et al. Cancer Cell (2007), with different fluorescence colors to show that minicells were packaged with large amounts of doxorubicin (DOX), vinblastine (VIN) and paclitaxel (PAC), respectively.

Doxorubicin, flouro-paclitaxel and cisplatin did not leak out of minicells once packaged. MacDiarmid et al. Cancer Cell (2007) further employed kinetics to demonstrate that, not only were drugs (doxorubicin, flouro-paclitaxel and cisplatin) sufficiently loaded into intact minicells, these drugs did not leak out of the intact minicells once packaged (see, FIG. 2A in the article).

Doxorubicin and paclitaxel packaged minicells were effective in treating breast cancer xenografts. Moreover, data presented in FIG. 4A of MacDiarmid et al. Cancer Cell (2007) show that human breast cancer xenografts were effectively treated with doxorubicin- or paclitaxel-packaged minicells.

Anti-tumor effect of monastrol-packaged minicells. Another article published by the present inventors, MacDiarmid et al., Cell Cycle 17: 1-7 (2007), presented data to demonstrate the effectiveness of monastrol-packaged minicells in inhibiting tumor growth in mice containing human breast cancer xenografts (see FIG. 1A in the article).

As shown in FIG. 1A, monastrol was effectively packaged into intact minicells and human breast cancer xenograft were effectively treated with monastrol-packaged minicells.

Anti-tumor effect of minicells packaged with thymidilate synthase inhibitor OS1-7904. Human colon cancer xenografts, likewise, were effectively treated with drug-loaded minicells. FIG. 1B of MacDiarmid et al. (2007) shows that OSI-7904-loaded minicells were more effective, at a dose that was ~385-fold less than the liposomal formulation of OSI-7904L, than the liposomal formulation OSI-7904L. The minicell delivery vector thus dramatically increased OSI-7904's therapeutic index.

Effective treatment of irinotecan-resistant human colon cancer xenografts. Irinotecan has also been packaged into intact minicells. Further, effective treatment of irinotecan-resistant human colon cancer xenografts following dual sequential treatment with shRNA-MDR1-packaged minicells followed by irinotecan-targeted minicells are demonstrated in FIGS. 5A and 5A in MacDiarmid et al., *Nature Biotechnology* 27: 643-51 (2009), another publication by the present inventors.

Effective treatment of 5-Fluorouracil-resistant human colon cancer xenografts. Like irinotecan, 5-Fluorouracil was also packaged into intact minicells and effective treatment of 5-Fluorouracil-resistant human colon cancer xenografts was achieved following dual sequential treatment with shRNA-MDR1-packaged minicells followed by 5-Fluorouracil-targeted minicells. See Supplemental FIGS. 4A and 4B of MacDiarmid et al., (2009).

Effective treatment of human pancreatic cancer xenografts with Gemcitabine (Gemzar®)-packaged minicells. FIG. 12 demonstrates that human pancreatic cancer xenografts were effectively treated with Gemcitabine (Gemzar®)-packaged minicells.

Human pancreatic cancer (MIA PaCa) xenografts in Balb/c nu/nu mice were administered i.v. with either free Gemzar or EGFR-targeted, Gemzar-packaged minicells ($^{EGFR}$Minicells$_{Gemzar}$). FIG. 12 shows that although the minicell doses carried only ~50 ng of Gemzar, the anti-tumor efficacy of $^{EGFR}$Minicells$_{Gemzar}$ treatments were just as effective in terms of anti-tumor efficacy as free Gemzar that was given at a dose of 400,000 ng per dose.

Carboplatin in treating human breast cancer xenografts. The effect of carboplatin-packaged minicells to treat human breast cancer xenografts are demonstrated in FIG. 13.

Human breast cancer (MDA-MB-468) xenografts in Balb/c nu/nu micewere administered i.v. with either free carboplatin or non-targeted minicells packaged with carboplatin or EGFR-targeted, carboplatin-packaged minicells ($^{EGFR}$Minicells$_{Carboplatin}$). The results in FIG. 13 show that $^{EGFR}$Minicells$_{Carboplatin}$ treatments were highly effective in achieving tumor stabilization, even though the dose of carboplatin was ~1,000-fold lower than the free carboplatin dose.

CITED PUBLICATIONS

Allard, E., Passirani, C., Benoit, J. P. Convection-enhanced delivery of nanoparticles for the treatment for brain tumors. *Biomaterials* 30, 2302-2318 (2009).

Behin, A., Hoang-Xuan, K., Carpentier, A. F., Delattre, J. Y. Primary brain tumours in adults. *Lancet* 361, 323-331 (2003).

Bickel, U. How to Measure Drug Transport across the Blood-Brain Barrier. *NeuroRx.* 2, 15-26 (2005).

Black, K. L., Ningaraj, N. S. Modulation of brain tumor capillaries for enhanced drug delivery selectively to brain tumor. Cancer Control 11, 165-73 (2004).

Bobo, R. H., Laske, D. W., Akbasak, A., Morrison, P. F., Dedrick, R. L., Oldfield, E. H. Convection-enhanced delivery of macromolecules in the brain. *Proc. Natl. Acad. Sci. USA* 91, 2076-2080 (1994).

Borst, P. et al. A family of drug transporters: the multidrug resistance-associated proteins. *J. Natl. Cancer Inst.* 92, 1295-1302 (2000).

Caravella J., Lugovskoy, A. Design of next-generation protein therapeutics. *Curr. Opin. Chem. Biol.* 14, 520-528 (2010).

Britton, R. A., Lin, D. C., Grossman, A. D. Characterization of a prokaryotic SMC protein involved in chromosome partitioning. *Genes Dev.* 12, 1254-9 (1998).

Caplen, N. J. RNAi as a gene therapy approach. *Expert Opin. Biol. Ther.* 3, 575-86 (2003).

Caplen, N. J., Mousses, S. Short interfering RNA (siRNA)-mediated RNA interference (RNAi) in human cells. *Ann. NY Acad. Sci.* 1002, 56-62 (2003).

Cecchelli, R., Berezowski, V., Lundquist, S., Culot, M., Renftel, M., Dehouck, M. P., Fenart, L. Modelling of the blood-brain barrier in drug discovery and development. *Nat. Rev. Drug Discov.* 6, 650-661 (2007).

Chu, C. Y., Rana, T. M. Translation repression in human cells by microRNA-induced gene silencing requires RCK/p54. *PLoS Biol.* 4, e210 (2006).

Clark-Curtiss, J. E., Curtiss, R. III Analysis of recombinant DNA using *Escherichia coli* minicells. *Methods Enzymol.* 101, 347-62 (1983).

Da Silva L et al. HER3 and downstream pathways are involved in colonization of brain metastases from breast cancer. *Breast Cancer Res.* 12, R46 (1-13) (2010).

Debinski, W., Gibo, D. M. (2000) Molecular expression analysis of restrictive receptor for interleukin 13, a brain tumor-associated cancer/testis antigen. *Mol. Med.* 6, 440-449 (2000).

Debinski, W., Slagle, B., Gibo, D. M., Powers, S. K., Gillespie, G. Y. Expression of a restrictive receptor for interleukin 13 is associated with glial transformation. *J. Neurooncol.* 48, 103-111 (2000).

de Boer, P. A., Crossley, R. E., Rothfield, L. I. Roles of MinC and MinD in the site-specific septation block mediated by the MinCDE system of *Escherichia coli*. *J. Bacteriol.* 174, 63-70 (1992).

Dehouck, B., Dehouck, M. P., Fruchart, J. C., Cecchelli, R. Upregulation of the low-density lipoprotein receptor at the blood-brain barrier: intercommunications between brain capillary endothelial cells and astrocytes. *J. Cell Biol.* 126, 465-473 (1994).

Duan, Z., et al. Inhibition of ABCB1 (MDR1) and ABCB4 (MDR3) expression by small interfering RNA and reversal of paclitaxel resistance in human ovarian cancer cells. *Mol. Cancer Ther.* 3, 833-8 (2004).

Duxbury, M. S., et al. Systemic siRNA-mediated gene silencing: A new approach to targeted therapy of cancer. *Ann. Surg.* 240, 667-74 (2004).

Eichler, A. F., Loeffler, J. S. Multidisciplinary management of brain metastases. *Oncologist* 12, 884-98 (2007).

Fox, B. D., Cheung, V. J., Patel, A. J., Suki, D., Rao, G. Epidemiology of metastatic brain tumors. Neurosurg. *Clin. N. Am.* 22, 1-6 (2011).

Fukuda, M. Radiolabeling oligosaccharides after mild periodate oxidation. Curr. Protocols *Molec. Biol.* (Suppl. 26), 17.5.1-17.5.8 (1994).

Gregory, R. I., Chendrimada, T. P., Shiekhattar, R. MicroRNA biogenesis: isolation and characterization of the microprocessor complex. *Methods Mol. Biol.* 342, 33-47 (2006).

Groothuis, D. R. The blood-brain and blood tumor barriers: a review of strategies for increasing drug delivery. *Neurooncol.* 2, 45-59 (2000).

Hadjipanayis, C. G., Fellows-Mayle, W., Deluca, N. A. Therapeutic efficacy of a herpes simplex virus in combination with radiation or temozolomide for intracranial glioblastoma after convection enhanced delivery. *Mol. Ther.* 16, 1783-1788 (2008).

Hadjipanayis, C. G., Machaidze, R., Kaluzova, M., Wang, L., Schuette, A. J., Chen, H., et al. EGFRvIII antibody-conjugated iron oxide nanoparticles for magnetic resonance imaging-guided convection-enhanced delivery and targeted therapy of glioblastoma. *Cancer Res.* 70, 6303-6312 (2010).

Hassenbusch, S. J., Gunes, S., Wachsman, S., Willis, K. D. Intrathecal clonidine in the treatment of intractable pain: a phase VII study. Pain Med. 3, 85-91 (2002).

Hau, V. S., Huber, J. D., Campos, C. R., Lipkowski, A. W., Misicka, A., Davis, T. P. Effect of guanidino modification and proline substitution on the in vitro stability and blood-brain barrier permeability of endomorphin II. *J. Pharm. Sci.* 91, 2140-9 (2002).

Hawkins, B. T., Davis, T. P. The blood-brain barrier/neurovascular unit in health and disease. *Pharmacological Reviews* 57, 173-185 (2005).

Hershey, G. K. IL-13 receptors and signaling pathways: An evolving web. *J. Allergy Clin. Immunol.* 111, 677-690 (2003).

Higgins, R. J. et al. Spontaneous canine gliomas: overexpression of EGFR, PDGFR alpha and IGFBP2 demonstrated by tissue microarray immunophenotyping. *J. Neurooncol.* 98, 49-55 (2010).

Hiraga, S., Niki, H., Ogura, T., Ichinose, C., Mori, H., Ezaki, B., Jaffe, A. Chromosome partitioning in *Escherichia coli*: novel mutants producing anucleate cells. *J. Bacteriol.* 171, 1496-1505 (1989).

Hu, Z., Lutkenhaus, J. Topological regulation of cell division in *Escherichia coli* involves rapid pole to pole oscillation of the division inhibitor MinC under the control of MinD and MinE. *Mol. Microbiol.* 34, 82-90 (1999).

Ireton, K., Gunther, N. W. 4$^{th}$., Grossman, A. D. spoOJ is required for normal chromosome segregation as well as the initiation of sporulation in *Bacillus subtilis*. *J. Bacteriol.* 176,5320-9 (1994).

Jarboe, J. S., Johnson, K. R., Choi, Y., Lonser, R. R., Park, J. K. Expression of interleukin-13 receptor a2 in glioblastoma multiforme: Implications for targeted therapies. *Cancer Res.* 67, 7983-7986 (2007).

Jemal, A., Siegel, R., Ward, E., Hao, Y., Xu, J., Thun, M. *J. Cancer statistics*, 2009. *CA Cancer J. Clin.* 59, 225-49 (2009).

Juillerat-Jeanneret, L. The targeted delivery of cancer drugs across the blood-brain barrier: chemical modifications of drugs or drug-nanoparticles? *Drug Discov. Today* 13, 1099-1106 (2008).

Khalil, A. M. et al. Many human large intergenic noncoding RNAs associate with chromatin-modifying complexes and affect gene expression. *Proc. Natl. Acad. Sci. USA.* 106, 11667-72 (2009).

Kota, J. et al. Therapeutic microRNA delivery suppresses tumorigenesis in a murine liver cancer model. *Cell* 137, 1005-17 (2009).

Kreuter, J., Alyautdin, R. N., Kharkevich, D. A., Ivanov, A. A. Passage of peptides through the blood—brain barrier with colloidal polymer particles (nanoparticles), *Brain Res.* 674, 171-174 (1995).

Kreuter, J., Petrov, V. E., Kharkevich, D. A., Alyautdin, R. N. Influence of the type of surfactant on the analgesic effects induced by the peptide dalargin after its delivery across the blood-brain barrier using surfactant-coated nanoparticles, *J. Control. Release* 49, 81-87 (1997).

Kreuter, J. Nanoparticulate systems for brain delivery of drugs. *Adv. Drug Deliv. Rev.* 47, (2001).

Kreuter, J., Shamenkov, D., Petrov, V., Ramge, P., Cychutek, K., Koch-Brandt, C., Alyautdin, R. Apolipoprotein-mediated transport of nanoparticle-bound drugs across the blood-brain barrier, *J. Drug Target.* 10, 317-325 (2002).

Kreuter, J., Ramge, P., Petrov, V., Hamm, S., Gelperina, S. E., Engelhardt, B., Alyautdin, R., von Briesen, H., Begley, D. J. Direct evidence that polysorbate-80-coated poly (butylcyanoacrylate) nanoparticles deliver drugs to the CNS via specific mechanisms requiring prior binding of drug to the nanoparticles, *Pharm. Res.* 20, 409-416 (2003).

Kreuter, J., Gelperina, S. Use of nanoparticles for cerebral cancer. Tumori 94, 271-277 (2008).

Kroll, R. A., Neuwelt, E. A. Outwitting the blood-brain barrier for therapeutic purposes: osmotic opening and other means. Neurosurgery 42, 1083-99 (1998).

Kusuhara, H., Sugiyama, Y. (2005) Active efflux across the blood-brain barrier: role of the solute carrier family. *NeuroRx* 2, 73-85 (2005).

Lamborn, K. R. et al. Progression-free survival: an important end point in evaluating therapy for recurrent high-grade gliomas. *Neuro Oncol.* 10, 162-70 (2008).

Laquintana, V., Trapani, A., Denora, N., Wang, F., Gallo, J. M., Trapani, G. New strategies to deliver anticancer drugs to brain tumors. *Expert Opin. Drug Deliv.* 6, 1017-1032 (2009).

Loscher, W., and Potschka, H. Role of drug efflux transporters in the brain for drug disposition and treatment of brain diseases. *Prog. Neurobiol.* 76, 22-76 (2005).

Louis, D. N. et al. The 2007 WHO classification of tumours of the central nervous system. *Acta Neuropathol.* 114, 97-109 (2007).

MacDiarmid, J. A. et al. Bacterially derived 400 nm particles for encapsulation and cancer cell targeting of chemotherapeutics. *Cancer Cell* 11, 431-445 (2007).

MacDiarmid, J. A., Madrid-Weiss, J., Amaro-Mugridge, N. B., Phillips, L. & Brahmbhatt, H. Bacterially-derived nanocells for tumor-targeted delivery of chemotherapeutics and cell cycle inhibitors. *Cell Cycle* 6, 2099-2105 (2007).

MacDiarmid, J. A. et al. Sequential treatment of drug-resistant tumors with targeted minicells containing siRNA or a cytotoxic drug. *Nat. Biotechnol.* 27, 643-651 (2009).

Moghimi, S. M., Hunter, A. C., Murray, J. C. Nanomedicine: current status and future prospects. *FASEB J.* 19, 311-330 (2005).

Morrison, P. F., Laske, D. W., Bobo, H., Oldfield, E. H., Dedrick, R. L. High-flow microinfusion: tissue penetration and pharmacodynamics. *Am. J. Physiol.* 266, R292-305 (1994).

Nicolazzo, J. A., Katneni, K. Drug transport across the blood-brain barrier and the impact of breast cancer resistance protein (ABCG2). *Curr. Top. in Med. Chem.* 9, 130-147 (2009).

Nieth, C., et al. Modulation of the classical multidrug resistance (MDR) phenotype by RNA interference (RNAi). *FEBS Lett.* 545, 144-50 (2003).

Oh, Y. K., Park, T. G. siRNA delivery systems for cancer treatment. *Adv. Drug Deliv. Rev.* 61, 850-62 (2009).

Okada, Y., Wachi, M., Hirata, A., Suzuki, K., Nagai, K., Matsuhashi, M. Cytoplasmic axial filaments in *Escherichia coli* cells: possible function in the mechanism of chromosome segregation and cell division. *J. Bacteriol.* 176, 917-22 (1994).

Okada, H., et al. Expression of glioma-associated antigens in pediatric brain stem and non-brain stem gliomas. *J. Neurooncol.* 88, 245-250 (2008).

Oritz-Zapater et al. Key contribution of CPEB4-mediated translational control to cancer progression. *Nature Medicine*, doi: 10.1038/nm.2540 (published on-line Dec. 4, 2011).

Palmieri, D., Bronder, J. L., Herring, J. M., Yoneda, T., Weil, R. J., Stark, A. M., et al. Her-2 overexpression increases the metastatic outgrowth of breast cancer cells in the brain. *Cancer Res.* 67, 4190-98 (2007).

Pardridge, W. M. Molecular biology of the blood-brain barrier. *Mol. Biotechnol.* 30, 57-70 (2005).

Pardridge, W. M. Drug targeting to the brain. *Pharm. Res.* 9, 1733-1744 (2007).

Pardridge, W. M. Blood-brain barrier delivery. *Drug Discov. Today* 12, 54-61 (2007).

Pardridge, W. M. Biopharmaceutical drug targeting to the brain. *J. Drug Target.* 18, 157-167 (2010).

Pardridge, W. M. Drug transport in brain via the cerebrospinal fluid. *Fluids Barriers CNS* 8, 1-4 (2011).

Petri, B., Bootz, A., Khalansky, A., Hekmatara, T., Muller, R., Uhl, R., et al. Chemotherapy of brain tumour using doxorubicin bound to surfactant-coated poly(butyl cyanoacrylate) nanoparticles: revisiting the role of surfactants. *J. Control. Release* 117, 51-58 (2007).

Rainov, N. G., Koch, S., Sena-Esteves, M. & Berens, M. E. Characterization of a canine glioma cell line as related to established experimental brain tumor models. *J. Neuropathol. Exp. Neurol.* 59, 607-613 (2000).

Raskin, D. M. de Boer, P. A. MinDE-dependent pole-to-pole oscillation of division inhibitor MinC in *Escherichia coli*. *J. Bacteriol.* 181, 6419-6424 (1999).

Reardon, D. A. et al. Phase II trial of murine (131)I-labeled antitenascin monoclonal antibody 8106 administered into surgically created resection cavities of patients with newly diagnosed malignant gliomas. *J. Clin. Oncol.* 20, 1389-97 (2002).

Re, F., Cambianica, I., Zona, C., Sesana, S., Gregori, M., Rigolio, R., La Ferla, B., Nicotra, F., Forloni, G., Cagnotto, A., Salmona, M., Masserini, M., Sancini, G. Functionalization of liposomes with ApoE-derived peptides at different density affects cellular uptake and drug transport across a blood-brain barrier model. Nanomedicine 7, 551-559 (2011).

Reeve, J. N., Cornett, J. B. Bacteriophage SPO1-induced macromolecular synthesis in minicells of *Bacillus subtilis*. *J. Virol.* 15, 1308-16 (1975).

Rice, S. L., Roney, C. A., Daumar, P., Lewis, J. S. The next generation of positron emission tomography radiopharmaceuticals in oncology. *Semin. Nucl. Med.* 41, 265-282 (2011).

Sabat, R. et al. Biology of interleukin-10. *Cytokine Growth Factor Rev.* 21, 331-344 (2010).

Sarin, H., Kanevsky, A. S., Wu, H., et al. Effective transvascular delivery of nanoparticles across the blood-brain tumor barrier into malignant glioma cells. *J. Transl. Med.* 6, 80 (2008).

Schinkel, A. H. P-glycoprotein, a gatekeeper in the blood—brain barrier. *Adv. Drug Del. Rev.* 36, 179-194 (1999).

Schinkel, A. H., Jonker, J. W. Mammalian drug efflux transporters of the ATP binding cassette (ABC) family: an overview. *Adv. Drug Del. Rev.* 55, 3-29 (2003).

Sioud, M. Therapeutic siRNAs. *Trends Pharmacol. Sci.* 25, 22-8 (2004).

Smith, J. S. et al. PTEN mutation, EGFR amplification, and outcome in patients with anaplastic astrocytoma and glioblastoma multiforme. *J. Natl. Cancer Inst.* 93, 1246-1256 (2001).

Steiniger, S. C., Kreuter, J., Khalansky, A. S., Skidan, I. N., Bobruskin, A. I., et al. Chemotherapy of glioblastoma in rats using doxorubicin-loaded nanoparticles. *Int. J. Cancer* 109, 759-767 (2004).

Stemmler, H. J., Schmitt, M., Willems, A., Bernhard, H., Harbeck, N., Heinemann, V. Ratio of trastuzumab levels in serum and cerebrospinal fluid is altered in HER2-positive breast cancer patients with brain metastases and impairment of blood-brain barrier. Anticancer Drugs 18, 23-28 (2007).

Stewart, L. A. Chemotherapy in adult high-grade glioma: a systematic review and meta-analysis of individual patient data from 12 randomised trials. *Lancet* 359, 1011-18 (2002).

Stewart, P. S. and D'Ari, R. Genetic and morphological characterization of an *Escherichia coli* chromosome segregation mutant. *J. Bacteriol.* 174, 4513-6 (1992).

Stupp R, Mason W P, van den Bent M J, Weller M, Fisher B, Taphoorn M J, et al. Radiotherapy plus concomitant and adjuvant temozolomide for glioblastoma. *N. Engl. J. Med.* 352, 987-996 (2005).

Sun, H. et al. (2003) Drug efflux transporters in the CNS. *Adv. Drug Del. Rev.* 55, 83-105 (2003).

Takeshita, F., et al. Systemic delivery of synthetic microRNA-16 inhibits the growth of metastatic prostate tumors via downregulation of multiple cell-cycle genes. *Mol. Ther.* 18, 181-7 (2010).

Weber, F. W. Local convection enhanced delivery of IL4-Pseudomonas exotoxin (NBI-3001) for treatment of patients with recurrent malignant glioma. *Acta Neurochir. Suppl.* 88, 93-103 (2003).

Wisse, E., Jacobs, F., Topal, B., Frederik, P., De Geest, B. The size of endothelial fenestrae in human liver sinusoids: implications for hepatocyte-directed gene transfer. *Gene Ther.* 15, 1193-1199 (2008).

Wong, E. T. et al. Outcomes and prognostic factors in recurrent glioma patients enrolled onto phase II clinical trials. *J. Clin. Oncol.* 17, 2572-2578 (1999).

Wrensch, M., Minn, Y., Chew, T., Bondy, M., Berger, M. S. Epidemiology of primary brain tumors: current concepts and review of the literature. *Neuro. Oncol.* 4, 278-299 (2002).

Wykosky, J., Gibo, D. M., Stanton, C., Debinski, W. Interleukin-13 receptor a 2, EphA2, and Fos-related antigen 1 as molecular denominators of high-grade astrocytomas and specific targets for combinatorial therapy. *Clin Cancer Res.* 14, 199-208 (2008).

Xin, H., Jiang, X., Gu, J., Sha, X., Chen, L., Law, K., et al. Angiopep-conjugated poly(-ethylene glycol)-co-poly(epsilon-caprolactone) nanoparticles as dual targeting drug delivery system for brain glioma. *Biomaterials* 32, 4293-305 (2011).

Yagüle, E., et al. Complete reversal of multidrug resistance by stable expression of small interfering RNAs targeting MDR1. *Gene Ther.* 11, 1170-4 (2004).

Yoshimasu, T., Sakurai, T., Oura, S., Hirai, I., Tanino, H., Kokawa, Y., et al. Increased expression of integrin alpha3beta1 in highly brain metastatic subclone of a human non-small cell lung cancer cell line. Cancer Sci. 95, 142-48 (2004).

Zensi, A., Begley, D., Pontikis, C., Legros, C., Mihoreanu, L., et al. Albumin nanoparticles targeted with Apo E enter the CNS by transcytosis and are delivered to neurones. *J. Control. Release* 137, 78-86 (2009).

Zhang, Y., Pardridge, W. M. Conjugation of brain-derived neurotrophic factor to a blood-brain barrier drug targeting system enables neuroprotection in regional brain ischemia following intravenous injection of the neurotrophin. *Brain Res.* 889, 49-56 (2001).

What is claimed is:

1. A method of imaging a brain tumor in a subject, comprising:
   (a) administering to the subject a composition comprising a plurality of intact, bacterially derived minicells, wherein each minicell of the plurality (i) comprises a ligand having a specificity to a non-phagocytic mammalian cell surface receptor and (ii) encompasses an imaging agent; and
   (b) imaging the localization of the plurality of intact bacterially derived minicells within the tumor wherein the tumor is a brain tumor and the brain tumor has blood vessels with fenestrations in its walls through which the minicells can extravasate passively.

2. The method of claim 1, wherein the non-phagocytic mammalian cell surface receptor is a tumor cell antigen.

3. The method of claim 1, wherein the ligand is an antibody.

4. The method of claim 3, wherein the antibody specifically recognizes a tumor cell antigen.

5. The method of claim 1, wherein the imaging agent is a radionuclide.

6. The method of claim 1, wherein the imaging agent is attached to a protein or a carbohydrate on the surface of the minicells.

7. The method of claim 6, wherein the imaging agent is attached to a bispecific antibody that is associated with the surface of the minicells.

8. The method of claim 1, wherein the imaging is performed by single-photon emission computed tomography (SPECT).

9. The method of claim 1, wherein the imaging agent is fluorescent.

10. The method of claim 1, wherein the plurality comprises at least about $10^8$ minicells.

11. The method of claim 10, wherein the plurality includes at least about $10^{10}$ minicells.

12. The method of claim 1, wherein the composition contains less than about 10 EU free endotoxin.

13. The method of claim 1, wherein the composition contains at most 1 parent bacterial cell per $10^8$ minicells.

14. The method of claim 1, wherein the brain tumor is selected from the group consisting of glioblastoma, astrocytic tumor, oligodendroglial tumor, ependymoma, craniopharyngioma, pituitary tumor, primary lymphoma of the brain, pineal gland tumor, primary germ cell tumor of the brain, and combinations thereof.

15. The method of claim 1, wherein the brain tumor is metastatic brain tumor.

* * * * *